US012630646B2

(12) United States Patent (10) Patent No.: US 12,630,646 B2
Heitzeneder et al. (45) Date of Patent: May 19, 2026

(54) CHIMERIC ANTIGEN RECEPTORS TARGETING GLYPICAN-2

(71) Applicants: THE BOARD OF TRUSTEES OF THE LELAND STANFORD JUNIOR UNIVERSITY, Palo Alto, CA (US); THE CHILDREN'S HOSPITAL OF PHILADELPHIA, Philadelphia, PA (US); The United State of America, as represented by the Secretary, Bethesda, MD (US)

(72) Inventors: Sabine Heitzeneder, Redwood City, CA (US); Robbie G. Majzner, Palo Alto, CA (US); Crystal L. Mackall, Stanford, CA (US); John M. Maris, Philadelphia, PA (US); Kristopher R. Bosse, Philadelphia, PA (US); Dimiter S. Dimitrov, Pittsburg, PA (US); Zhongyu Zhu, Frederick, MD (US)

(73) Assignees: The Board of Trustees of the Leland Stanford Junior University, Palo Alto, CA (US); The Children's Hospital of Philadelphia, Philadelphia, PA (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 107 days.

(21) Appl. No.: 17/608,832

(22) PCT Filed: May 6, 2020

(86) PCT No.: PCT/US2020/031729
§ 371 (c)(1),
(2) Date: Nov. 4, 2021

(87) PCT Pub. No.: WO2020/227447
PCT Pub. Date: Nov. 12, 2020

(65) Prior Publication Data
US 2022/0315665 A1 Oct. 6, 2022

Related U.S. Application Data

(60) Provisional application No. 62/844,695, filed on May 7, 2019.

(51) Int. Cl.
*A61P 35/00* (2006.01)
*A61K 38/17* (2006.01)
(Continued)

(52) U.S. Cl.
CPC .......... *C07K 16/303* (2013.01); *A61K 38/177* (2013.01); *A61K 38/1774* (2013.01); *A61K 39/39558* (2013.01); *A61K 40/11* (2025.01); *A61K 40/31* (2025.01); *A61K 40/4211* (2025.01); *A61K 40/4261* (2025.01); *A61K*

*45/06* (2013.01); *A61P 35/00* (2018.01); *A61P 35/04* (2018.01); *C07K 14/70517* (2013.01); *C07K 14/70521* (2013.01); *C07K 14/70578* (2013.01); *C12N 5/0636* (2013.01);
(Continued)

(58) Field of Classification Search
CPC ............ C07K 16/303; C07K 14/70517; C07K 14/70521; C07K 14/70578; C07K 2317/524; C07K 2317/526; C07K 2317/53; C07K 2317/565; C07K 2317/567; C07K 2317/622; C07K 2317/76; C07K 2319/02; C07K 2319/03; C07K 2319/33; C07K 14/7051; A61K 38/177; A61K 38/1774; A61K 39/39558; A61K 40/11; A61K 40/31; A61K 40/4211; A61K 40/4261; A61K 45/06; A61K 2039/505; A61K 2039/545; A61K 2239/31; A61K 2239/38; A61K 2239/47; A61P 35/00; A61P 35/04; C12N 5/0636; C12N 2510/00
See application file for complete search history.

(56) References Cited

U.S. PATENT DOCUMENTS 4,470,461 A 9/1984 Stapp
5,122,464 A 6/1992 Wilson et al.
(Continued)

FOREIGN PATENT DOCUMENTS

EP 0338841 A1 10/1989
WO 2017027291 A1 2/2017
(Continued)

OTHER PUBLICATIONS

Lin et al. Improved affinity of a chicken single-chain antibody to avian infectious bronchitis virus by site-directed mutagenesis of complementarity-determinig region H3. African J Biotech, 2011, 10(79): 18294-18302. (Year: 2011).*
Chen et al. GPC2 is a Potential Diagnostic, Immunological, and Prognostic Biomarker in Pan-Cancer. Front Immunol. Mar. 8, 2022; 13:857308. (Year: 2022).*
Almagro JC, Fransson J. Humanization of antibodies. Front Biosci. Jan. 1, 2008;13:1619-33. (Year: 2008).*
Griffiths et al. Human anti-self antibodies with high specificity from phage display libraries. EMBO J. Feb. 1993; 12(2):725-34 (Year: 1993).*
(Continued)

*Primary Examiner* — Julie Wu
*Assistant Examiner* — Amber K Faust
(74) *Attorney, Agent, or Firm* — Mintz Levin Cohn Ferris Glovsky and Popeo, P.C.

(57) ABSTRACT

The present disclosure generally relates to, inter alia, antibodies and chimeric antigen receptors (CARs) that bind a Glypican 2 (GPC2) antigen. The disclosure also provides compositions and methods useful for producing such antibodies and CARs, as well as methods for the diagnosis, prevention, and/or treatment of health conditions associated with the GPC2 antigen expression.

22 Claims, 54 Drawing Sheets

Specification includes a Sequence Listing.

(51) Int. Cl.

| | |
|---|---|
| *A61K 39/00* | (2006.01) |
| *A61K 39/395* | (2006.01) |
| *A61K 40/11* | (2025.01) |
| *A61K 40/31* | (2025.01) |
| *A61K 40/42* | (2025.01) |
| *A61K 45/06* | (2006.01) |
| *A61P 35/04* | (2006.01) |
| *C07K 14/705* | (2006.01) |
| *C07K 16/30* | (2006.01) |
| *C12N 5/0783* | (2010.01) |

(52) U.S. Cl.
CPC .................. *A61K 2039/505* (2013.01); *A61K 2039/545* (2013.01); *A61K 2239/31* (2023.05); *A61K 2239/38* (2023.05); *A61K 2239/47* (2023.05); *C07K 2317/524* (2013.01); *C07K 2317/526* (2013.01); *C07K 2317/53* (2013.01); *C07K 2317/565* (2013.01); *C07K 2317/567* (2013.01); *C07K 2317/622* (2013.01); *C07K 2317/76* (2013.01); *C07K 2319/02* (2013.01); *C07K 2319/03* (2013.01); *C07K 2319/33* (2013.01); *C12N 2510/00* (2013.01)

(56) References Cited

U.S. PATENT DOCUMENTS

| | | | |
|---|---|---|---|
| 2015/0125455 | A1 | 5/2015 | Green et al. |
| 2016/0024199 | A1 | 1/2016 | Dimitrov et al. |
| 2016/0229908 | A1 | 8/2016 | Igawa et al. |
| 2017/0088620 | A1 | 3/2017 | Nioi et al. |
| 2018/0305452 | A1 | 10/2018 | Orentas et al. |
| 2019/0083596 | A1 | 3/2019 | Orentas et al. |

FOREIGN PATENT DOCUMENTS

| | | | |
|---|---|---|---|
| WO | 2017083296 | A1 | 5/2017 |
| WO | 2018026533 | A1 | 2/2018 |
| WO | 2018200586 | A1 | 11/2018 |
| WO | 2020227447 | A1 | 11/2020 |

OTHER PUBLICATIONS

Klimka et al. Human anti-CD30 recombinant antibodies by guided phage antibody selection using cell panning. Br J Cancer 83, 252-260 (2000). (Year: 2000).*

Beiboer et al. Guided selection of a pan carcinoma specific antibody reveals similar binding characteristics yet structural divergence between the original murine antibody and its human equivalent. J Mol Biol. Feb. 25, 2000;296(3):833-49. (Year: 2000).*

Extended European Search Report for European Application No. 20802725.0, mailed on Dec. 2, 2022, 8 pages.

(Updated on Mar. 4, 2025) GPC2 Glypican 2 [ *Homo sapiens* (Human) ], NCBI Gene ID 221914, Accession Nos. NM 152742, and NP 689955, 5 pages.

Atschul et al. (Oct. 5, 1990) "Basic Local Alignment Search Tool", Journal of Molecular Biology, 215(3):403-410.

Caldas et al. (May 1, 2003) "Humanization of the Anti-Cd18 Antibody 6.7: An Unexpected Effect of a Framework Residue in Binding to Antigen.", Molecular Immunology, 39(15):941-952.

Devereux et al. (Jan. 11, 1984) "A Comprehensive Set of Sequence Analysis Programs for the VAX", Nucleic Acids Research, 12(1):387-395.

Dondelinger et al. (Oct. 16, 2018) "Understanding the Significance and Implications of Antibody Numbering and Antigen-binding Surface/Residue Definition", Frontiers in Immunology, 9:2278 (15 pages).

Du et al. (2008) "Molecular Basis of Recognition of Human Osteopontin by 23C3, a Potential Therapeutic Antibody for Treatment of Rheumatoid Arthritis", Journal of Molecular Biology, 382(4):835-842.

Frankel et al. (Feb. 1979) "The Rapid Determination of Binding Constants for Antiviral Antibodies by a Radioimmunoassay. An analysis of the Interaction Between Hybridoma Proteins and Influenza Virus", Molecular Immunology, 16(2):101-106.

Li et al. (2017) "Therapeutically Targeting Glypican-2 via Single-domain Antibody-based Chimeric Antigen Receptors and Immunotoxins in Neuroblastoma", Proceedings of the National Academy of Sciences, 114(32):E6623-E6631.

Sela-Culang et al. (Oct. 8, 2013) "The Structural Basis of Antibody-Antigen Recognition", Frontiers in Immunology, 4(302):1-13.

Torres et al. (Feb. 2008) "The Immunoglobulin Constant Region Contributes to Affinity and Specificity", Trends in Immunology, 29(2):91-97.

Winkler et al. (Oct. 15, 2000) "Changing the Antigen Binding Specificity by Single Point Mutations of an Anti-p24 (HIV-1) Antibody", The Journal of Immunology, 165(8):4505-4514.

International Preliminary Report on Patentability received for PCT Application No. PCT/US2020/031729, mailed on Nov. 18, 2021, 8 pages.

International Search Report and Written Opinion received for PCT Application No. PCT/US2020/031729, mailed on Aug. 25, 2020, 11 pages.

* cited by examiner

D

●———— FMC63.8aTM.41BBz

○----- GPC2.19.8aTM.41BBz

FMC63.8aTM.41BBz

GPC2.19.8aTM.41BBz

SMS-SAN

—●— FMC63.8aTM.41BBz

—○— GPC2.19.8aTM.41BBz

NBSD

GPC2.28TM.41BBz

GPC2.28TM.28z

FMC63
GPC2.8aTM.41BBz (**)
GPC2.28TM.41BBz (**)
GPC2.28TM.28z (**)

H

Human GPC2(ENSG00000213420)

⊘ prenatal (weeks post-conception)

○ pediatric (N_newborn, I_infant, To_toddler, S_school, Te_teenager)

● adult (YA_young adult, YM_young mid-age, OM_older midage, S_senior

⊘ prenatal (weeks post-conception)

○ pediatric (N_newborn, I_infant, To_toddler, S_school, Te_teenager)

● adult (YA_young adult, YM_young mid-age, OM_older midage, S_senior)

⊘ prenatal

○ Postnatal

⊘ prenatal

○ Postnatal

A

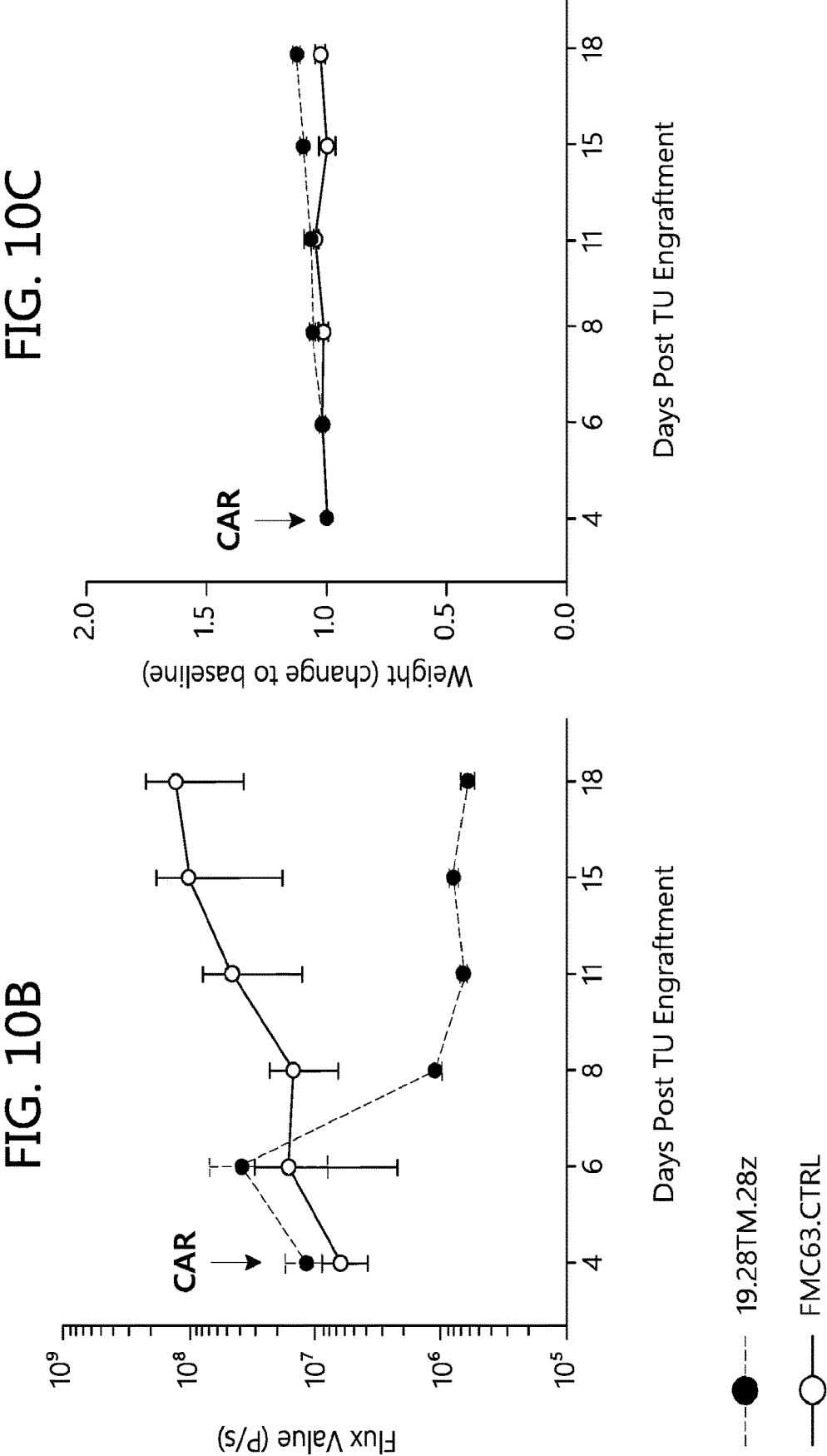

FMC63

28TM.41BBz(**)

28TM.28z (*)

GPC2.19VLVH.8aH-8aTM.41BBz

MLLLVTSLLLCELPHPAFLLIPDIQMTQSPSSLSASIGDRVTITCQASQDISDYLNWYQQKPGKAPKLLIYDASN

CSF2RA signal peptide

19_VL

LETGVPSRFSGSGSGTDFTFTISSLQPEDVATYYCQQYDNLPITFGQGTKLEIKRGGGGSGGGGSGGGGSGGGGSQLQLQ

19_VL linker    19_VL

ESGPGLVKPSETLSLTCTVSGGSISSSSYYWSWIRQPPGKGLEWIGSIYYSGSTYYNPSLKSRVTISVDTSKNQF

19_VL

SLKLSSVTAADTAVYYCARRVSGHPFDPWGQGTLVTVSSATTTPAPRPPTPAPTIASQPLSLRPEACRPAAGGAV

19_VL

CD8a hinge

HTRGLDFACDIYIWAPLAGTCGVLLLSLVITLYCKRGRKKLLYIFKQPFMRPVQTTQEEDGCSCRFPEEEGGCE

CD8a hinge    CD8a transmembrane domain

41BB intracellular domain part of CD8a intracellular domain

LRVKFSRSADAPAYKQGQNQLYNELNLGRREEYDVLDKRRGRDPEMGGKPRRKNPQEGLYNELQKDKMAEAYSEI

CD3 zeta domain

GMKGERRRGKGHDGLYQGLSTATKDTYDALHMQALPPR

CD3 zeta domain

Figure 13:
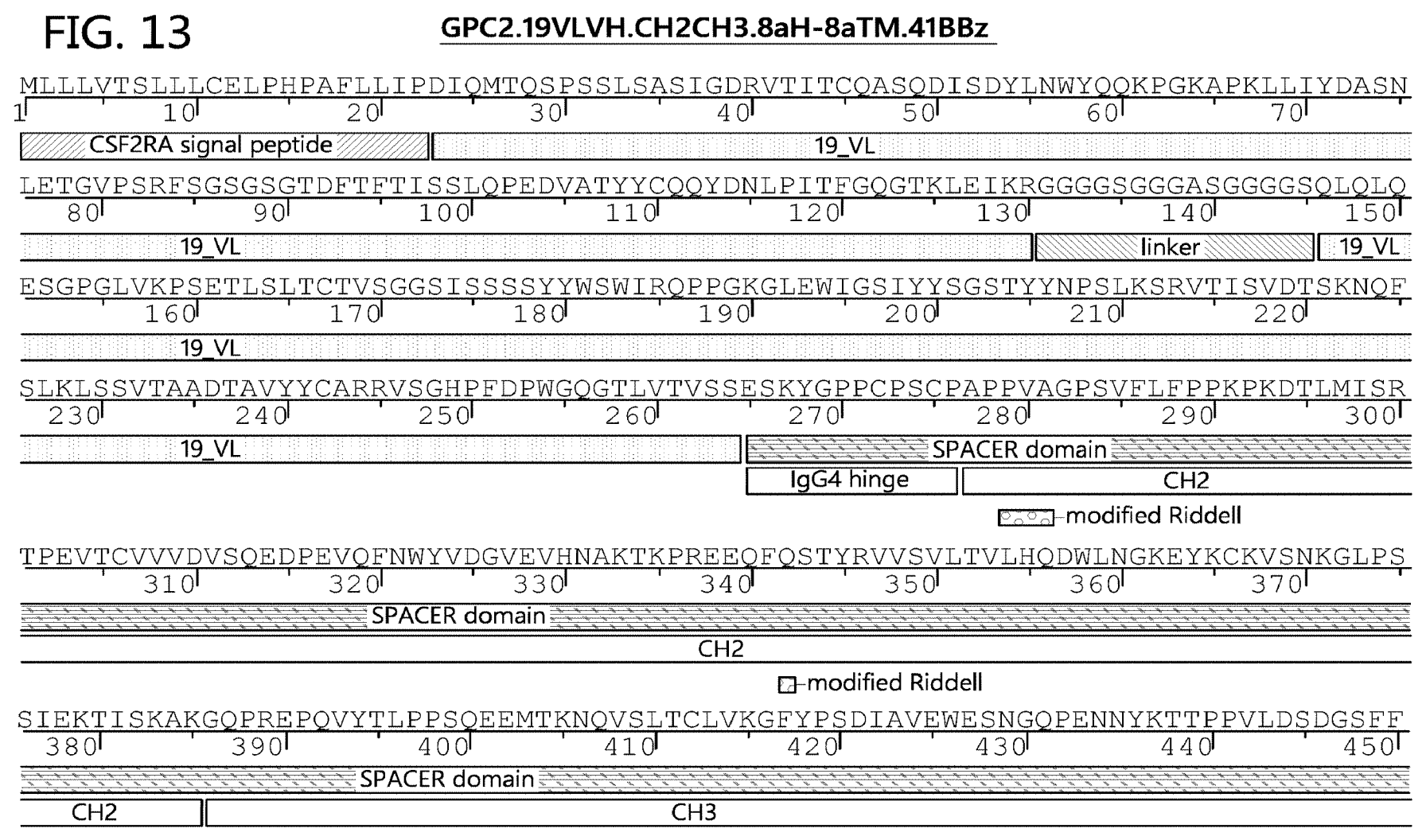

GPC2.19VLVH.CH2CH3.8aH-8aTM.41BBz

MLLLVTSLLLCELPHPAFLLIPDIQMTQSPSSLSASIGDRVTITCQASQDISDYLNWYQQKPGKAPKLLIYDASN
1        10         20        30        40        50        60        70

CSF2RA signal peptide

19_VL

LETGVPSRFSGSGSGTDFTFTISSLQPEDVATYYCQQYDNLPITFGQGTKLEIKRGGGGSGGGGSASGGGGSQLQLQ
        80        90        100        110        120        130        140        150

19_VL                                                                    linker    19_VL ESGPGLVKPSETLSLTCTVSGGSISSSSYYWSWIRQPPGKGLEWIGSIYYSGSTYYNPSLKSRVTISVDTSKNQF
        160        170        180        190        200        210        220

19_VL

SLKLSSVTAADTAVYYCARRVSGHPFDPWGQGTLVTVSSESKYGPPCPSCPAPPVAGPSVFLFPPKPKDTLMISR
        230        240        250        260        270        280        290        300

19_VL              IgG4 hinge                          SPACER domain

CH2 modified Riddell

TPEVTCVVVDVSQEDPEVQFNWYVDGVEVHNAKTKPREEQFQSTYRVVSVLTVLHQDWLNGKEYKCKVSNKGLPS
        310        320        330        340        350        360        370

SPACER domain

CH2 modified Riddell

SIEKTISKAKGQPREPQVYTLPPSQEEMTKNQVSLTCLVKGFYPSDIAVEWESNGQPENNYKTTPPVLDSDGSFF
        380        390        400        410        420        430        440        450

SPACER domain

GPC2.19VLVH.28H-28TM.41BBz

MLLLVTSLLLCELPHPAFLLIPDIQMTQSPSSLSASIGDRVTITCQASQDISDYLNWYQQKPGKAPKLLIYDASN
1           10            20           30           40           50           60           70

*CSF2RA signal peptide*                                   19_VL

LETGVPSRFSGSGSGTDFTFTISSLQPEDVATYYCQQYDNLPITFGQGTKLEIKRGGGGSGGGGSGGGGSGGGGSQLQLQ
        80           90         100         110         120         130         140         150

19_VL                                   *linker*          19_VL

ESGPGLVKPSETLSLTCTVSGGSISSSSYYWSWIRQPPGKGLEWIGSIYYSGSTYYNPSLKSRVTISVDTSKNQF
        160         170         180         190         200         210         220

19_VL

SLKLSSVTAADTAVYYCARRVSGHPFDPWGQGTLVTVSSAAAIEVMYPPPYLDNEKSNGTIIHVKGKHLCPSPLF
        230         240         250         260         270         280         290         300

19_VL                                   *CD28 extracellular hinge domain*
                                    ← Xho cut site PGPSKPFWVLVVVGGVLACYSLLVTVAFIIFWVKRGRKKLLYIFKQPFMRPVQTTQEEDGCSCRFPEEEEGGCEL
        310         320         330         340         350         360         370

*CD28 transmembrane domain*                       *41BB intracellular signaling domain*

RVKFSRSADAPAYKQGQNQLYNELNLGRREEYDVLDKRRGRDPEMGGKPRRKNPQEGLYNELQKDKMAEAYSEIG
        380         390         400         410         420         430         440         450

*CD3 zeta domain*

MKGERRRGKGHDGLYQGLSTATKDTYDALHMQALPPR
        460         470         480     487

*CD3 zeta domain*

FIG. 14

GPC2.19VLVH.28H-28TM.28z

MLLLVTSLLLCELPHPAFLLIPDIQMTQSPSSLSASIGDRVTITCQASQDISDYLNWYQQKPGKAPKLLIYDASN
1                 10                20                30                40                50                60                70
CSF2RA signal peptide                                                                                    19_VL LETGVPSRFSGSGSGTDFTFTISSLQPEDVATYYCQQYDNLPITFGQGTKLEIKRGGGGSGGGGSGGGGSGGGGSQLQLQ
        80                90                100               110               120               130               140      150
                                                                                                        linker    19_VL ESGPGLVKPSETLSLTCTVSGGSISSSSYYWSWIRQPPGKGLEWIGSIYYSGSTYYNPSLKSRVTISVDTSKNQF
        160               170               180               190               200               210               220
19_VL SLKLSSVTAADTAVYYCARRVSGHPFDPWGQGTLVTVSSAAAAIEVMYPPPYLDNEKSNGTIIHVKGKHLCPSPLF
        230               240               250               260               270               280               290       300
19_VL                                                                    CD28 extracellular hinge domain
                                                            Xho cut site PGPSKPFWVLVVVGGVLACYSLLVTVAFIIFWVRSKRSRLLHSDYMNMTPRRPGPTRKHYQPYAPPRDFAAYRSR
        310               320               330               340               350               360               370
CD28 transmembrane domain                                        CD28 intracellular domain VKFSRSADAPAYQQGQNQLYNELNLGRREEYDVLDKRRGRDPEMGGKPRRKNPQEGLYNELQKDKMAEAYSEIGM
        380               390               400               410               420               430               440       450
                                CD3 zeta domain KGERRRGKGHDGLYQGLSTATKDTYDALHMQALPPR
        460               470               480       486
CD3 zeta domain

FIG. 15

SEQUENCE LISTING

```
<160> NUMBER OF SEQ ID NOS: 33

<210> SEQ ID NO 1
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: HCDR1 - scFv.19

<400> SEQUENCE: 1

Gly Gly Ser Ile Ser Ser Ser Ser Tyr Tyr
1               5                   10

<210> SEQ ID NO 2
<211> LENGTH: 8
```

```
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: HCDR2 - scFv.19

<400> SEQUENCE: 2

Ile Tyr Tyr Ser Gly Ser Thr Tyr
1               5

<210> SEQ ID NO 3
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: HCDR3 - scFv.19

<400> SEQUENCE: 3

Ala Arg Arg Val Ser Gly His Pro Phe Asp Pro
1               5                   10

<210> SEQ ID NO 4
<211> LENGTH: 6
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: LCDR1 - scFv.19

<400> SEQUENCE: 4

Gln Asp Ile Ser Asp Tyr
1               5

<210> SEQ ID NO 5
<211> LENGTH: 3
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: LCDR2 - scFv.19

<400> SEQUENCE: 5

Asp Ala Ser
1

<210> SEQ ID NO 6
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: LCDR3 - scFv.19

<400> SEQUENCE: 6

Gln Gln Tyr Asp Asn Leu Pro Ile Thr
1               5

<210> SEQ ID NO 7
```

<211> LENGTH: 119
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: VH - scFv.19

<400> SEQUENCE: 7

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Ser Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Val Ser Gly His Pro Phe Asp Pro Trp Gly Gln Gly
            100                 105                 110

Thr Leu Val Thr Val Ser Ser
        115

<210> SEQ ID NO 8
<211> LENGTH: 108
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: VL- scFv.19

<400> SEQUENCE: 8

Asp Ile Gln Met Thr Gln Ser Pro Ser Ser Leu Ser Ala Ser Ile Gly
1               5                   10                  15

Asp Arg Val Thr Ile Thr Cys Gln Ala Ser Gln Asp Ile Ser Asp Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Ala Thr Tyr Tyr Cys Gln Gln Tyr Asp Asn Leu Pro Ile
                85                  90                  95

Thr Phe Gly Gln Gly Thr Lys Leu Glu Ile Lys Arg
            100                 105

<210> SEQ ID NO 9
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: HCDR1 - scFv.27

```
<400> SEQUENCE: 9

Gly Tyr Ser Ile Ser Ser Gly Tyr Tyr
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: HCDR2 - scFv.27

<400> SEQUENCE: 10

Ile Tyr His Ser Gly Ser Thr Tyr
1               5

<210> SEQ ID NO 11
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: HCDR3 - scFv.27

<400> SEQUENCE: 11

Ala Ser Leu Pro Ser Arg Gly Gly Phe Asp Tyr
1               5                   10

<210> SEQ ID NO 12
<211> LENGTH: 6
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: LCDR1 - scFv.27

<400> SEQUENCE: 12

Gln Thr Ile Ser Arg Tyr
1               5

<210> SEQ ID NO 13
<211> LENGTH: 3
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: LCDR2 - scFv.27

<400> SEQUENCE: 13

Ala Ala Ser
1

<210> SEQ ID NO 14
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
```

<223> OTHER INFORMATION: LCDR3 - scFv.27

<400> SEQUENCE: 14

```
Gln Gln Thr Tyr Ser Pro Pro Ile Thr
1               5
```

<210> SEQ ID NO 15
<211> LENGTH: 118
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: VH - scFv.27

<400> SEQUENCE: 15

```
Glu Val Gln Leu Val Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Leu Pro Ser Arg Gly Gly Phe Asp Tyr Trp Gly Gln Gly Thr
            100                 105                 110

Leu Val Thr Val Ser Ser
        115
```

<210> SEQ ID NO 16
<211> LENGTH: 108
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: VL- scFv.27

<400> SEQUENCE: 16

```
Glu Ile Val Met Thr Gln Ser Pro Ala Thr Leu Ser Ala Ser Val Gly
1               5                   10                  15

Asp Arg Val Thr Ile Ala Cys Arg Ala Ser Gln Thr Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Ser Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Thr Tyr Ser Pro Pro Ile
                85                  90                  95

Thr Phe Gly Gln Gly Thr Arg Leu Glu Ile Lys Arg
            100                 105
```

```
<210> SEQ ID NO 17
<211> LENGTH: 488
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: 19VLVH.8aH-8aTM.41BBz

<400> SEQUENCE: 17

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Ile Gly Asp Arg Val Thr Ile Thr Cys Gln Ala Ser
        35                  40                  45

Gln Asp Ile Ser Asp Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Val Ala Thr Tyr Tyr Cys Gln Gln
            100                 105                 110

Tyr Asp Asn Leu Pro Ile Thr Phe Gly Gln Gly Thr Lys Leu Glu Ile
            115                 120                 125

Lys Arg Gly Gly Gly Gly Ser Gly Gly Gly Ala Ser Gly Gly Gly Gly
    130                 135                 140

Ser Gln Leu Gln Leu Gln Glu Ser Gly Pro Gly Leu Val Lys Pro Ser
145                 150                 155                 160

Glu Thr Leu Ser Leu Thr Cys Thr Val Ser Gly Gly Ser Ile Ser Ser
                165                 170                 175

Ser Ser Tyr Tyr Trp Ser Trp Ile Arg Gln Pro Pro Gly Lys Gly Leu
            180                 185                 190

Glu Trp Ile Gly Ser Ile Tyr Tyr Ser Gly Ser Thr Tyr Tyr Asn Pro
            195                 200                 205

Ser Leu Lys Ser Arg Val Thr Ile Ser Val Asp Thr Ser Lys Asn Gln
    210                 215                 220

Phe Ser Leu Lys Leu Ser Ser Val Thr Ala Ala Asp Thr Ala Val Tyr
225                 230                 235                 240

Tyr Cys Ala Arg Arg Val Ser Gly His Pro Phe Asp Pro Trp Gly Gln
                245                 250                 255

Gly Thr Leu Val Thr Val Ser Ser Ala Thr Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350
```

```
Val Gln Thr Thr Gln Glu Glu Asp Gly Cys Ser Cys Arg Phe Pro Glu
        355             360             365

Glu Glu Glu Gly Gly Cys Glu Leu Arg Val Lys Phe Ser Arg Ser Ala
        370             375             380

Asp Ala Pro Ala Tyr Lys Gln Gly Gln Asn Gln Leu Tyr Asn Glu Leu
385             390             395             400

Asn Leu Gly Arg Arg Glu Glu Tyr Asp Val Leu Asp Lys Arg Arg Gly
                405             410             415

Arg Asp Pro Glu Met Gly Gly Lys Pro Arg Arg Lys Asn Pro Gln Glu
                420             425             430

Gly Leu Tyr Asn Glu Leu Gln Lys Asp Lys Met Ala Glu Ala Tyr Ser
        435             440             445

Glu Ile Gly Met Lys Gly Glu Arg Arg Arg Gly Lys Gly His Asp Gly
        450             455             460

Leu Tyr Gln Gly Leu Ser Thr Ala Thr Lys Asp Thr Tyr Asp Ala Leu
465             470             475             480

His Met Gln Ala Leu Pro Pro Arg
                485
```

```
<210> SEQ ID NO 18
<211> LENGTH: 488
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: 19VLVH.CH2CH3.8aH-8aTM.41BBz

<400> SEQUENCE: 18
```

```
Met Leu Leu Leu Val Thr Ser Leu Leu Leu Cys Glu Leu Pro His Pro
1               5               10              15

Ala Phe Leu Leu Ile Pro Asp Ile Gln Met Thr Gln Ser Pro Ser Ser
        20              25              30

Leu Ser Ala Ser Ile Gly Asp Arg Val Thr Ile Thr Cys Gln Ala Ser
        35              40              45

Gln Asp Ile Ser Asp Tyr Leu Asn Trp Tyr Gln Gln Lys Pro Gly Lys
    50              55              60

Ala Pro Lys Leu Leu Ile Tyr Asp Ala Ser Asn Leu Glu Thr Gly Val
65              70              75              80

Pro Ser Arg Phe Ser Gly Ser Gly Ser Gly Thr Asp Phe Thr Phe Thr
                85              90              95

Ile Ser Ser Leu Gln Pro Glu Asp Val Ala Thr Tyr Tyr Cys Gln Gln
        100             105             110

Tyr Asp Asn Leu Pro Ile Thr Phe Gly Gln Gly Thr Lys Leu Glu Ile
        115             120             125

Lys Arg Gly Gly Gly Gly Ser Gly Gly Gly Ala Ser Gly Gly Gly Gly
        130             135             140

Ser Gln Leu Gln Leu Gln Glu Ser Gly Pro Gly Leu Val Lys Pro Ser
145             150             155             160

Glu Thr Leu Ser Leu Thr Cys Thr Val Ser Gly Gly Ser Ile Ser Ser
                165             170             175

Ser Ser Tyr Tyr Trp Ser Trp Ile Arg Gln Pro Pro Gly Lys Gly Leu
        180             185             190

Glu Trp Ile Gly Ser Ile Tyr Tyr Ser Gly Ser Thr Tyr Tyr Asn Pro
        195             200             205
```

```
Ser Leu Lys Ser Arg Val Thr Ile Ser Val Asp Thr Ser Lys Asn Gln
    210             215             220
```

```
Phe Ser Leu Lys Leu Ser Ser Val Thr Ala Ala Asp Thr Ala Val Tyr
225             230             235             240
```

```
Tyr Cys Ala Arg Arg Val Ser Gly His Pro Phe Asp Pro Trp Gly Gln
            245             250             255
```

```
Gly Thr Leu Val Thr Val Ser Ser Ala Thr Thr Thr Pro Ala Pro Arg
            260             265             270
```

```
Pro Pro Thr Pro Ala Pro Thr Ile Ala Ser Gln Pro Leu Ser Leu Arg
        275             280             285
```

```
Pro Glu Ala Cys Arg Pro Ala Ala Gly Gly Ala Val His Thr Arg Gly
    290             295             300
```

```
Leu Asp Phe Ala Cys Asp Ile Tyr Ile Trp Ala Pro Leu Ala Gly Thr
305             310             315             320
```

```
Cys Gly Val Leu Leu Leu Ser Leu Val Ile Thr Leu Tyr Cys Lys Arg
            325             330             335
```

```
Gly Arg Lys Lys Leu Leu Tyr Ile Phe Lys Gln Pro Phe Met Arg Pro
            340             345             350
```

```
Val Gln Thr Thr Gln Glu Glu Asp Gly Cys Ser Cys Arg Phe Pro Glu
        355             360             365
```

```
Glu Glu Glu Gly Gly Cys Glu Leu Arg Val Lys Phe Ser Arg Ser Ala
    370             375             380
```

```
Asp Ala Pro Ala Tyr Lys Gln Gly Gln Asn Gln Leu Tyr Asn Glu Leu
385             390             395             400
```

```
Asn Leu Gly Arg Arg Glu Glu Tyr Asp Val Leu Asp Lys Arg Arg Gly
            405             410             415
```

```
Arg Asp Pro Glu Met Gly Gly Lys Pro Arg Arg Lys Asn Pro Gln Glu
            420             425             430
```

```
Gly Leu Tyr Asn Glu Leu Gln Lys Asp Lys Met Ala Glu Ala Tyr Ser
            435             440             445
```

```
Glu Ile Gly Met Lys Gly Glu Arg Arg Arg Gly Lys Gly His Asp Gly
    450             455             460
```

```
Leu Tyr Gln Gly Leu Ser Thr Ala Thr Lys Asp Thr Tyr Asp Ala Leu
465             470             475             480
```

```
His Met Gln Ala Leu Pro Pro Arg
            485
```

```
<210> SEQ ID NO 19
<211> LENGTH: 487
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: 19.VLVH.28TM.41BBz

<400> SEQUENCE: 19
```

```
Met Leu Leu Leu Val Thr Ser Leu Leu Leu Cys Glu Leu Pro His Pro
1               5               10              15
```

```
Ala Phe Leu Leu Ile Pro Asp Ile Gln Met Thr Gln Ser Pro Ser Ser
            20              25              30
```

```
Leu Ser Ala Ser Ile Gly Asp Arg Val Thr Ile Thr Cys Gln Ala Ser
        35              40              45
```

```
Gln Asp Ile Ser Asp Tyr Leu Asn Trp Tyr Gln Gln Lys Pro Gly Lys
    50              55              60
```

-continued

```
Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Val Ala Thr Tyr Tyr Cys Gln Gln
              100                 105                 110

Tyr Asp Asn Leu Pro Ile Thr Phe Gly Gln Gly Thr Lys Leu Glu Ile
              115                 120                 125

Lys Arg Gly Gly Gly Ser Gly Gly Gly Ala Ser Gly Gly Gly Gly
          130                 135                 140

Ser Gln Leu Gln Leu Gln Glu Ser Gly Pro Gly Leu Val Lys Pro Ser
145                 150                 155                 160

Glu Thr Leu Ser Leu Thr Cys Thr Val Ser Gly Gly Ser Ile Ser Ser
              165                 170                 175

Ser Ser Tyr Tyr Trp Ser Trp Ile Arg Gln Pro Pro Gly Lys Gly Leu
              180                 185                 190

Glu Trp Ile Gly Ser Ile Tyr Tyr Ser Gly Ser Thr Tyr Tyr Asn Pro
              195                 200                 205

Ser Leu Lys Ser Arg Val Thr Ile Ser Val Asp Thr Ser Lys Asn Gln
          210                 215                 220

Phe Ser Leu Lys Leu Ser Ser Val Thr Ala Ala Asp Thr Ala Val Tyr
225                 230                 235                 240

Tyr Cys Ala Arg Arg Val Ser Gly His Pro Phe Asp Pro Trp Gly Gln
              245                 250                 255

Gly Thr Leu Val Thr Val Ser Ser Ala Ala Ile Glu Val Met Tyr
              260                 265                 270

Pro Pro Pro Tyr Leu Asp Asn Glu Lys Ser Asn Gly Thr Ile Ile His
              275                 280                 285

Val Lys Gly Lys His Leu Cys Pro Ser Pro Leu Phe Pro Gly Pro Ser
          290                 295                 300

Lys Pro Phe Trp Val Leu Val Val Val Gly Gly Val Leu Ala Cys Tyr
305                 310                 315                 320

Ser Leu Leu Val Thr Val Ala Phe Ile Ile Phe Trp Val Lys Arg Gly
              325                 330                 335

Arg Lys Lys Leu Leu Tyr Ile Phe Lys Gln Pro Phe Met Arg Pro Val
              340                 345                 350

Gln Thr Thr Gln Glu Glu Asp Gly Cys Ser Cys Arg Phe Pro Glu Glu
              355                 360                 365

Glu Glu Gly Gly Cys Glu Leu Arg Val Lys Phe Ser Arg Ser Ala Asp
          370                 375                 380

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
              405                 410                 415

Asp Pro Glu Met Gly Gly Lys Pro Arg Arg Lys Asn Pro Gln Glu Gly
              420                 425                 430

Leu Tyr Asn Glu Leu Gln Lys Asp Lys Met Ala Glu Ala Tyr Ser Glu
              435                 440                 445

Ile Gly Met Lys Gly Glu Arg Arg Arg Gly Lys Gly His Asp Gly Leu
          450                 455                 460

Tyr Gln Gly Leu Ser Thr Ala Thr Lys Asp Thr Tyr Asp Ala Leu His
465                 470                 475                 480
```

Met Gln Ala Leu Pro Pro Arg
                485

<210> SEQ ID NO 20
<211> LENGTH: 486
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: 19VLVH.28TM.28z

<400> SEQUENCE: 20

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Ile Gly Asp Arg Val Thr Ile Thr Cys Gln Ala Ser
        35                  40                  45

Gln Asp Ile Ser Asp Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Val Ala Thr Tyr Tyr Cys Gln Gln
            100                 105                 110

Tyr Asp Asn Leu Pro Ile Thr Phe Gly Gln Gly Thr Lys Leu Glu Ile
            115                 120                 125

Lys Arg Gly Gly Gly Gly Ser Gly Gly Gly Ala Ser Gly Gly Gly Gly
        130                 135                 140

Ser Gln Leu Gln Leu Gln Glu Ser Gly Pro Gly Leu Val Lys Pro Ser
145                 150                 155                 160

Glu Thr Leu Ser Leu Thr Cys Thr Val Ser Gly Gly Ser Ile Ser Ser
                165                 170                 175

Ser Ser Tyr Tyr Trp Ser Trp Ile Arg Gln Pro Pro Gly Lys Gly Leu
            180                 185                 190

Glu Trp Ile Gly Ser Ile Tyr Tyr Ser Gly Ser Thr Tyr Tyr Asn Pro
        195                 200                 205

Ser Leu Lys Ser Arg Val Thr Ile Ser Val Asp Thr Ser Lys Asn Gln
    210                 215                 220

Phe Ser Leu Lys Leu Ser Ser Val Thr Ala Ala Asp Thr Ala Val Tyr
225                 230                 235                 240

Tyr Cys Ala Arg Arg Val Ser Gly His Pro Phe Asp Pro Trp Gly Gln
            245                 250                 255

Gly Thr Leu Val Thr Val Ser Ser Ala Ala Ala Ile Glu Val Met Tyr
            260                 265                 270

Pro Pro Pro Tyr Leu Asp Asn Glu Lys Ser Asn Gly Thr Ile Ile His
        275                 280                 285

Val Lys Gly Lys His Leu Cys Pro Ser Pro Leu Phe Pro Gly Pro Ser
    290                 295                 300

Lys Pro Phe Trp Val Leu Val Val Val Gly Gly Val Leu Ala Cys Tyr
305                 310                 315                 320

Ser Leu Leu Val Thr Val Ala Phe Ile Ile Phe Trp Val Arg Ser Lys
            325                 330                 335

-continued

```
Arg Ser Arg Leu Leu His Ser Asp Tyr Met Asn Met Thr Pro Arg Arg
            340             345             350

Pro Gly Pro Thr Arg Lys His Tyr Gln Pro Tyr Ala Pro Pro Arg Asp
        355             360             365

Phe Ala Ala Tyr Arg Ser Arg Val Lys Phe Ser Arg Ser Ala Asp Ala
    370             375             380

Pro Ala Tyr Gln Gln Gly Gln Asn Gln Leu Tyr Asn Glu Leu Asn Leu
385             390             395             400

Gly Arg Arg Glu Glu Tyr Asp Val Leu Asp Lys Arg Arg Gly Arg Asp
            405             410             415

Pro Glu Met Gly Gly Lys Pro Arg Arg Lys Asn Pro Gln Glu Gly Leu
        420             425             430

Tyr Asn Glu Leu Gln Lys Asp Lys Met Ala Glu Ala Tyr Ser Glu Ile
        435             440             445

Gly Met Lys Gly Glu Arg Arg Arg Gly Lys Gly His Asp Gly Leu Tyr
    450             455             460

Gln Gly Leu Ser Thr Ala Thr Lys Asp Thr Tyr Asp Ala Leu His Met
465             470             475             480

Gln Ala Leu Pro Pro Arg
            485
```

<210> SEQ ID NO 21
<211> LENGTH: 242
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: GPC2.19 (VH-linker-VL)_amino acid

<400> SEQUENCE: 21

```
Gln Leu Gln Leu Gln Glu Ser Gly Pro Gly Leu Val Lys Pro Ser Glu
1               5               10              15

Thr Leu Ser Leu Thr Cys Thr Val Ser Gly Gly Ser Ile Ser Ser Ser
            20              25              30

Ser Tyr Tyr Trp Ser Trp Ile Arg Gln Pro Pro Gly Lys Gly Leu Glu
        35              40              45

Trp Ile Gly Ser Ile Tyr Tyr Ser Gly Ser Thr Tyr Tyr Asn Pro Ser
    50              55              60

Leu Lys Ser Arg Val Thr Ile Ser Val Asp Thr Ser Lys Asn Gln Phe
65              70              75              80

Ser Leu Lys Leu Ser Ser Val Thr Ala Ala Asp Thr Ala Val Tyr Tyr
            85              90              95

Cys Ala Arg Arg Val Ser Gly His Pro Phe Asp Pro Trp Gly Gln Gly
            100             105             110

Thr Leu Val Thr Val Ser Ser Gly Gly Gly Gly Ser Gly Gly Gly Ala
        115             120             125

Ser Gly Gly Gly Gly Ser Asp Ile Gln Met Thr Gln Ser Pro Ser Ser
    130             135             140

Leu Ser Ala Ser Ile Gly Asp Arg Val Thr Ile Thr Cys Gln Ala Ser
145             150             155             160

Gln Asp Ile Ser Asp Tyr Leu Asn Trp Tyr Gln Gln Lys Pro Gly Lys
            165             170             175

Ala Pro Lys Leu Leu Ile Tyr Asp Ala Ser Asn Leu Glu Thr Gly Val
        180             185             190
```

-continued

```
Pro Ser Arg Phe Ser Gly Ser Gly Ser Gly Thr Asp Phe Thr Phe Thr
        195                 200                 205

Ile Ser Ser Leu Gln Pro Glu Asp Val Ala Thr Tyr Tyr Cys Gln Gln
    210                 215                 220

Tyr Asp Asn Leu Pro Ile Thr Phe Gly Gln Gly Thr Lys Leu Glu Ile
225                 230                 235                 240

Lys Arg

<210> SEQ ID NO 22
<211> LENGTH: 241
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: GPC2.27 (VH-linker-VL) amino acid

<400> SEQUENCE: 22

Glu Val Gln Leu Val Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Leu Pro Ser Arg Gly Gly Phe Asp Tyr Trp Gly Gln Gly Thr
            100                 105                 110

Leu Val Thr Val Ser Ser Gly Gly Gly Gly Ser Gly Gly Gly Ala Ser
            115                 120                 125

Gly Gly Gly Gly Ser Glu Ile Val Met Thr Gln Ser Pro Ala Thr Leu
        130                 135                 140

Ser Ala Ser Val Gly Asp Arg Val Thr Ile Ala Cys Arg Ala Ser Gln
145                 150                 155                 160

Thr Ile Ser Arg Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Ser
            180                 185                 190

Ser Arg Phe Ser Gly Ser Gly Ser Gly Thr Glu Phe Thr Leu Thr Ile
        195                 200                 205

Ser Ser Leu Gln Pro Glu Asp Phe Ala Thr Tyr Phe Cys Gln Gln Thr
    210                 215                 220

Tyr Ser Pro Pro Ile Thr Phe Gly Gln Gly Thr Arg Leu Glu Ile Lys
225                 230                 235                 240

Arg

<210> SEQ ID NO 23
<211> LENGTH: 488
<212> TYPE: PRT
<213> ORGANISM: Artificial sequence
<220> FEATURE:
<223> OTHER INFORMATION: Synthetic construct
<220> FEATURE:
```

-continued

```
<221> NAME/KEY: MISC_FEATURE
<223> OTHER INFORMATION: 19VHVL.8aH-8aTM.41BBz

<400> SEQUENCE: 23

Met Leu Leu Leu Val Thr Ser Leu Leu Leu Cys Glu Leu Pro His Pro
1               5                   10                  15

Ala Phe Leu Leu Ile Pro Gln Leu Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Gly Ser Ile Ser Ser Ser Ser Tyr Tyr Trp Ser Trp Ile Arg Gln Pro
    50                  55                  60

Pro Gly Lys Gly Leu Glu Trp Ile Gly Ser Ile Tyr Tyr Ser Gly Ser
65                  70                  75                  80

Thr Tyr Tyr Asn Pro Ser Leu Lys Ser Arg Val Thr Ile Ser Val Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Arg Arg Val Ser Gly His Pro Phe
        115                 120                 125

Asp Pro Trp Gly Gln Gly Thr Leu Val Thr Val Ser Ser Gly Gly Gly
        130                 135                 140

Gly Ser Gly Gly Gly Ala Ser Gly Gly Gly Ser Asp Ile Gln Met
145                 150                 155                 160

Thr Gln Ser Pro Ser Ser Leu Ser Ala Ser Ile Gly Asp Arg Val Thr
                165                 170                 175

Ile Thr Cys Gln Ala Ser Gln Asp Ile Ser Asp Tyr Leu Asn Trp Tyr
            180                 185                 190

Gln Gln Lys Pro Gly Lys Ala Pro Lys Leu Leu Ile Tyr Asp Ala Ser
            195                 200                 205

Asn Leu Glu Thr Gly Val Pro Ser Arg Phe Ser Gly Ser Gly Ser Gly
        210                 215                 220

Thr Asp Phe Thr Phe Thr Ile Ser Ser Leu Gln Pro Glu Asp Val Ala
225                 230                 235                 240

Thr Tyr Tyr Cys Gln Gln Tyr Asp Asn Leu Pro Ile Thr Phe Gly Gln
                245                 250                 255

Gly Thr Lys Leu Glu Ile Lys Arg Ala Thr Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
        290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
        370                 375                 380

Asp Ala Pro Ala Tyr Lys Gln Gly Gln Asn Gln Leu Tyr Asn Glu Leu
385                 390                 395                 400
```

-continued

```
Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
                420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
        450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 24
<211> LENGTH: 487
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: 27VLVH.8aH-8aTM.41BBz

<400> SEQUENCE: 24

Met Leu Leu Leu Val Thr Ser Leu Leu Leu Cys Glu Leu Pro His Pro
1               5                   10                  15

Ala Phe Leu Leu Ile Pro Glu Ile Val Met Thr Gln Ser Pro Ala Thr
            20                  25                  30

Leu Ser Ala Ser Val Gly Asp Arg Val Thr Ile Ala Cys Arg Ala Ser
            35                  40                  45

Gln Thr Ile Ser Arg Tyr Leu Asn Trp Tyr Gln Gln Lys Pro Gly Lys
        50                  55                  60

Ala Pro Lys Leu Leu Ile Tyr Ala Ala Ser Ser Leu Gln Ser Gly Val
65                  70                  75                  80

Ser Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Phe Cys Gln Gln
            100                 105                 110

Thr Tyr Ser Pro Pro Ile Thr Phe Gly Gln Gly Thr Arg Leu Glu Ile
            115                 120                 125

Lys Arg Gly Gly Gly Gly Ser Gly Gly Gly Ala Ser Gly Gly Gly Gly
        130                 135                 140

Ser Glu Val Gln Leu Val Glu Ser Gly Pro Gly Leu Val Lys Pro Ser
145                 150                 155                 160

Glu Thr Leu Ser Leu Thr Cys Ala Val Ser Gly Tyr Ser Ile Ser Ser
                165                 170                 175

Gly Tyr Tyr Trp Gly Trp Ile Arg Gln Pro Pro Gly Lys Gly Leu Glu
            180                 185                 190

Trp Ile Gly Ser Ile Tyr His Ser Gly Ser Thr Tyr Tyr Asn Pro Ser
            195                 200                 205

Leu Lys Ser Arg Val Thr Ile Ser Val Asp Thr Ser Lys Asn Gln Phe
        210                 215                 220

Ser Leu Lys Leu Ser Ser Val Thr Ala Ala Asp Thr Ala Val Tyr Tyr
225                 230                 235                 240

Cys Ala Ser Leu Pro Ser Arg Gly Gly Phe Asp Tyr Trp Gly Gln Gly
            245                 250                 255
```

Thr Leu Val Thr Val Ser Ser Ala Thr Thr Thr Pro Ala Pro Arg Pro
                260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
        290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
                340                 345                 350

Gln Thr Thr Gln Glu Glu Asp Gly Cys Ser Cys Arg Phe Pro Glu Glu
                355                 360                 365

Glu Glu Gly Gly Cys Glu Leu Arg Val Lys Phe Ser Arg Ser Ala Asp
        370                 375                 380

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
        450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 25
<211> LENGTH: 487
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: 27VHVL.8aH-8aTM.41BBz

<400> SEQUENCE: 25

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Pro Gly
        20                  25                  30

Leu Val Lys Pro Ser Glu Thr Leu Ser Leu Thr Cys Ala Val Ser Gly
        35                  40                  45

Tyr Ser Ile Ser Ser Gly Tyr Tyr Trp Gly Trp Ile Arg Gln Pro Pro
        50                  55                  60

Gly Lys Gly Leu Glu Trp Ile Gly Ser Ile Tyr His Ser Gly Ser Thr
65                  70                  75                  80

Tyr Tyr Asn Pro Ser Leu Lys Ser Arg Val Thr Ile Ser Val Asp Thr
                85                  90                  95

Ser Lys Asn Gln Phe Ser Leu Lys Leu Ser Ser Val Thr Ala Ala Asp
                100                 105                 110

-continued

```
Thr Ala Val Tyr Tyr Cys Ala Ser Leu Pro Ser Arg Gly Gly Phe Asp
        115                 120                 125

Tyr Trp Gly Gln Gly Thr Leu Val Thr Val Ser Ser Gly Gly Gly Gly
        130                 135                 140

Ser Gly Gly Gly Ala Ser Gly Gly Gly Gly Ser Glu Ile Val Met Thr
145                 150                 155                 160

Gln Ser Pro Ala Thr Leu Ser Ala Ser Val Gly Asp Arg Val Thr Ile
                165                 170                 175

Ala Cys Arg Ala Ser Gln Thr Ile Ser Arg Tyr Leu Asn Trp Tyr Gln
                180                 185                 190

Gln Lys Pro Gly Lys Ala Pro Lys Leu Leu Ile Tyr Ala Ala Ser Ser
                195                 200                 205

Leu Gln Ser Gly Val Ser Ser Arg Phe Ser Gly Ser Gly Ser Gly Thr
        210                 215                 220

Glu Phe Thr Leu Thr Ile Ser Ser Leu Gln Pro Glu Asp Phe Ala Thr
225                 230                 235                 240

Tyr Phe Cys Gln Gln Thr Tyr Ser Pro Pro Ile Thr Phe Gly Gln Gly
                245                 250                 255

Thr Arg Leu Glu Ile Lys Arg Ala Thr Thr Thr Pro Ala Pro Arg Pro
        260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
        290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
        340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
        370                 375                 380

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
        450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485
```

<210> SEQ ID NO 26
<211> LENGTH: 1467
<212> TYPE: DNA
<213> ORGANISM: Artificial sequence
<220> FEATURE:

<223> OTHER INFORMATION: Synthetic construct
<220> FEATURE:
<221> NAME/KEY: misc_feature
<223> OTHER INFORMATION: encodes the polypeptide of SEQ ID NO:17
<220> FEATURE:
<221> NAME/KEY: misc_feature
<223> OTHER INFORMATION: 19VLVH.8aH-8aTM.41BBz

<400> SEQUENCE: 26

```
atgcttctcc tggtgacaag ccttctgctc tgtgagttac cacacccagc attcctcctg      60
atcccagaca tccagatgac ccagtctcca tcctccctgt ctgcatctat aggagacaga     120
gtcaccatca cttgccaggc gagtcaggac attagcgact atttaaattg gtatcagcag     180
aaaccaggga aagcccctaa gctcctgatc tacgatgcat ccaatttgga gactggggtc     240
ccatcaaggt tcagtggaag tggatctggg acagatttta ctttcaccat cagcagcctc     300
cagcctgaag atgttgcaac atattactgt caacagtatg ataatctccc gatcaccttc     360
ggccaaggga ccaagctgga aatcaaacgt ggaggtggcg gtctggtgg aggcgctagc      420 ggtggtggcg gatcccagct gcagctgcag agtcgggcc caggactggt gaagccttcg      480
gagaccctgt ccctcacctg cactgtctct ggtggctcca tcagcagtag tagttactac     540
tggagctgga tccgccagcc cccagggaag gggctggagt ggattgggag tatctattat     600
agtgggagca cctactacaa cccgtccctc aagagtcgag tcaccatatc agtagacacg     660
tccaagaacc agttctccct gaagctgagc tctgtgaccg ccgcggacac ggccgtgtat     720
tactgtgcga cgggtcag tggccacccc ttcgacccct ggggccaggg aaccctggtc      780
accgtctcct cagcaaccac gacgccagcg ccgcgaccac caacaccggc gcccaccatc     840
gcgtcgcagc ccctgtccct gcgcccagag gcgtgccggc cagcggcggg gggcgcagtg     900
cacacgaggg ggctggactt cgcctgtgat atctacatct gggcgccctt ggccgggact     960
tgtggggtcc ttctcctgtc actggttatc acccttact gcaaacgggg cagaaagaaa     1020
ctcctgtata tattcaaaca accatttatg agaccagtac aaactactca agaggaagat    1080
ggctgtagct gccgatttcc agaagaagaa gaaggaggat gtgaactgag agtgaagttc    1140
agcaggagcg cagacgcccc cgcgtacaag cagggccaga accagctcta taacgagctc    1200
aatctaggac gaagagagga gtacgatgtt ttggacaaga cgtggccg ggaccctgag     1260 atggggggaa agccgagaag gaagaaccct caggaaggcc tgtacaatga actgcagaaa    1320
gataagatgg cggaggccta cagtgagatt gggatgaaag gcgagcgccg gaggggcaag    1380
gggcacgatg gcctttacca gggtctcagt acagccacca aggacaccta cgacgccctt    1440
cacatgcagg ccctgccccc tcgctaa                                        1467
```

<210> SEQ ID NO 27
<211> LENGTH: 2160
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: encodes the polypeptide of SEQ ID NO:18
<220> FEATURE:
<221> NAME/KEY: misc_feature
<223> OTHER INFORMATION: 19VLVH.CH2CH3.8aH-8aTM.41BBz

<400> SEQUENCE: 27

```
atgcttctcc tggtgacaag ccttctgctc tgtgagttac cacacccagc attcctcctg      60
atcccagaca tccagatgac ccagtctcca tcctccctgt ctgcatctat aggagacaga     120
```

-continued

```
gtcaccatca cttgccaggc gagtcaggac attagcgact atttaaattg gtatcagcag        180
aaaccaggga aagcccctaa gctcctgatc tacgatgcat ccaatttgga gactgggtc         240 ccatcaaggt tcagtggaag tggatctggg acagatttta ctttcaccat cagcagcctc        300
cagcctgaag atgttgcaac atattactgt caacagtatg ataatctccc gatcaccttc        360
ggccaaggga ccaagctgga aatcaaacgt ggaggtggcg ggtctggtgg aggcgctagc        420
ggtggtggcg gatcccagct gcagctgcag gagtcgggcc caggactggt gaagccttcg        480
gagaccctgt ccctcacctg cactgtctct ggtggctcca tcagcagtag tagttactac        540
tggagctgga tccgccagcc cccagggaag gggctggagt ggattgggag tatctattat        600
agtgggagca cctactacaa cccgtccctc aagagtcgag tcaccatatc agtagacacg        660
tccaagaacc agttctccct gaagctgagc tctgtgaccg ccgcggacac ggccgtgtat        720
tactgtgcga cacgggtcag tggccacccc ttcgacccct ggggccaggg aaccctggtc        780
accgtctcct cagagtccaa atatggtccc ccatgcccat catgcccagc acctccggtc        840
gcgggaccat cagtcttcct gttcccccca aaacccaagg acactctcat gatctcccgg        900
acccctgagg tcacgtgcgt ggtggtggac gtgagccagg aagaccccga ggtccagttc        960
aactggtacg tggatggcgt ggaggtgcat aatgccaaga caaagccgcg ggaggagcag       1020
ttccaaagca cgtaccgtgt ggtcagcgtc ctcaccgtcc tgcaccagga ctggctgaac       1080
ggcaaggagt acaagtgcaa ggtctccaac aaaggcctcc cgtcctccat cgagaaaacc       1140
atctccaaag ccaaagggca gccccgagag ccacaggtgt acaccctgcc cccatcccag       1200
gaggagatga ccaagaacca ggtcagcctg acctgcctgg tcaaaggctt ctaccccagc       1260
gacatcgccg tggagtggga gagcaatggg cagccggaga caactacaa gaccacgcct        1320 cccgtgctgg actccgacgg ctccttcttc ctctacagca ggctcaccgt ggacaagagc       1380
aggtggcagg aggggaatgt cttctcatgc tccgtgatgc atgaggctct gcacaaccac       1440
tacacacaga agagcctctc cctgtctctg ggtaaatcgg cggccgcaac cacgacgcca       1500
gcgccgcgac caccaacacc ggcgcccacc atcgcgtcgc agcccctgtc cctgcgccca       1560
gaggcgtgcc ggccagcggc gggggcgca gtgcacacga gggggctgga cttcgcctgt        1620
gatatctaca tctgggcgcc cttggccggg acttgtgggg tccttctcct gtcactggtt       1680
atcacccttt actgcaaacg gggcagaaag aaactcctgt atatattcaa acaaccattt       1740
atgagaccag tacaaactac tcaagaggaa gatggctgta gctgccgatt tccagaagaa       1800
gaagaaggag gatgtgaact gagagtgaag ttcagcagga gcgcagacgc ccccgcgtac       1860
aagcagggcc agaaccagct ctataacgag ctcaatctag acgaagaga ggagtacgat        1920 gttttggaca gagacgtgg ccgggaccct gagatggggg gaaagccgag aaggaagaac        1980
cctcaggaag gcctgtacaa tgaactgcag aaagataaga tggcggaggc ctacagtgag       2040
attgggatga aggcgagcg ccggaggggc aaggggcacg atggccttta ccagggtctc        2100
agtacagcca ccaaggacac ctacgacgcc cttcacatgc aggccctgcc ccctcgctaa       2160
```

```
<210> SEQ ID NO 28
<211> LENGTH: 1464
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: encodes the polypeptide of SEQ ID NO:19
```

```
<220> FEATURE:
<221> NAME/KEY: misc_feature
<223> OTHER INFORMATION: 19.VLVH.28TM.41BBz

<400> SEQUENCE: 28
atgcttctcc tggtgacaag ccttctgctc tgtgagttac cacacccagc attcctcctg    60
atcccagaca tccagatgac ccagtctcca tcctccctgt ctgcatctat aggagacaga   120
gtcaccatca cttgccaggc gagtcaggac attagcgact atttaaattg gtatcagcag   180
aaaccaggga aagcccctaa gctcctgatc tacgatgcat ccaatttgga gactggggtc   240
ccatcaaggt tcagtggaag tggatctggg acagatttta ctttcaccat cagcagcctc   300
cagcctgaag atgttgcaac atattactgt caacagtatg ataatctccc gatcaccttc   360
ggccaaggga ccaagctgga aatcaaacgt ggaggtggcg gtctggtgg aggcgctagc    420 ggtggtggcg gatcccagct gcagctgcag gagtcgggcc caggactggt gaagccttcg   480
gagaccctgt ccctcacctg cactgtctct ggtggctcca tcagcagtag tagttactac   540
tggagctgga tccgccagcc cccagggaag gggctggagt ggattgggag tatctattat   600
agtgggagca cctactacaa cccgtccctc aagagtcgag tcaccatatc agtagacacg   660
tccaagaacc agttctccct gaagctgagc tctgtgaccg ccgcggacac ggccgtgtat   720
tactgtgcga cacgggtcag tggccacccc ttcgacccct ggggccaggg aaccctggtc   780
accgtctcct cagcggccgc aattgaagtt atgtatcctc ctccttacct agacaatgag   840
aagagcaatg gaaccattat ccatgtgaaa gggaaacacc tttgtccaag tcccctatttt  900 cccggacctt ctaagccctt ttgggtgctg gtggtggttg ggggagtcct ggcttgctat   960
agcttgctag taacagtggc ctttattatt ttctgggtga acgggggcag aaagaaactc  1020
ctgtatatat tcaaacaacc atttatgaga ccagtacaaa ctactcaaga ggaagatggc  1080
tgtagctgcc gatttccaga agaagaagaa ggaggatgtg aactgagagt gaagttcagc  1140
aggagcgcag acgccccgc gtacaagcag ggccagaacc agctctataa cgagctcaat  1200
ctaggacgaa gagaggagta cgatgttttg gacaagagac gtggccggga ccctgagatg  1260
gggggaaagc cgagaaggaa gaaccctcag gaaggcctgt acaatgaact gcagaaagat  1320
aagatggcgg aggcctacag tgagattggg atgaaaggcg agcgccggag gggcaagggg  1380
cacgatggcc tttaccaggg tctcagtaca gccaccaagg acacctacga cgcccttcac  1440
atgcaggccc tgccccctcg ctaa                                          1464

<210> SEQ ID NO 29
<211> LENGTH: 1461
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: encodes the polypeptide of SEQ ID NO:20
<220> FEATURE:
<221> NAME/KEY: misc_feature
<223> OTHER INFORMATION: 19VLVH.28TM.28z

<400> SEQUENCE: 29
atgcttctcc tggtgacaag ccttctgctc tgtgagttac cacacccagc attcctcctg    60
atcccagaca tccagatgac ccagtctcca tcctccctgt ctgcatctat aggagacaga   120
gtcaccatca cttgccaggc gagtcaggac attagcgact atttaaattg gtatcagcag   180
aaaccaggga aagcccctaa gctcctgatc tacgatgcat ccaatttgga gactggggtc   240
```

-continued

```
ccatcaaggt tcagtggaag tggatctggg acagatttta cttcaccat cagcagcctc      300 cagcctgaag atgttgcaac atattactgt caacagtatg ataatctccc gatcaccttc      360
ggccaaggga ccaagctgga aatcaaacgt ggaggtggcg ggtctggtgg aggcgctagc      420
ggtggtggcg gatcccagct gcagctgcag gagtcgggcc caggactggt gaagccttcg      480
gagaccctgt ccctcacctg cactgtctct ggtggctcca tcagcagtag tagttactac      540
tggagctgga tccgccagcc cccagggaag gggctggagt ggattgggag tatctattat      600
agtgggagca cctactacaa cccgtccctc aagagtcgag tcaccatatc agtagacacg      660
tccaagaacc agttctccct gaagctgagc tctgtgaccg ccgcggacac ggccgtgtat      720
tactgtgcga cacgggtcag tggccacccc ttcgacccct ggggccaggg aaccctggtc      780
accgtctcct cagcggccgc aattgaagtt atgtatcctc ctccttacct agacaatgag      840
aagagcaatg gaaccattat ccatgtgaaa gggaaacacc tttgtccaag tcccctattt      900
cccggacctt ctaagccctt ttgggtgctg gtggtggttg ggggagtcct ggcttgctat      960
agcttgctag taacagtggc ctttattatt ttctgggtga ggagtaagag gagcaggctc     1020
ctgcacagtg actacatgaa catgactccc cgccgccccg ggcccacccg caagcattac     1080
cagccctatg ccccaccacg cgacttcgca gcctatcgct ccagagtgaa gttcagcagg     1140
agcgcagacg cccccgcgta ccagcagggc cagaaccagc tctataacga gctcaatcta     1200
ggacgaagag aggagtacga tgttttggac aagagacgtg gccgggaccc tgagatgggg     1260
ggaaagccga gaaggaagaa ccctcaggaa ggcctgtaca tgaactgca gaaagataag     1320 atggcggagg cctacagtga gattgggatg aaaggcgagc gccggagggg caaggggcac     1380
gatggccttt accagggtct cagtacagcc accaaggaca cctacgacgc ccttcacatg     1440
caggccctgc cccctcgcta a                                              1461
```

```
<210> SEQ ID NO 30
<211> LENGTH: 1467
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: encodes the polypeptide of SEQ ID NO:23
<220> FEATURE:
<221> NAME/KEY: misc_feature
<223> OTHER INFORMATION: 19VHVL.8aH-8aTM.41BBz
```

```
<400> SEQUENCE: 30
atgcttctcc tggtgacaag ccttctgctc tgtgagttac cacacccagc attcctcctg       60
atcccacagc tgcagctgca ggagtcgggc ccaggactgg tgaagccttc ggagaccctg      120
tccctcacct gcactgtctc tggtggctcc atcagcagta gtagttacta ctggagctgg      180
atccgccagc ccccagggaa ggggctggag tggattggga gtatctatta tagtgggagc      240
acctactaca acccgtccct caagagtcga gtcaccatat cagtagacac gtccaagaac      300
cagttctccc tgaagctgag ctctgtgacc gccgcggaca cggccgtgta ttactgtgcg      360
agacgggtca gtggccaccc cttcgacccc tggggccagg gaaccctggt caccgtctcc      420
tcaggaggtg cgggtctggt ggaggcgct agcggtggtg cgggatccga catccagatg      480
acccagtctc catcctccct gtctgcatct ataggagaca gagtcaccat cacttgccag      540
gcgagtcagg acattagcga ctatttaaat tggtatcagc agaaaccagg gaaagcccct      600
```

-continued

```
aagctcctga tctacgatgc atccaatttg gagactgggg tcccatcaag gttcagtgga    660
agtggatctg ggacagattt tactttcacc atcagcagcc tccagcctga agatgttgca    720
acatattact gtcaacagta tgataatctc ccgatcacct tcggccaagg gaccaagctg    780
gaaatcaaac gtgcaaccac gacgccagcg ccgcgaccac caacaccggc gcccaccatc    840
gcgtcgcagc ccctgtccct gcgcccagag gcgtgccggc cagcggcggg gggcgcagtg    900
cacacgaggg ggctggactt cgcctgtgat atctacatct gggcgccctt ggccgggact    960
tgtggggtcc ttctcctgtc actggttatc acccctttact gcaaacgggg cagaaagaaa   1020
ctcctgtata tattcaaaca accatttatg agaccagtac aaactactca agaggaagat   1080
ggctgtagct gccgatttcc agaagaagaa gaaggaggat gtgaactgag agtgaagttc   1140
agcaggagcg cagacgcccc cgcgtacaag cagggccaga accagctcta taacgagctc   1200
aatctaggac gaagagagga gtacgatgtt ttggacaaga cgtggccg ggaccctgag    1260 atggggggaa agccgagaag gaagaaccct caggaaggcc tgtacaatga actgcagaaa   1320
gataagatgg cggaggccta cagtgagatt gggatgaaag gcgagcgccg gaggggcaag   1380
gggcacgatg gcctttacca gggtctcagt acagccacca aggacaccta cgacgccctt   1440
cacatgcagg ccctgccccc tcgctaa                                        1467
```

```
<210> SEQ ID NO 31
<211> LENGTH: 2160
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: encodes 19VHVL.CH2CH3.8aH-8aTM.41BBz
```

```
<400> SEQUENCE: 31
atgcttctcc tggtgacaag ccttctgctc tgtgagttac cacacccagc attcctcctg     60
atcccacagc tgcagctgca ggagtcgggc ccaggactgg tgaagccttc ggagaccctg    120
tccctcacct gcactgtctc tggtggctcc atcagcagta gtagttacta ctggagctgg    180
atccgccagc ccccagggaa ggggctggag tggattggga gtatctatta tagtgggagc    240
acctactaca acccgtccct caagagtcga gtcaccatat cagtagacac gtccaagaac    300
cagttctccc tgaagctgag ctctgtgacc gccgcggaca cggccgtgta ttactgtgcg    360
agacgggtca gtggccaccc cttcgacccc tggggccagg gaaccctggt caccgtctcc    420
tcaggaggtg gcgggtctgg tggaggcgct agcggtggtg gcggatccga catccagatg    480
acccagtctc catcctccct gtctgcatct ataggagaca gagtcaccat cacttgccag    540
gcgagtcaga acattagcga ctatttaaat tggtatcagc agaaaccagg gaaagcccct    600
aagctcctga tctacgatgc atccaatttg gagactgggg tcccatcaag gttcagtgga    660
agtggatctg ggacagattt tactttcacc atcagcagcc tccagcctga agatgttgca    720
acatattact gtcaacagta tgataatctc ccgatcacct tcggccaagg gaccaagctg    780
gaaatcaaac gtgagtccaa atatggtccc ccatgcccat catgcccagc acctccggtc    840
gcgggaccat cagtcttcct gttcccccca aaacccaagg acactctcat gatctcccgg    900
acccctgagg tcacgtgcgt ggtggtggac gtgagccagg aagaccccga ggtccagttc    960
aactggtacg tggatggcgt ggaggtgcat aatgccaaga caaagccgcg ggaggagcag   1020
ttccaaagca cgtaccgtgt ggtcagcgtc ctcaccgtcc tgcaccagga ctggctgaac   1080
```

-continued

```
ggcaaggagt acaagtgcaa ggtctccaac aaaggcctcc cgtcctccat cgagaaaacc   1140
atctccaaag ccaaagggca gccccgagag ccacaggtgt acaccctgcc cccatcccag   1200
gaggagatga ccaagaacca ggtcagcctg acctgcctgg tcaaaggctt ctaccccagc   1260
gacatcgccg tggagtggga gagcaatggg cagccggaga caactacaa gaccacgcct    1320 cccgtgctgg actccgacgg ctccttcttc ctctacagca ggctcaccgt ggacaagagc   1380
aggtggcagg aggggaatgt cttctcatgc tccgtgatgc atgaggctct gcacaaccac   1440
tacacacaga gagcctctc cctgtctctg ggtaaatcgg cggccgcaac cacgacgcca    1500
gcgccgcgac caccaacacc ggcgcccacc atcgcgtcgc agccctgtc cctgcgccca    1560 gaggcgtgcc ggccagcggc ggggggcgca gtgcacacga gggggctgga cttcgcctgt   1620
gatatctaca tctgggcgcc cttggccggg acttgtgggg tccttctcct gtcactggtt   1680
atcacccttt actgcaaacg gggcagaaag aaactcctgt atatattcaa acaaccattt   1740
atgagaccag tacaaactac tcaagaggaa gatggctgta gctgccgatt tccagaagaa   1800
gaagaaggag gatgtgaact gagagtgaag ttcagcagga gcgcagacgc ccccgcgtac   1860
aagcagggcc agaaccagct ctataacgag ctcaatctag gacgaagaga ggagtacgat   1920
gttttggaca gagacgtgg ccgggaccct gagatggggg gaaagccgag aaggaagaac    1980
cctcaggaag gcctgtacaa tgaactgcag aaagataaga tggcggaggc ctacagtgag   2040
attgggatga aggcgagcg ccggagggggc aagggggcacg atggccttta ccaggggtctc  2100 agtacagcca ccaaggacac ctacgacgcc cttcacatgc aggccctgcc ccctcgctaa   2160
```

<210> SEQ ID NO 32
<211> LENGTH: 1464
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: encodes the polypeptide of SEQ ID NO:24
<220> FEATURE:
<221> NAME/KEY: misc_feature
<223> OTHER INFORMATION: 27VLVH.8aH-8aTM.41BBz

<400> SEQUENCE: 32

```
atgcttctcc tggtgacaag ccttctgctc tgtgagttac cacacccagc attcctcctg     60
atcccagaaa ttgtgatgac gcagtctcca gccaccctgt ctgcatctgt aggagacaga    120
gtcaccatcg cttgccgggc aagtcagacc attagtaggt atttaaattg gtatcagcag    180
aaaccaggga aagcccctaa gctcctgatc tatgcagcat ccagtttgca aagtgggggtc   240 tcatcaaggt tcagtggcag tggatctggg acagagttca ctctcaccat cagcagtctg    300
cagcctgaag attttgcaac ttatttctgt caacagactt acagtccccc gatcaccttc    360
ggccaaggga cacgactgga gattaaacga ggaggtggcg gtctggtgg aggcgctagc     420 ggtggtggcg gatccgaggt gcagctggtg gagtccggcc aggactggt gaagccttcg     480 gagaccctgt ccctcacctg cgctgtctct ggttactcca tcagcagtgg ttactactgg    540
ggctggatcc ggcagccccc agggaagggg ctggagtgga ttgggagtat ctatcatagt    600
gggagcacct actacaaccc gtccctcaag agtcgagtca ccatatcagt agacacgtcc    660
aagaaccagt tctccctgaa gctgagctct gtgaccgccg cagacacggc cgtgtattac    720
tgtgcgagtt tgccgagtcg gggggggtttt gactattggg gccagggcac cctggtcacc   780
gtctcctcag caaccacgac gccagcgccg cgaccaccaa caccggcgcc caccatcgcg   840
```

-continued

```
tcgcagcccc tgtccctgcg cccagaggcg tgccggccag cggcggggg cgcagtgcac      900 acgagggggc tggacttcgc ctgtgatatc tacatctggg cgcccttggc cgggacttgt      960
ggggtccttc tcctgtcact ggttatcacc ctttactgca aacggggcag aaagaaactc     1020
ctgtatatat tcaaacaacc atttatgaga ccagtacaaa ctactcaaga ggaagatggc     1080
tgtagctgcc gatttccaga agaagaagaa ggaggatgtg aactgagagt gaagttcagc     1140
aggagcgcag acgcccccgc gtacaagcag ggccagaacc agctctataa cgagctcaat     1200
ctaggacgaa gagaggagta cgatgttttg gacaagagac gtggccggga ccctgagatg     1260
gggggaaagc cgagaaggaa gaaccctcag gaaggcctgt acaatgaact gcagaaagat     1320
aagatggcgg aggcctacag tgagattggg atgaaaggcg agcgccggag gggcaagggg     1380
cacgatggcc tttaccaggg tctcagtaca gccaccaagg acacctacga cgcccttcac     1440
atgcaggccc tgcccctcg ctaa                                              1464
```

<210> SEQ ID NO 33
<211> LENGTH: 1464
<212> TYPE: DNA
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: encodes the polypeptide of SEQ ID NO:25
<220> FEATURE:
<221> NAME/KEY: misc_feature
<223> OTHER INFORMATION: 27VHVL.8aH-8aTM.41BBz

<400> SEQUENCE: 33

```
atgcttctcc tggtgacaag ccttctgctc tgtgagttac cacacccagc attcctcctg       60
atcccagagg tgcagctggt ggagtccggc ccaggactgg tgaagccttc ggagaccctg      120
tccctcacct gcgctgtctc tggttactcc atcagcagtg gttactctg gggctggatc      180 cggcagcccc cagggaaggg gctggagtgg attgggagta tctatcatag tgggagcacc      240
tactacaacc cgtccctcaa gagtcgagtc accatatcag tagacacgtc caagaaccag      300
ttctccctga agctgagctc tgtgaccgcc gcagacacgg ccgtgtatta ctgtgcgagt      360
ttgccgagtc gggggggttt tgactattgg ggccagggca ccctggtcac cgtctcctca      420
ggaggtggcg gtctggtgg aggcgctagc ggtggtggcg gatccgaaat tgtgatgacg      480
cagtctccag ccaccctgtc tgcatctgta ggagacagag tcaccatcgc ttgccgggca      540
agtcagacca ttagtaggta tttaaattgg tatcagcaga aaccagggaa agcccctaag      600
ctcctgatct atgcagcatc cagtttgcaa agtggggtct catcaaggtt cagtggcagt      660
ggatctggga cagagttcac tctcaccatc agcagtctgc agcctgaaga ttttgcaact      720
tatttctgtc aacagactta cagtcccccg atcaccttcg gccaagggac acgactggag      780
attaaacgag caaccacgac gccagcgccg cgaccaccaa caccggcgcc caccatcgcg      840
tcgcagcccc tgtccctgcg cccagaggcg tgccggccag cggcggggg cgcagtgcac      900 acgagggggc tggacttcgc ctgtgatatc tacatctggg cgcccttggc cgggacttgt      960
ggggtccttc tcctgtcact ggttatcacc ctttactgca aacggggcag aaagaaactc     1020
ctgtatatat tcaaacaacc atttatgaga ccagtacaaa ctactcaaga ggaagatggc     1080
tgtagctgcc gatttccaga agaagaagaa ggaggatgtg aactgagagt gaagttcagc     1140
aggagcgcag acgcccccgc gtacaagcag ggccagaacc agctctataa cgagctcaat     1200
```

-continued

```
ctaggacgaa gagaggagta cgatgttttg gacaagagac gtggccggga ccctgagatg    1260 ggggggaaagc cgagaaggaa gaaccctcag gaaggcctgt acaatgaact gcagaaagat    1320
aagatggcgg aggcctacag tgagattggg atgaaaggcg agcgccggag gggcaagggg    1380
cacgatggcc tttaccaggg tctcagtaca gccaccaagg acacctacga cgcccttcac    1440
atgcaggccc tgccccctcg ctaa                                          1464
```

CHIMERIC ANTIGEN RECEPTORS TARGETING GLYPICAN-2

CROSS-REFERENCE TO RELATED APPLICATIONS

The present application is a U.S. National Phase Application of PCT International Application No. PCT/US2020/031729, filed on May 6, 2020, designating the United States of America, which is an International Application of and claims the benefit of priority to U.S. Provisional Patent Application Ser. No. 62/844,695, filed on May 7, 2019. The disclosures of the above-referenced applications are herein expressly incorporated by reference it their entirety, including any drawings.

STATEMENT REGARDING FEDERALLY SPONSORED R&D

This invention was made with government support project number ZIA BC 010701 and contracts CA232568 and CA217959 awarded by the National Institutes of Health. The government has certain rights in the invention.

INCORPORATION OF THE SEQUENCE LISTING

The present application is being filed along with a Sequence Listing in electronic format. The material in the accompanying Sequence Listing is hereby incorporated by reference into this application The accompanying Sequence Listing text file, named "078460-507NO1US_SequenceListing_ST25.txt," was created on Nov. 2, 2021 and is 62,213 bytes.

FIELD

The present disclosure relates generally to the fields of oncology and immunotherapeutics, and particularly relates to antibodies and chimeric antigen receptors (CARs) that bind a Glypican 2 (GPC2) antigen. The disclosure also provides compositions and methods useful for producing such antibodies and CARs, as well as methods for the diagnosis, prevention, and/or treatment of health conditions associated with GPC2 antigen expression.

BACKGROUND

Biopharmaceuticals or the use of pharmaceutical compositions comprising a therapeutic protein for the treatment of health conditions is a core strategy for a number of pharmaceutical and biotechnology companies. For example, in cancer immunotherapy, the development of agents that activate T cells of the host's immune system to prevent the proliferation of or kill cancer cells, has emerged as a promising therapeutic approach to complement existing standards of care. Adoptive transfer of T cells, especially chimeric antigen receptor (CAR) engineered T cells, has emerged as another promising approach in cancer immunotherapy. Unlike naturally occurring T cell receptors, CARs can directly recognize their target antigens without restrictions imposed by major histocompatibility complex (MHC) molecules and can potentially mediate high levels of cell-killing activity. One common method is to genetically engineer T cells ex vivo to express CARs which can recognize target antigens without the need for MHC presentation.

These CAR-T cells have the potential to generate very high levels of anti-tumor activity towards cells expressing the target antigen.

There remains an urgent need for the development of novel immunotherapies. Described herein are immuno-reagents, including antibodies and CAR T-cell receptors that selectively bind GPC2 antigen, as well as and methods for the treatment of health conditions associated with expression of GPC2 as a cell surface protein in a subject in need thereof.

SUMMARY

The present disclosure generally relates to the development of immuno-reagents, including antibodies and CARs that selectively target a Glypican 2 antigen (which is referred to hereafter as "GPC2-targeting CAR") for use in detecting and treating cancers that express GPC2.

In one aspect, some embodiments of the disclosure relate to a chimeric antigen receptor (CAR) including: (i) an anti-GPC2 single-chain variable fragment (anti-GPC2 scFv) region including a variable heavy chain (VH) and a variable light chain (VL); (ii) a transmembrane domain (TMD); and (iii) an intracellular signaling domain (ICD), wherein the anti-GPC2 scFv region does not include a VH or a VL sequence of SEQ ID NO: 2, SEQ ID NO: 4, SEQ ID NO: 12, SEQ ID NO: 14, SEQ ID NO: 22, or SEQ ID NO: 24 disclosed in PCT Publication No. WO/2017/083296.

Implementations of embodiments of the GPC2-targeting CAR of the disclosure can include one or more of the following features. In some embodiments, the GPC2-targeting CAR includes (i) an anti-Glypican 2 scFv region, (ii) a TMD, and (iii) an ICD, wherein the anti-Glypican 2 scFv (anti-GPC2 scFv) region includes (a) the variable heavy chain CDR 1, 2 and 3 (HCDR1, HCDR2, HCDR3) amino acid sequences as shown in SEQ ID NOS: 1, 2, and 3, respectively; and (b) the variable light chain CDR 1, 2 and 3 (LCDR1, LCDR2, LCDR3) amino acid sequences as shown in SEQ ID NOS: 4, 5, and 6, respectively, wherein one, two, three, four, or five of the amino acid residues in any one of the CDRs is optionally substituted by a different amino acid residue. In some embodiments, the anti-GPC2 scFv region includes a VH framework region and VL framework region having at least 80% identity to the framework regions of SEQ ID NO: 7 and SEQ ID NO: 8, respectively.

In some embodiments, the GPC2-targeting CAR includes (i) an anti-Glypican 2 scFv region, (ii) a TMD, and (iii) an ICD, wherein the anti-GPC2 scFv region includes (a) the variable heavy chain CDR 1, 2 and 3 (HCDR1, HCDR2, HCDR3) amino acid sequences as shown in SEQ ID NOS: 9, 10, and 11, respectively; and (b) the variable light chain CDR 1, 2 and 3 (LCDR1, LCDR2, LCDR3) amino acid sequences as shown in SEQ ID NOS: 12, 13, and 14, respectively, wherein one, two, three, four, or five of the amino acid residues in any one of the CDRs is optionally substituted by a different amino acid residue. In some embodiments, the anti-GPC2 scFv region includes a VH framework region and VL framework region having at least 80% identity to the framework regions of SEQ ID NO: 15 and SEQ ID NO: 16, respectively. In some embodiments, the HCDRs and LCDRs of the CAR do not include the CDR sequences of SEQ ID NOS: 5-10, 15-20 and 25-30 disclosed in PCT Publication No. WO/2017/083296.

In some embodiments of the GPC2-targeting CAR disclosed herein, the VH sequence is operably linked downstream to the VL sequence. In some embodiments, the VH sequence is operably linked upstream to the VL sequence. In some embodiments, the TMD is a TMD from a polypeptide selected from the group consisting of T-cell receptor (TCR) alpha chain, a TCR beta chain, a TCR zeta chain, CD3 epsilon, CD4, CD5, CD8, CD9, CD16, CD22, CD27 (TN-FRSF19), CD28, CD33, CD45, CD80, CD83, CD86, CD134, 4-1BB (CD137), CD152 (CTLA4), CD154, CD279, and PD-1, and a combination of any thereof. In some embodiments, the ICD includes a co-stimulatory domain. In some embodiments, the co-stimulatory domain is a co-stimulatory domain from a polypeptide selected from the group consisting of 4-1BB, CD27 (TNFRSF7), CD28, OX40 (CD134), CD70, LFA-2 (CD2), CD5, ICAM-1 (CD54), LFA-1 (CD11a/CD18), DAP10, DAP12, inducible T-cell costimulatory (ICOS) polypeptide sequence, and a combination of any thereof.

In some embodiments, the GPC2-targeting CAR further includes an extracellular hinge domain operably linked downstream to the anti-GPC2 scFv (anti-GPC2 scFv) region and upstream to the TMD. In some embodiments, the extracellular hinge domain is a hinge domain from a poly-peptide selected from the group consisting of LFA-1 (CD11a/CD18), LFA-2 (CD2), CD4, CD5, CD8, CD27 (TNFRSF7), CD28, CD70, 4-1BB, OX40 (CD134), CD152 (CTLA4), ICOS (CD278), IgG1 Fc region, IgG4 Fc region, and a combination of any thereof. In some embodiments, the CAR further includes an extracellular spacer domain oper-ably linked downstream to the anti-GPC2 scFv region and upstream to the extracellular hinge domain. In some embodiments, the extracellular spacer domain includes an IgG4 hinge domain and an IgG4 CH2-CH3 domain. In some embodiments, the ICD includes a CD35 ICD.

In some embodiments of the disclosure, the GPC2-tar-geting CAR includes a) an anti-Glypican 2 scFv region; b) a CD28 hinge domain; c) a CD28 TMD; and d) an ICD including a co-stimulatory domain derived from a 4-1BBz co-stimulatory domain or a CD28 co-stimulatory domain. In some embodiments, the GPC2-targeting CAR includes an amino acid sequence having at least 80% sequence identity to an amino acid sequence selected from the group consist-ing of SEQ ID NOs: 17-25.

In one aspect, some embodiments relate to an antibody including an antigen-binding moiety which includes one or more complementarity determining regions (CDRs) having the sequences as shown in SEQ ID NOS: 1-6 and 9-14, wherein one, two, three, four, or five of the amino acid residues in any one of the CDRs is optionally substituted by a different amino acid residue. In some embodiments, the antibody is selected from the group consisting of: (a) an antibody having respectively a VH and VL region of SEQ ID NO: 7 and SEQ ID NO: 8 (GPC2.19); and (b) an antibody having respectively a VH and VL region of SEQ ID NO: 15 and SEQ ID NO: 16 (GPC2.27). In some embodiments, the antibody is a non-naturally occurring antibody.

In some embodiments, the antibody is an antibody having the variable heavy chain CDR 1, 2 and 3 (HCDR1, HCDR2, HCDR3) amino acid sequences as shown in SEQ ID NOS: 1, 2, and 3, respectively (GPC2.19), wherein one, two, three, four, or five of the amino acid residues in any one of the CDRs is optionally substituted by a different amino acid residue. In some embodiments, the antibody is an antibody having the variable light chain CDR 1, 2 and 3 (LCDR1, LCDR2, LCDR3) amino acid sequences as shown in SEQ ID NOS: 4, 5, and 6, respectively (GPC2.19), wherein one, two, three, four, or five of the amino acid residues in any one of the CDRs is optionally substituted by a different amino acid residue. In some embodiments, the antibody comprises a VH framework region and VL framework region having at least 80% identity to the framework regions of SEQ ID NO: 7 and SEQ ID NO: 8 (GPC2.19), respectively.

In some embodiments, the antibody is an antibody having the variable heavy chain CDR 1, 2 and 3 (HCDR1, HCDR2, HCDR3) amino acid sequences as shown in SEQ ID NOS: 9, 10, and 11, respectively (GPC2.27), wherein one, two, three, four, or five of the amino acid residues in any one of the CDRs is optionally substituted by a different amino acid residue. In some embodiments, the antibody is an antibody having the variable light chain CDR 1, 2 and 3 (LCDR1, LCDR2, LCDR3) amino acid sequences as shown in SEQ ID NOS: 12, 13, and 14, respectively (GPC2.27), wherein one, two, three, four, or five of the amino acid residues in any one of the CDRs is optionally substituted by a different amino acid residue. In some embodiments, the antibody comprises a VH framework region and VL framework region having at least 80% identity to the framework regions of SEQ ID NO: 15 and SEQ ID NO: 16 (GPC2.27), respectively. In some embodiments, the antibody is a mouse antibody. In some embodiments, the antibody is a chimeric, human or humanized antibody. In some embodiments, the antibody a single-chain antibody fragment (scFv). In a related aspect, some embodiments relate to a CAR including an antigen-binding region of the anti-GPC2 antibody described herein. In some embodiments, the chimeric anti-gen receptor (CAR) includes an anti-GPC2 single-chain antibody fragment (scFv) as described herein. In some embodiments, the CAR includes an antigen-binding moiety derived from an antibody as described herein.

In one aspect, some embodiments of the disclosure relate to a recombinant nucleic acid molecule including a nucleic acid sequence that encodes a CAR as disclosed herein, and/or an antibody as disclosed herein. Implementations of embodiments of the recombinant nucleic acid of the disclo-sure can include one or more of the following features. In some embodiments, the recombinant nucleic acid molecule includes a nucleic acid sequence encoding a CAR that includes (i) an anti-GPC2 scFv region including a VH and a VL; (ii) a TMD; and (iii) an ICD, wherein the anti-GPC2 scFv region does not include a VH or a VL sequence of SEQ ID NO: 2, SEQ ID NO: 4, SEQ ID NO: 12, SEQ ID NO: 14, SEQ ID NO: 22, or SEQ ID NO: 24 disclosed in PCT Publication No. WO/2017/083296. In some embodiments, the recombinant nucleic acid molecule includes a nucleic acid sequence encoding a CAR that includes (i) an anti-Glypican 2 scFv region, (ii) a TMD, and (iii) an ICD, wherein the anti-GPC2 scFv region includes (a) the variable heavy chain CDR 1, 2 and 3 (HCDR1, HCDR2, HCDR3) amino acid sequences as shown in SEQ ID NOS: 1, 2, and 3, respectively; and (b) the variable light chain CDR 1, 2 and 3 (LCDR1, LCDR2, LCDR3) amino acid sequences as shown in SEQ ID NOS: 4, 5, and 6, respectively, wherein one, two, three, four, or five of the amino acid residues in any one of the CDRs is optionally substituted by a different amino acid residue. In some embodiments, the recombinant nucleic acid molecule includes a nucleic acid sequence encoding a CAR that includes a VH framework region and VL framework region having at least 80% identity to the framework regions of SEQ ID NO: 7 and SEQ ID NO: 8, respectively.

In some embodiments, the recombinant nucleic acid mol-ecule includes a nucleic acid sequence encoding a CAR that includes (i) an anti-GPC2 scFv region, (ii) a TMD, and (iii) an ICD, wherein the anti-GPC2 scFv region includes (a) the variable heavy chain CDR 1, 2 and 3 (HCDR1, HCDR2, HCDR3) amino acid sequences as shown in SEQ ID NOS: 9, 10, and 11, respectively; and (b) the variable light chain CDR 1, 2 and 3 (LCDR1, LCDR2, LCDR3) amino acid sequences as shown in SEQ ID NOS: 12, 13, and 14, respectively, wherein one, two, three, four, or five of the amino acid residues in any one of the CDRs is optionally substituted by a different amino acid residue. In some embodiments, the anti-GPC2 scFv region includes a VH framework region and VL framework region having at least 80% identity to the framework regions of SEQ ID NO: 15 and SEQ ID NO: 16, respectively.

In some embodiments, the nucleic acid sequence has at least 80% sequence identity to a nucleic acid sequence selected from the group consisting of SEQ ID NOs: 26-33. In some embodiments, the recombinant nucleic acid molecule is operably linked to a heterologous nucleic acid sequence. In some embodiments, the recombinant nucleic acid molecule is further defined as an expression cassette or a vector. In some embodiments, the vector is a lentiviral vector, an adeno virus vector, an adeno-associated virus vector, a baculovirus, or a retroviral vector.

In one aspect, some embodiments of the disclosure relate to a recombinant cell including: (a) a CAR as described herein; (b) an antibody as disclosed herein; (iii) and/or a nucleic acid molecule according as described herein. In some embodiments, the recombinant cell is a prokaryotic cell or a eukaryotic cell. In some embodiments, the recombinant cell is an immune system cell. In some embodiments, the immune system cell is a T lymphocyte.

In another aspect, some embodiments disclosed herein relate to methods for making a recombinant cell, wherein the method includes (a) providing a host cell capable of protein expression; and (b) transducing the provided host cell with a recombinant nucleic acid of the disclosure to produce a recombinant cell. Accordingly, in a related aspect, also provided herein are recombinant cells produced by the methods of the disclosure. In a related aspect, some embodiments of the disclosure provide cell cultures that include at least one recombinant cell as described herein and a culture medium.

In another aspect, some embodiments of the disclosure relate to a pharmaceutical composition including (a) a pharmaceutically acceptable carrier and (b) one or more of: (i) a CAR as described herein; (ii) a nucleic acid molecule as described herein; (iii) a recombinant cell as described herein; (iv) an antibody as disclosed herein. In some embodiments, the composition includes a recombinant nucleic acid of the disclosure and a pharmaceutically acceptable carrier. In some embodiments, the recombinant nucleic acid is encapsulated in a viral capsid or a lipid nanoparticle. In some embodiments, the composition includes a recombinant cell of the disclosure and a pharmaceutically acceptable carrier.

In one aspect, some embodiments of the disclosure relate to methods for diagnosing, preventing, and/or treating a condition in a subject in need thereof, wherein the methods include administering to the subject a composition comprising one or more of the following: (i) a CAR of the disclosure; (ii) a nucleic acid molecule of the disclosure; (iii) a recombinant cell of the disclosure; (iv) an antibody of the disclosure; and (iv) a pharmaceutical composition of the disclosure. Implementations of embodiments of the methods of the disclosure can include one or more of the following features. In some embodiments, the condition is a health disorder or proliferative disease. In some embodiments, the proliferative disease is a cancer. In some embodiments, the cancer is a pediatric cancer or an adult malignancy. In some embodiments, the cancer expresses or overexpresses the GPC2 antigen (GPC2-positive cancer).

In some embodiments, the GPC2-positive cancer is a leukemia. In some embodiments, the leukemia is selected from the group consisting of acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), and hairy cell leukemia.

In some embodiments, the GPC2-positive cancer is a solid tumor cancer. In some embodiments, the solid tumor cell is lung cancer, liver cancer, pancreatic cancer, stomach cancer, colon cancer, kidney cancer, brain cancer, head and neck cancer, breast cancer, skin cancer, rectal cancer, uterine cancer, cervical cancer, ovarian cancer, testicular cancer, skin cancer, or esophageal cancer. In some embodiments, the cancer includes a sarcoma cell, a rhabdoid cancer cell, a neuroblastoma cell, retinoblastoma cell, or a medulloblastoma cell. In some embodiments, the GPC2-positive cancer is uterine carcinosarcoma (UCS), brain lower grade glioma (LGG), thymoma (THYM), testicular germ cell tumors (TGCT), glioblastoma multiforme (GBM) and skin cutaneous melanoma (SKCM), liver hepatocellular carcinoma (LIHC), uveal melanoma (UVM), kidney chromophobe (KICH), thyroid cancer (THCA), kidney renal clear cell carcinoma (KIRC), kidney renal papillary cell carcinoma (KIRP), stomach adenocarcinoma (STAD), cholangiocarcinoma (CHOL), adenoid cystic carcinoma (ACC), prostate adenocarcinoma (PRAD), pheochromocytoma and paraganglioma (PCPG), DLBC, lung adenocarcinoma (LUAD), small cell lung cancer (SCLC), head-neck squamous cell carcinoma (HNSC), pancreatic adenocarcinoma (PAAD), breast cancer (BRCA), mesothelioma (MESO), colon and rectal adenocarcinoma (COAD), rectum adenocarcinoma (READ), esophageal carcinoma (ESCA), ovarian cancer (OV), lung squamous cell carcinoma (LUSC), bladder urothelial carcinoma (BLCA), sarcoma (SARC), or uterine corpus endometrial carcinoma (UCEC). In some embodiments, the administered first therapeutic agent inhibits tumor growth or metastasis of the GPC2-positive cancer in the subject. In some embodiments, the GPC2-positive cancer includes a metastatic cancer cell, a multiply drug resistant cancer cell, or a recurrent cancer cell. In some embodiments, the administered first therapeutic agent results in increased production of interferon gamma (IFNγ) and/or interleukin-2 (IL-2) in the subject.

In some embodiments of the methods disclosed herein, the composition is administered to the subject individually as a first therapy or in combination with a second therapy. In some embodiments, the second therapy is selected from the group consisting of chemotherapy, radiotherapy, immunotherapy, hormonal therapy, toxin therapy, and surgery. In some embodiments, the first therapy and the second therapy are administered concomitantly. In some embodiments, the first therapy is administered at the same time as the second therapy. In some embodiments, the first therapy and the second therapy are administered sequentially. In some embodiments, the first therapy is administered before the second therapy. In some embodiments, the first therapy is administered after the second therapy. In some embodiments, the first therapy is administered before and/or after the second therapy. In some embodiments, the first therapy and the second therapy are administered in rotation. In some embodiments, the first therapy the second therapy are administered together in a single formulation.

In another aspect, some embodiments of the disclosure provide various kits for the practice of the methods disclosed herein. Some embodiments relate to kits for methods of the diagnosis, prevention, and/or treatment of a condition in a subject in need thereof, wherein the kits include one or more of: a CAR of the disclosure, and antibody of the disclosure, a recombinant nucleic acid of the disclosure, a recombinant cell of the disclosure, and a pharmaceutical composition of the disclosure.

In another aspect, provided herein is the use of one or more of: a CAR of the disclosure, an antibody of the disclosure, a recombinant nucleic acid of the disclosure, a recombinant cell of the disclosure, and a pharmaceutical composition of the disclosure, for the diagnosis, prevention, and/or treatment of a condition. In some embodiments, the condition is a health disorder or proliferative disease. In some embodiments, the proliferative disease is a cancer.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

BRIEF DESCRIPTION OF THE DRAWINGS

FIG. 2A is an amino acid sequence alignment of GPC2 targeted single chain variable fragments (scFv) in the variable heavy chain-linker-variable light chain (VH-L-VL) configuration of GPC2.19 (SEQ ID NO: 21) and GPC2.27 (SEQ ID NO: 22). Complementarity-determining regions (CDR) are highlighted. FIG. 2B depicts a schematic of exemplary CAR T-cell constructs used for testing GPC2 scFv's. These constructs utilize CD8a hinge-transmembrane domains and 41BB costimulatory domains in variable light chain-linker-variable heavy chain (VL-L-VH) configuration and variable heavy chain-linker-variable light chain (VH-L-VL) orientation. FIG. 2C shows representative histograms of GPC2.CAR cell surface expression among different constructs assessed by their capacity to bind to fluorescently labelled recombinant GPC2 protein.

FIG. 2D schematically illustrates cytolytic activity of GPC2.CAR T-cells against target cell lines with supraphysiological GPC2 antigen density (NGP-GPC2). FIG. 2E:

native (NBSD) antigen density levels in IncuCyte killing assays at 1:1 effector to target ratios. FIG. 2F-2G: GPC2.CAR T-cells challenged with 5× excess tumor cells. FIG. 2H: Secretion of IFNγ and IL-2 of GPC2.CAR T-cells in response to supraphysiological (NGP-GPC2) antigen exposure in 24 hour co-culture assays (mean±SD). Representative of n=3 independent experiments with 3 individual donors (e.g., healthy individual of which T-cells were derived from, DNRs).

FIG. 3A: Schematic of GPC2.CAR T-cell constructs utilizing CD8a hinge-transmembrane domains and 41BB costimulatory domains in variable light chain-linker-variable heavy chain (VL-L-VH) orientation of single-chain variable fragments. FIG. 3B: Cell surface antigen density of GPC2 on neuroblastoma cell lines at supraphysiological antigen density levels in isogenic cell lines (NGP-GPC2), native GPC2 expressing (NBSD, SMS-SAN) cell lines and negative control (CHO) and isotype control. GPC2 was stained with an anti-GPC2 antibody labelled with Dylight650. Representative histogram of n=4 independent experiments. FIG. 3C: IFNγ secretion of GPC2.19 CAR T-cells in response to increasing antigen levels on SMS-SAN (GPC2+), NBSD (GPC2++) and NGP-GPC2 (GPC2++++) cell lines. Representative of n=4 independent experiments (mean+SD). FIG. 3D: Quantification of GPC2 molecules per cell on native GPC2 expressing (NBSD, SMS-SAN) cell lines and isogenic cell line NGP-GPC2. FIG. 3E: Cytolytic activity of GPC2.19 CAR T-cells in vitro against native SMS-SAN (GPC2+) and FIG. 3F: NBSD (GPC2++) cells when challenged with 5× excess of tumor cells. Values represent mean±SEM, representative of n=4 independent experiments. FIG. 3G: Schematic of experimental outline testing the in vivo efficacy of GPC2.19 CAR T-cells in orthotopic neuroblastoma subrenal capsule xenograft models against FIG. 3H: SMS-SAN (GPC2+) or FIG. 3I: NBSD (GPC2++) engrafted cell lines assessed by bioluminescent imaging (n=1 each). Values represent FLUX [P/s] mean±SEM. FIG. 3J Cytolytic activity of GPC2.19 CAR T-cells in vitro against isogenic NGP-GPC2 (GPC2++++) with supraphysiological site density when challenged with 5× excess of tumor cells. Values represent mean±SEM, representative of n=3 independent experiments. FIG. 3K: Schematic of experimental outline and in vivo efficacy of GPC2.19 CAR T-cells in orthotopic neuroblastoma subrenal capsule xenograft models against isogenic NGP-GPC2 (GPC2++++) with supraphysiological site density (n=1). Values represent FLUX [P/s] mean±SEM.

FIG. 4A: Schematic of GPC2.CAR T-cells constructs incorporating an extracellular CH2CH3 spacer domain. FIG. 4B: representative histogram of GPC2.CAR cell surface expression of constructs with/without CH2CH3 spacer domain. FIG. 4C: Expansion of GPC2.CAR T-cells shown as total viable cells (×10⁶ cells) during in vitro culture (representative of n=3 independent experiments with 3 different DNRs). FIG. 4D: IFNγ production of GPC2.CAR T-cells with/without CH2CH3 spacer domain in response to 24-hour co-culture with native antigen density SMS-SAN (GPC2+), NBSD (GPC2++) cell lines (mean±SD), representative of n=3 independent experiments with n=3 individual DNRs. FIG. 4E: Cytolytic activity of GPC2.CAR T-cells with/without CH2CH3 spacer domain, either at 1:1 effector to target ratios or when challenged with 5× excess tumor of native antigen density SMS-SAN (GPC2+), NBSD (GPC2++) cell lines (mean±SEM), representative of n=3 independent experiments with n=3 individual DNRs.

FIG. 5A: Schematic of GPC2.CAR T-cells constructs incorporating CD8a or CD28 hinge-transmembrane domains with 41BB costimulatory domains and CD28 hinge-transmembrane domains with CD28 costimulatory domains. FIG. 5B: representative histogram of GPC2.CAR cell surface expression among different constructs assessed by binding to fluorescently labelled recombinant GPC2. FIG. 5C: Mean fluorescent intensity of CAR expression (log 10 of CAR MFI normalized to Mock, day 10 or 11, n=5 independent experiments with 5 different DNRs, mean±SEM). One-way multiple comparisons ANOVA=ns for all conditions. FIG. 5D: Exhaustion marker profile of CAR T-cell constructs evaluated by Flow Cytometry, Mean fluorescent intensity of PD1, Tim3, Lag3 expression (log 10 of MFI normalized to FMC63 CTRL CAR, day 10 or 11, n=5 independent experiments with 5 different donors, mean±SEM). Statistics represent one-way multiple comparisons ANOVA.

FIG. 5E: Cytolytic activity of GPC2 CAR T-cells constructs when challenged with 5× excess tumor of native antigen density cell lines SMS-SAN (GPC2+) or NBSD (GPC2++). Values represent mean±SEM, representative of n=3 independent experiments with n=3 individual DNRs. IFNγ (FIG. 5F) and IL-2 (FIG. 5G) secretion of 19.GPC2.CAR T-cells in response to 24-hr co-culture with native antigen density cell line NBSD (GPC2++). Values represent mean±SD, representative of n=3 independent experiments with n=3 individual DNRs. FIG. 5H: Cytolytic activity of GPC2.CAR T-cells incorporating CD28 hinge-transmembrane domains with 41BB or CD28 costimulatory domains when challenged with 8× excess tumor of native antigen density cell lines SMS-SAN (GPC2+) or NBSD (GPC2++). Values represent mean±SEM, representative of n=3 independent experiments with n=3 individual DNRs. FIG. 5I: Histogram of GPC2.CAR cell surface expression used for killing assay shown in FIG. 5G.

FIG. 6A: Schematic of experimental setup testing the anti-tumor activity of GPC2.CAR T-cells incorporating CD8a hinge-transmembrane domains with 41BB costimulatory domains or CD28 hinge-transmembrane domains with 41BB or CD28 costimulatory domains in orthotopic neuroblastoma subrenal capsule xenograft model engrafted with native antigen density cell tumors NBSD (GPC2++). Bioluminescence images (FIG. 6B) and FLUX [P/s] values (FIG. 6C) of tumor burden assessed by IVIS imaging. FIG. 6D: Kaplan-Meier survival analysis of treatment arms shown in FIG. 6A. FIG. 6E: Schematic of experimental setup testing GPC2.CAR T-cell constructs in metastatic xenograft model engrafted with native antigen density cell tumors SMS-SAN (GPC2+). FIG. 6F: Bioluminescence images and FIG. 6G: FLUX [P/s] values of tumor burden assessed by IVIS imaging.

FIG. 8A: Gene expression of GPC2 in organs across human tissue developmental stages and FIG. 8B: murine developmental stages sourced from evodevoapp.kassmannlab.org.

FIG. 9A: ELISA for binding of GPC2.19-IgG1 to human GPC2 and murine GPC2. The EC50 for binding of GPC2.19-IgG1 to human hGPC2 and murine mGPC2 was on the order of 1 nM (0.15 mg/ml). Representative of n=2 independent experiments. FIG. 9B: Binding capacity of recombinant human GPC2 (labelled with Dylight650) or murine GPC2 (labelled with Dylight488) by GPC2.8aTM.41BBz CAR T-cells. Representative histogram of n=3 independent experiments with n=3 different DNRs. Secretion of IFNγ (FIG. 9C) and IL-2 (FIG. 9D) of GPC2.28TM.28z CAR T-cells after 24-hr co-culture with plate-bound recombinant human or murine GPC2 at increasing concentrations (µg/mL). Values shown as mean±SD. Representative of n=3 independent experiments with n=3 different donors.

FIG. 10A: Schematic of experimental setup: NSG mice were engrafted with 1×10⁶ NBSD-GFPluc+ tumor cells into the left subrenal capsule and treated with 10×10⁶ GPC2.28TM.28z or control FMC63.8aTM.41BBz CAR T-cells on day 4 via IV tail vein injection. Tumor burden and weight was followed until the endpoint on day 18. Tumor burden shown as total flux values, mean±SEM (FIG. 10B) and bioluminescence images (FIG. 10D), weight of treated mice (FIG. 10C) shown as change to baseline over the course of the experiment. FIG. 10E: Assessment of blood cell populations and liver function parameters (transaminases AST, ALT and alkaline phosphatase) and FIG. 10F: Hematoxylin and eosin [H&E] stained tissues from mice that were either treated with GPC2.28TM.28z CAR T-cells (A-J) or FMC63 control CAR T-cells (K-T). All tissues are histologically within normal limits, including heart (A, K), lung (B, L), liver (C, M), spleen (D, N), kidney (E, O), brain (F, P), stomach (G, Q), small intestine (H, R), colon (I, S), and testes (J, T). Magnification: 40×.

FIG. 11A: Schematic of experimental setup testing the anti-tumor activity of GPC2.CAR T-cells incorporating CD28 hinge-transmembrane domains with 41BB or CD28 costimulatory domains in patient-derived xenograft models bearing regular size tumor burden (range mean TU vol 0.22-0.24 cm³). FIG. 11B: tumor volume after treatment of treatments arms shown in FIG. 11A. FIG. 11B: Kaplan-Meier survival analysis of treatments arms shown in FIG. 11A. FIG. 11D: Histogram of GPC2.CAR cell surface expression of both constructs used for both experiments. FIG. 11E: Schematic of experimental setup testing GPC2.CAR T-cells in animals bearing high size tumor burden (range mean TU vol 0.65-0.78 cm³). Tumor volume after treatment (FIG. 11F), Kaplan-Meier survival analysis (FIG. 11F), and body weight (FIG. 11F), shown as change from baseline of treatments arms shown in FIG. 11E.

Figure 13:
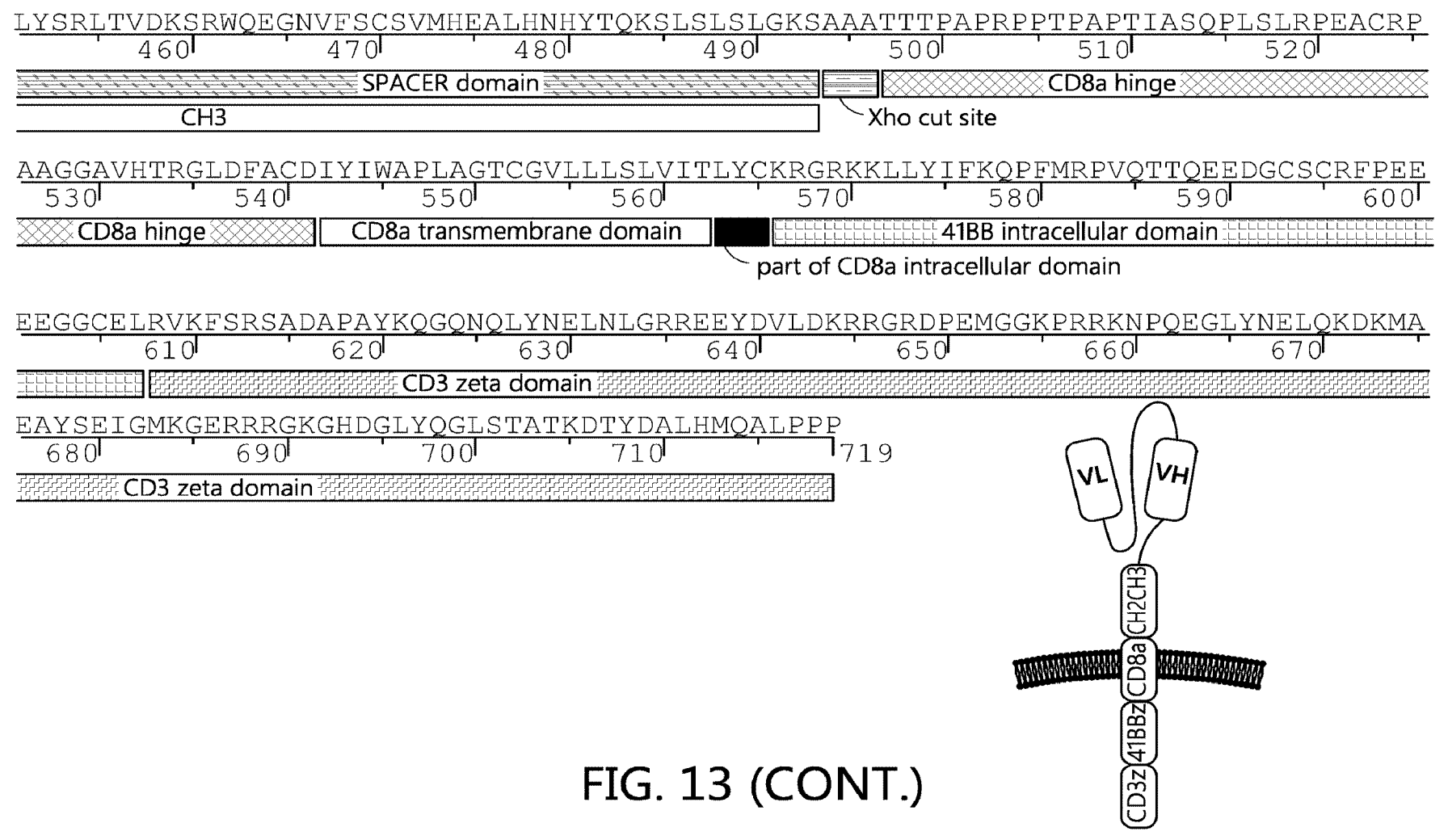

FIG. 13 shows a schematic diagram of another exemplary GPC2-targeting CAR, GPC2.19VLVH.CH2CH3.8aH-8aTM.41BBz (SEQ ID NO: 18). In this CAR, the spacer domain includes hinge, CH2, and regions CH3, all of which were derived from IgG4. The amino acid sequences corresponding to each of the components are also shown.

DETAILED DESCRIPTION OF THE DISCLOSURE

Figure 1:
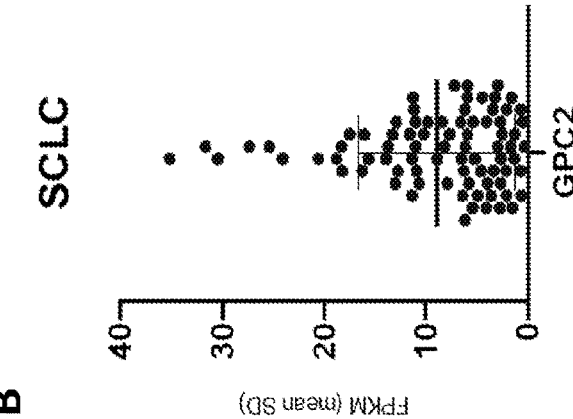
FIG. 1 schematically summarizes an expression profile for Glypican-2 (GPC2) in adult malignancies as queried from The Cancer Genome Atlas (TCGA). Highest expression of GPC2 is found on uterine carcinosarcoma (UCS), brain lower grade glioma (LGG), thymoma (THYM), testicular germ cell tumors (TGCT), glioblastoma multiforme (GBM) and skin cutaneous melanoma (SKCM) and small cell lung cancer (SCLC). In children, high levels of GPC2 expression was reported on neuroblastoma, retinoblastoma and medulloblastoma.
Figure 1:

The present disclosure generally relates to, inter alia, compositions and methods for the treatment of a health condition associated with expression of Glypican-2 (GPC2) as a cell surface protein in a subject in need thereof. GPC2 has been considered a promising immunotherapeutic target. It is present on the cell surface of numerous childhood and adult malignancies and demonstrates high differential expression between tumor and normal tissues. In particular, GPC2 has been identified as a cell surface protein on several cancer types, including neuroblastoma, high grade glioma (HGG), medulloblastoma, and several other pediatric cancers and adult malignancies. This presents an opportunity for the development of new targeted immunotherapies.

As will be discussed more thoroughly herein, some embodiments of the disclosure relate to the engineering of GPC2-targeted CAR T-cells and the optimization of several CAR modules to render CAR T-cells highly efficacious against tumors expressing native GPC2 site density. In particular, some embodiments of the disclosure relate to the identification of novel antibodies capable of selectively binding a GPC2 antigen that can be suitable for use in methods for the detection and/or treatment of health condition associated with elevated expression of GPC2 antigen on cell surface. In some embodiments, the disclosure provides novel CARs that have been designed to selectively bind GPC2 antigen and can be useful in methods for detecting and/or treating a health condition associated with GPC2 expression. As described in greater detail below, novel CARs targeting GPC2 have been engineered and improved to demonstrate that they are highly efficacious against GPC2-expressing malignancies in vitro and in vivo in mammals, as exemplified by murine xenograft models. In particular, GPC2-targeting CAR T-cells as described herein can prove efficacious in the treatment of a broad spectrum of pediatric and adult malignancies facing an otherwise poor prognosis.

Nucleic acid molecules encoding these GPC2-targeting CARs are also provided. The disclosure also provides compositions and methods useful for producing such anti-GPC2 antibodies and GPC2-targeting CARs, as well as methods for the treatment of health conditions associated with elevated expression of GPC2 as a cell surface protein.

All publications and patent applications mentioned in this disclosure are herein incorporated by reference to the same extent as if each individual publication or patent application was specifically and individually indicated to be incorporated by reference.

General Experimental Procedures

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as Sambrook, J., & Russell, D. W. (2012). *Molecular Cloning: A Laboratory Manual* (4th ed.). Cold Spring Harbor, NY: Cold Spring Harbor Laboratory and Sambrook, J., & Russel, D. W. (2001). *Molecular Cloning: A Laboratory Manual* (3rd ed.). Cold Spring Harbor, NY: Cold Spring Harbor Laboratory (jointly referred to herein as "Sambrook"); Ausubel, F. M. (1987). *Current Protocols in Molecular Biology*. New York, NY: Wiley (including supplements through 2014); Bollag, D. M. et al. (1996). *Protein Methods*. New York, NY: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, CA: Academic Press; Lefkovits, I. (1997). *The Immunology Methods Manual: The Comprehensive Sourcebook of Techniques*. San Diego, CA: Academic Press; Doyle, A. et al. (1998). *Cell and Tissue Culture: Laboratory Procedures in Biotechnology*. New York, NY: Wiley; Mullis, K. B., Ferré, F. & Gibbs, R. (1994). POR: *The Polymerase Chain Reaction*. Boston: Birkhauser Publisher; Greenfield, E. A. (2014). *Antibodies: A Laboratory Manual* (2nd ed.). New York, NY: Cold Spring Harbor Laboratory Press; Beaucage, S. L. et al. (2000). *Current Protocols in Nucleic Acid Chemistry*. New York, NY: Wiley, (including supplements through 2014); and Makrides, S. C. (2003). *Gene Transfer and Expression in Mammalian Cells*. Amsterdam, NL: Elsevier Sciences B. V., the disclosures of which are incorporated herein by reference. As appropriate, procedures involving the use of commercially available kits and reagents are generally carried out in accordance with manufacturer defined protocols and/or parameters unless otherwise noted.

Definitions

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof. "A and/or B" is used herein to include all of the following alternatives: "A", "B", "A or B", and "A and B".

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

As used herein, the term "antibody" refers to a class of proteins that are generally known as immunoglobulins capable of binding to an antigen molecule. The term antibody includes full-length monoclonal antibodies (mAb), such as IgG2 monoclonal antibodies, which include immunoglobulin Fc regions. The term antibody also includes bispecific antibodies, diabodies, single-chain antibody fragments (scFv), and antibody fragments such as Fab, F(ab')2, and Fv. In instances where the antibody is a bispecific antibody, the bispecific antibody can be in many different formats. The antibody can be monoclonal or polyclonal and can be prepared by techniques that are well known in the art, such as immunization of a host and collection of sera (polyclonal), or by preparing continuous hybrid cell lines and collecting the secreted protein (monoclonal), or by cloning and expressing nucleotide sequences or mutagenized versions thereof coding at least for the amino acid sequences required for specific binding of natural antibodies. As such, antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular target (i.e., GPC2) is maintained.

The terms "cell", "cell culture", "cell line" refer not only to the particular subject cell, cell culture, or cell line but also to the progeny or potential progeny of such a cell, cell culture, or cell line, without regard to the number of transfers or passages in culture. It should be understood that not all progeny are exactly identical to the parental cell. This is because certain modifications may occur in succeeding generations due to either mutation (e.g., deliberate or inadvertent mutations) or environmental influences (e.g., methylation or other epigenetic modifications), such that progeny may not, in fact, be identical to the parent cell, but are still included within the scope of the term as used herein, so long as the progeny retain the same functionality as that of the originally cell, cell culture, or cell line.

As used herein, the term "chimeric antigen receptor" (CAR) refers to a polypeptide construct comprising at least an extracellular antigen-binding domain, a TMD and a cytoplasmic signaling domain (also referred to as "an intracellular signaling domain" or ICD). In some cases, the cytoplasmic signaling domain includes a functional signaling domain derived from a stimulatory molecule. The stimulatory molecule often is the zeta chain associated with the T cell receptor complex. Optionally, the ICD can further include one or more functional signaling domains derived from at least one costimulatory molecule, such as e.g., 4-1BB (i.e., CD137), CD27, and/or CD28.

Generally, the CARs of the disclosure include an ectodomain and an endodomain each as defined by the host cell wall. In this regard, the terms "ectodomain" or "extracellular domain" generally refer to the portion of the CAR polypeptide outside of the cell or exterior to the membranous lipid bilayer, which may include one or more antigen recognition binding domains, an optional hinge domain, and any spacer domains exterior to the amino acid residues physically spanning the membrane. In some embodiments, the ectodomain of the CARs provided herein further include a signal peptide. Conversely, the terms "endodomain" or "intracellular domain" generally refer to the portion of the CAR polypeptide inside the cell or interior to the membranous lipid bilayer, which may also include any spacer domains interior to the amino acid residues physically spanning the membrane, as well as the ICD, which comprises one or more costimulatory signaling domains (e.g., ITAM-containing sequences, costimulatory domains, etc.).

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The polynucleotide and polypeptide sequences disclosed herein are shown using standard letter abbreviations for nucleotide bases and amino acids as set forth in 37 CFR § 1.82), which incorporates by reference WIPO Standard ST.25 (1998), Appendix 2, Tables 1-6.

The term "operably linked", as used herein, denotes a physical or functional linkage between two or more elements, e.g., polypeptide sequences or polynucleotide sequences, which permits them to operate in their intended fashion. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous. In the context of a polypeptide, e.g. CAR, "operably linked" refers to a physical linkage (e.g., directly or indirectly linked) between amino acid sequences (e.g., different domains) to provide for a described activity of the polypeptide. In the present disclosure, various domains of the polypeptides of the disclosure may be operably linked to retain proper folding, processing, targeting, expression, binding, and other functional properties of the polypeptides in the cell. Operably linked domains of the polypeptides of the disclosure may be contiguous or non-contiguous (e.g., linked to one another through a linker).

The term "percent identity" as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm-.nih.gov/BLAST. Such sequences are then said to be "substantially identical." This definition also refers to, or may be applied to, the complement of a sequence. This definition also includes sequences that have deletions and/or additions, as well as those that have substitutions. Sequence identity can be calculated using published techniques and widely available computer programs, such as the GCS program package (Devereux et al, Nucleic Acids Res. 12:387, 1984), BLASTP, BLASTN, FASTA (Atschul et al., J Mol Biol 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The term "recombinant" nucleic acid molecule, polypeptide, and cell as used herein, refers to a nucleic acid molecule, polypeptide, and cell that has been altered through human intervention. As non-limiting examples, a recombinant nucleic acid molecule can be one which: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. A non-limiting example of a recombinant protein is a chimeric antigen receptor provided herein.

As used herein, a "subject" or an "individual" includes animals, such as human (e.g., human subjects) and non-human animals. In some embodiments, a "subject" or "individual" is a patient under the care of a physician. Thus, the subject can be a human patient or an individual who has, is at risk of having, or is suspected of having a disease of interest (e.g., cancer) and/or one or more symptoms of the disease. The subject can also be an individual who is diagnosed with a risk of the condition of interest at the time of diagnosis or later. The term "non-human animals" includes all vertebrates, e.g., mammals, e.g., rodents, e.g., mice, and non-mammals, such as non-human primates, e.g., sheep, dogs, cows, chickens, amphibians, reptiles, etc.

The term "vector" is used herein to refer to a nucleic acid molecule or sequence capable of transferring or transporting another nucleic acid molecule. For example, a vector can be used as a gene delivery vehicle to transfer a gene into a cell. The transferred nucleic acid molecule is generally linked to, e.g., inserted into, the vector nucleic acid molecule. Generally, a vector is capable of replication when associated with the proper control elements. The term "vector" includes cloning vectors and expression vectors, as well as viral vectors and integrating vectors. An "expression vector" is a vector that includes a regulatory region, thereby capable of expressing DNA sequences and fragments in vitro and/or in vivo. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses. In some embodiments, a vector is a gene delivery vector.

It is understood that aspects and embodiments of the disclosure described herein include "comprising," "consisting," and "consisting essentially of" aspects and embodiments. As used herein, "comprising" is synonymous with "including", "containing", or "characterized by", and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

Headings, e.g., (a), (b), (i) etc., are presented merely for ease of reading the specification and claims. The use of headings in the specification or claims does not require the steps or elements be performed in alphabetical or numerical order or the order in which they are presented.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to", "at least", "greater than", "less than", and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Glypican-2

Glypican-2 (GPC2) is a member of the six-member glypican family of heparan sulfate (HS) proteoglycans that are attached to the cell surface by a glycosylphosphatidylinositol (GPI) anchor and play diverse roles in growth factor signaling and cancer cell growth. GPC2 is also known as cerebroglycan proteoglycan and glypican proteoglycan 2. GPC2 genomic, mRNA and protein sequences are publicly available. In addition, human Glypican 2 mRNA and protein sequences can also be found in public databases, such as, for example, NCBI Gene ID 221914, Accession numbers NM_152742, and NP_689955, respectively, which are hereby incorporated by reference. The cell surface GPC2 protein has been shown to be expressed in the nervous system, participates in cell adhesion and is believed to regulate the growth and guidance of axons.

As illustrated in the experimental data presented below, GPC2 directed CAR T-cells could prove efficacious in the treatment of a broad spectrum of pediatric and adult malignancies facing an otherwise poor prognosis. GPC2 has been recently identified as a cell surface protein several cancers, including pediatric cancers such as neuroblastoma, high grade glioma (HGG), medulloblastoma, and several other pediatric cancers and adult malignancies, which represents an opportunity for the development of new targeted immunotherapies. For example, in pediatric cancer, GPC2 has been shown to be expressed on neuroblastoma, retinoblastoma and medulloblastoma at comparable levels, while showing restricted normal tissue expression. Additionally, subsets of acute lymphoblastic leukemia, high-grade glioma and rhabdomyosarcoma express GPC2. GPC2 is also highly expressed on small cell lung cancer, a common and nearly universally lethal cancer. In addition, numerous adult malignancies could benefit from GPC2-targeted immunotherapeutics, as evaluating GPC2 expression in adult cancer utilizing data sourced from The Cancer Genome Atlas (TCGA) (see, e.g. FIG. 1). GPC2 is also highly expressed on small cell lung cancer (FIG. 1B), a common and nearly universally lethal cancer. Due to this preferential expression, GPC2 represents a potential candidate for targeted immunotherapy. It is present on the cell surface of numerous childhood and adult malignancies and demonstrates high differential expression between tumor and normal tissues.

Compositions of the Disclosure

As described in greater detail below, one aspect of the present disclosure relates to novel antibodies and CARs capable of binding a GPC2 antigen. In some embodiments, also provided are (i) recombinant nucleic acids encoding such CARs and/or antibodies, (ii) recombinant cells that have been engineered to express a CAR and/or an antibody as disclosed herein, and are directed against a cell of interest, e.g., a cancer cell.

Chimeric Antigen Receptors (CARs) Targeting Glypican-2

In one aspect, some embodiments disclosed herein relate to novel chimeric antigen receptors (CAR) which targets GPC2. CAR T-cells utilize synthetic biology to equip T-cells with a receptor that recognizes cell-surface proteins on cancer. The CARs of the disclosure generally include an antigen-binding moiety capable of binding to a GPC2 polypeptide operably linked (e.g., fused) to a TMD and an ICD. In some embodiments, the GPC2-targeting CAR of the disclosure, when expressed on the surface of an immune cell, e.g., T cells, can mediate binding of the target, activate the immune cell (e.g., T cells), and induce target cell lysis.

In some embodiments, the antigen-binding moiety includes one or more antigen-binding determinants of an antibody or a functional antigen-binding fragment thereof. One skilled in the art upon reading the present disclosure will readily understand that the term "functional fragment thereof" or "functional variant thereof" refers to a molecule having quantitative and/or qualitative biological activity in common with the wild-type molecule from which the fragment or variant was derived. For example, a functional fragment or a functional variant of an antibody is one which retains essentially the same ability to bind to the same epitope as the antibody from which the functional fragment or functional variant was derived. For instance, an antibody capable of binding to an epitope of a cell surface receptor may be truncated at the N-terminus and/or C-terminus, and the retention of its epitope binding activity assessed using assays known to those of skill in the art.

One skilled in the art will understand that the term "derived from" when used in reference to a nucleic acid or polypeptide molecule refers to the origin or source of the molecule, and may include naturally occurring, recombinant, unpurified, or purified molecules. Nucleic acid or polypeptide molecules are considered "derived from" when they include portions or elements assembled in such a way that they produce a functional unit. The portions or elements can be assembled from multiple sources provided that they retain evolutionarily conserved function. In some embodiments, the derivative nucleic acid or polypeptide molecules include substantially the same sequence as the source nucleic acid or polypeptide molecule. For example, the derivative nucleic acid or polypeptide molecules of the present disclosure may have at least 80%, 85%, 90%, 95%, 98%, 99%, or 100% sequence identity to the source nucleic acid or polypeptide molecule.

Non-limiting examples of GPC2 antigen-binding moieties suitable for the compositions and methods disclosed herein include an antibody, an antigen-binding fragment (Fab), a single-chain variable fragment (scFv), a NANOBODY®, a diabody, a triabody, a minibody, an F(ab')2 fragment, anF (ab) fragment, a VH domain, a VL domain, a single chain variable fragment (scFv), a single domain antibody (sdAb), a VNAR domain, and a VHH domain, or a functional fragment of any thereof. In some embodiments, the antigen-binding moiety includes a heavy chain variable region and a light chain variable region. In some embodiments, the antigen-binding moiety includes a scFv.

The antigen-binding moiety can include naturally-occurring amino acid sequences or can be engineered, designed, or modified so as to provide desired and/or improved properties, e.g., binding affinity. Generally, the binding affinity of an antibody or an antigen-binding moiety for a target antigen (e.g., GPC2 antigen) can be calculated by the Scatchard method described by Frankel et al., *Mol. Immunol,* 16:101-106, 1979. In some embodiments, binding affinity can be measured by an antigen/antibody dissociation rate. In some embodiments, a high binding affinity can be measured by a competition radioimmunoassay. In some embodiments, binding affinity can be measured by ELISA. In some embodiments, antibody affinity can be measured by flow cytometry. An antibody that "selectively binds" an antigen (such as GPC2) is an antibody that binds the antigen with high affinity and does not significantly bind other unrelated antigens, but binds the antigen with high affinity, e.g., with an equilibrium constant (KD) of 100 nM or less, such as 60 nM or less, for example, 30 nM or less, such as, 15 nM or less, or 10 nM or less, or 5 nM or less, or 1 nM or less, or 500 pM or less, or 400 pM or less, or 300 pM or less, or 200 pM or less, or 100 pM or less.

In some embodiments, the GPC2-targeting CAR disclosure herein includes (i) an antigen-binding moiety capable of binding to a GPC2 polypeptide (GPC2-antigen binding domain); (ii) a TMD; and (iii) an ICD. In some embodiments, the GPC2-antigen binding domain includes a GPC2 scFv region including a VH and a VL of an antibody capable of binding to a GPC2 polypeptide. One of ordinary skill in the art will appreciate that the binding of an anti-GPC2 antibody, e.g., anti-GPC2 scFv, to its GPC2 target can be either in a competitive or non-competitive fashion with a natural ligand of the GPC2 target. Accordingly, in some embodiments of the disclosure, the binding of the anti-GPC2 scFv to the GPC2 target can be ligand-blocking. In some other embodiments, the binding of the anti-GPC2 scFv to the GPC2 target does not block binding of the natural ligand. In some embodiments, the anti-GPC2 scFv region of the CAR does not include a VH or a VL sequence of SEQ ID NO: 2, SEQ ID NO: 4, SEQ ID NO: 12, SEQ ID NO: 14, SEQ ID NO: 22, or SEQ ID NO: 24 disclosed in PCT Publication No. WO/2017/083296.

Implementations of embodiments of the GPC2-targeting CAR of the disclosure can include one or more of the following features. In some embodiments, the GPC2-targeting CAR includes (i) an anti-GPC2 scFv region, (ii) a TMD, and (iii) an ICD, wherein the anti-GPC2 scFv region includes the variable heavy chain CDR 1, 2 and 3 (HCDR1, HCDR2, HCDR3) amino acid sequences as shown in SEQ ID NOS: 1, 2, and 3, respectively, wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues. In some embodiments, the amino acid substitution(s) may be a conservative amino acid substitution, for example at a non-essential amino acid residue in the CDR sequence(s). A "conservative amino acid substitution" is understood to be one in which the original amino acid residue is substituted with an amino acid residue having a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In some embodiments, the GPC2-targeting CAR includes (i) an anti-GPC2 scFv region, (ii) a TMD, and (iii) an ICD, wherein the anti-GPC2 scFv region includes the variable light chain CDR 1, 2 and 3 (LCDR1, LCDR2, LCDR3) amino acid sequences as shown in SEQ ID NOS: 4, 5, and 6, respectively, wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues.

In some embodiments, the GPC2-targeting CAR includes (i) an anti-GPC2 scFv region, (ii) a TMD, and (iii) an ICD, wherein the anti-GPC2 scFv region includes (a) the variable heavy chain CDR 1, 2 and 3 (HCDR1, HCDR2, HCDR3) amino acid sequences as shown in SEQ ID NOS: 1, 2, and 3, respectively; and (b) the variable light chain CDR 1, 2 and 3 (LCDR1, LCDR2, LCDR3) amino acid sequences as shown in SEQ ID NOS: 4, 5, and 6, respectively, wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues.

In some embodiments, the anti-GPC2 scFv region includes a VH framework region and VL framework region having at least 80% identity to the framework regions of SEQ ID NO: 7 and SEQ ID NO: 8, respectively. In some embodiments, the anti-GPC2 scFv region includes a VH framework region and VL framework region having at least 80%, at least 85%, at least 90%, at least 95% sequence identity to the framework regions of SEQ ID NO: 7 and SEQ ID NO: 8, respectively. In some embodiments, the anti-GPC2 scFv region includes a VH framework region and VL framework region having at least 95%, at least 96%, at least 97%, at least 98%, at least 99% sequence identity to the framework regions of SEQ ID NO: 7 and SEQ ID NO: 8, respectively. In some embodiments, the anti-GPC2 scFv region includes a VH framework region and VL framework region having 100% sequence identity to the framework regions of SEQ ID NO: 7 and SEQ ID NO: 8, respectively.

In some embodiments, the GPC2-targeting CAR includes (i) an anti-GPC2 scFv region, (ii) a TMD, and (iii) an ICD, wherein the anti-GPC2 scFv region includes the variable heavy chain CDR 1, 2 and 3 (HCDR1, HCDR2, HCDR3) amino acid sequences as shown in SEQ ID NOS: 10, 11, and 12, respectively, wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues.

In some embodiments, the GPC2-targeting CAR includes (i) an anti-GPC2 scFv region, (ii) a TMD, and (iii) an ICD, wherein the anti-GPC2 scFv region includes the variable light chain CDR 1, 2 and 3 (LCDR1, LCDR2, LCDR3) amino acid sequences as shown in SEQ ID NOS: 13, 14, and 15, respectively, wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues.

In some embodiments, the GPC2-targeting CAR includes (i) an anti-GPC2 scFv region, (ii) a TMD, and (iii) an ICD, wherein the anti-GPC2 scFv region includes (a) the variable heavy chain CDR 1, 2 and 3 (HCDR1, HCDR2, HCDR3) amino acid sequences as shown in SEQ ID NOS: 10, 11, and 12, respectively; and (b) the variable light chain CDR 1, 2 and 3 (LCDR1, LCDR2, LCDR3) amino acid sequences as shown in SEQ ID NOS: 13, 14, and 15, respectively, wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues.

In some embodiments, the anti-GPC2 scFv region includes a VH framework region and VL framework region having at least 80% identity to the framework regions of SEQ ID NO: 15 and SEQ ID NO: 16, respectively. In some embodiments, the anti-GPC2 scFv region includes a VH framework region and VL framework region having at least 80%, at least 85%, at least 90%, at least 95% sequence identity to the framework regions of S SEQ ID NO: 15 and SEQ ID NO: 16, respectively. In some embodiments, the anti-GPC2 scFv region includes a VH framework region and VL framework region having at least 95%, at least 96%, at least 97%, at least 98%, at least 99% sequence identity to the framework regions of SEQ ID NO: 15 and SEQ ID NO: 16, respectively. In some embodiments, the anti-GPC2 scFv region includes a VH framework region and VL framework region having 100% sequence identity to the framework regions of SEQ ID NO: 15 and SEQ ID NO: 16, respectively.

In some embodiments, the HCDRs and LCDRs of the CAR do not include the CDR sequences of SEQ ID NOS: 5-10, 15-20 and 25-30 disclosed in PCT Publication No. WO/2017/083296.

In some embodiments of the GPC2-targeting CAR disclosed herein, the VH sequence is operably linked downstream to the VL sequence. In some embodiments, the VH sequence is operably linked upstream to the VL sequence. As used herein, the term "upstream" in reference to an amino acid sequence refers to a location that is distal from a point of reference in an N-terminus to C-terminus direction of the amino acid sequence. Similarly, the term "downstream" refers to a location that is distal from a point of reference in a C-terminus to N-terminus direction of an amino acid sequence.

Generally, the TMD suitable for the GPC2-targeting CARs disclosed herein can be any one of the TMDs known in the art. Suitable TMDs include TMDs derived from membrane proteins. Non limiting examples of TMDs include TMDs derived from a T-cell receptor (TCR) alpha chain, a TCR beta chain, a TCR zeta chain, CD3 epsilon, CD4, CD5, CD8, CD9, CD16, CD22, CD27 (TNFRSF19), CD28, CD33, CD45, CD80, CD83, CD86, CD134, CD137, CD152 (CTLA4), CD154, CD279, and PD-1, and any combination thereof. Accordingly, in some embodiments, the GPC2-targeting CAR of the disclosure includes a TMD derived from a T-cell receptor (TCR) alpha chain, a TCR beta chain, a TCR zeta chain, CD3 epsilon, CD4, CD5, CD8, CD9, CD16, CD22, CD27 (TNFRSF19), CD28, CD33, CD45, CD80, CD83, CD86, CD134, CD137, CD152 (CTLA4), CD154, CD279, and PD-1, or any combination thereof. In some embodiments, the GPC2-targeting CARs of the disclosure include a TMD of a T-cell receptor (TCR) alpha chain, a TCR beta chain, a TCR zeta chain, CD3 epsilon, CD4, CD5, CD8, CD9, CD16, CD22, CD27 (TN-FRSF19), CD28, CD33, CD45, CD80, CD83, CD86, CD134, CD137, CD152 (CTLA4), CD154, CD279, and PD-1, or any combination thereof. In some embodiments, the GPC2-targeting CAR includes a TMD derived from a CD28 TMD. In some embodiments, the GPC2-targeting CAR includes a CD28 TMD. In some embodiments, the GPC2-targeting CAR includes a CD28 TMD having an amino acid sequence indicated as such in FIGS. 9-12.

In some embodiments, the ICD of the GPC2-targeting CAR disclosed herein includes a co-stimulatory domain. Generally, the co-stimulatory domain suitable for the GPC2-targeting CARs disclosed herein can be any one of the co-stimulatory domains known in the art. Examples of suitable co-stimulatory domains include, but are not limited to costimulatory domains from derived from 4-1BB (CD137), CD27 (TNFRSF7), CD28, OX40 (CD134), CD70, LFA-2 (CD2), CD5, ICAM-1 (CD54), LFA-1 (CD11a/CD18), DAP10, DAP12, inducible T-cell costimulatory (ICOS) polypeptide sequence, or any combination thereof. Accordingly, in some embodiments, the co-stimulatory domain of the GPC2-targeting CAR disclosed herein is selected from the group consisting of costimulatory domains derived from 4-1BB (CD137), CD27 (TNFRSF7), CD28, OX40 (CD134), CD70, LFA-2 (CD2), CD5, ICAM-1 (CD54), LFA-1 (CD11a/CD18), DAP10, DAP12, ICOS polypeptide sequence, or any combination thereof. In some embodiments, the co-stimulatory domain of the GPC2-targeting CAR disclosed herein includes a costimulatory domain of 4-1BB (CD137), CD27 (TNFRSF7), CD28, OX40 (CD134), CD70, LFA-2 (CD2), CD5, ICAM-1 (CD54), LFA-1 (CD11a/CD18), DAP10, DAP12, ICOS polypeptide sequence, or any combination thereof. In some embodiments, the GPC2-targeting CAR includes a co-stimulatory domain derived from a co-stimulatory 4-1BB (CD137) polypeptide sequence. In some embodiments, the GPC2-targeting CAR includes a co-stimulatory domain derived from a co-stimulatory CD28 polypeptide sequence. In some embodiments, the GPC2-targeting CAR includes a co-stimulatory CD28 polypeptide sequence. In some embodiments, the GPC2-targeting CAR includes a co-stimulatory domain having an amino acid sequence indicated as such in FIGS. 9-12.

In some embodiments, the GPC2-targeting CAR further includes an extracellular hinge domain (e.g., hinge region). The term "hinge domain" generally refers to a flexible polypeptide connector region disposed between the targeting moiety and the TMD. These sequences are generally derived from CD3, CD4, CD8, CD28 and domains of IgG subclasses (such as IgG1 and IgG4), or IgD domains. In some embodiments, the hinge domain provides structural flexibility to flanking polypeptide regions. The hinge domain may consist of natural or synthetic polypeptides. It will be appreciated by those skilled in the art that hinge domains may improve the function of the CAR by promoting optimal positioning of the antigen-binding moiety in relationship to the portion of the antigen recognized by the same. It will be appreciated that, in some embodiments, the hinge domain may not be required for optimal CAR activity. In some embodiments, a beneficial hinge domain comprising a short sequence of amino acids promotes CAR activity by facilitating antigen-binding by, e.g., relieving any steric constraints that may otherwise alter antibody binding kinetics. The sequence encoding the hinge domain may be positioned between the antigen recognition moiety and the TMD. In some embodiments, the hinge domain is operably linked downstream of the antigen-binding moiety and upstream of the TMD.

The hinge sequence can be any moiety or sequence derived or obtained from any suitable molecule. For example, in some embodiments, the hinge sequence can be derived from the human CD8a molecule or a CD28 molecule and any other receptors that provide a similar function in providing flexibility to flanking regions. The hinge domain can have a length of from about 4 amino acid (aa) to about 50 aa, e.g., from about 4 aa to about 10 aa, from about 10 aa to about 15 aa, from about aa to about 20 aa, from about 20 aa to about 25 aa, from about 25 aa to about 30 aa, from about 30 aa to about 40 aa, or from about 40 aa to about 50 aa. Suitable hinge domains can be readily selected and can be of any of a number of suitable lengths, such as from 1 amino acid (e.g., Gly) to 20 aa, from 2 aa to 15 aa, from 3 aa to 12 aa, including 4 aa to 10 aa, 5 aa to 9 aa, 6 aa to 8 aa, or 7 aa to 8 aa, and can be 1, 2, 3, 4, 5, 6, or 7 aa.

Non-limiting examples of suitable hinge domains include hinge domains derived from LFA-1 (CD11a/CD18), LFA-2 (CD2), CD4, CD5, CD8, CD27 (TNFRSF7), CD28, CD70, 4-1BB, OX40 (CD134), CD152 (CTLA4), ICOS (CD278), IgG1 Fc region, and IgG4 Fc region. Accordingly, in some embodiments, the GPC2-targeting CAR disclosed herein includes a hinge domain derived from LFA-1 (CD11a/CD18), LFA-2 (CD2), CD4, CD5, CD8, CD27 (TNFRSF7), CD28, CD70, 4-1BB, OX40 (CD134), CD152 (CTLA4), ICOS (CD278), IgG1 Fc region, IgG4 Fc region, or a combination thereof. In some embodiments, the GPC2-targeting CAR disclosed herein includes a hinge domain derived from a CD8 hinge domain, a CD28 hinge domain, a CD152 hinge domain, or an IgG4 hinge domain. In some embodiments, the hinge domain can include regions derived from a human CD8a (a.k.a. CD8a) molecule or a CD28 molecule and any other receptors that provide a similar function in providing flexibility to flanking regions. In some embodiments, the GPC2-targeting CAR disclosed herein includes a hinge domain derived from a CD8a hinge domain. In some embodiments, the GPC2-targeting CAR disclosed herein includes a hinge domain derived from a CD28 hinge domain. In some embodiments, the GPC2-targeting CAR includes a hinge domain having an amino acid sequence indicated as such in FIGS. 9-12.

In some embodiments, the CAR disclosed herein further includes an extracellular spacer domain including one or more intervening amino acid residues that are positioned between the anti-GPC2 scFv region and the extracellular hinge domain. In some embodiments, the extracellular spacer domain is operably linked downstream to the anti-GPC2 scFv region and upstream to the hinge domain. In principle, there are no particular limitations to the length and/or amino acid composition of the extracellular spacer. In some embodiments, any arbitrary single-chain peptide comprising about one to about 300 amino acid residues (e.g., 2, 3, 4, 5, 6, 7, 8, 9, 10, 11, 12, 13, 14, 15, 16, 17, 18, 19, 20, etc. amino acid residues) can be used as an extracellular spacer. In some embodiments, the extracellular spacer includes about 5 to 50, about 10 to 60, about 20 to 70, about 30 to 80, about 40 to 90, about 50 to 100, about 60 to 120, about 70 to 150, about 100 to 200, about 150 to 250, about 200 to 300, about 30 to 60, about 20 to 80, about 30 to 90 amino acid residues. In some embodiments, the extracellular spacer includes about 1 to 10, about 50 to 100, about 100 to 150, about 150 to 200, about 200 to 300, about 20 to 80, about 40 to 120, about 200 to 250 amino acid residues. In some embodiments, the extracellular spacer includes about 40 to 70, about 50 to 80, about 60 to 80, about 70 to 90, or about 80 to 100 amino acid residues. In some embodiments, the extracellular spacer includes about 1 to 10, about 5 to 15, about 10 to 20, about 15 to 25 amino acid residues. In some embodiments, the extracellular spacer includes about 220, 225, 230, 235, or 240 amino acid residues. In some embodiments, the extracellular spacer includes 229 amino acid residues. In some embodiments, the length and amino acid composition of the extracellular spacer can be optimized to vary the orientation and/or proximity of the anti-GPC2 scFv region and the extracellular hinge domain to one another to achieve a desired activity of the GPC2-targeting CAR. In some embodiments, the orientation and/or proximity of the anti-GPC2 scFv region and the extracellular hinge domain to one another can be varied and/or optimized as a "tuning" tool or effect that would enhance or reduce the efficacy of the GPC2 CAR. In some embodiments, the orientation and/or proximity of the anti-GPC2 scFv region and the extracellular hinge domain to one another can be varied and/or optimized to create a partially functional or partially functional versions of the GPC2-targeting CAR. In some embodiments, the extracellular spacer domain includes an amino acid sequence corresponding to an IgG4 hinge domain and an IgG4 CH2-CH3 domain. In some embodiments, the GPC2-targeting CAR includes an extracellular spacer domain having an amino acid sequence indicated as such in FIGS. 9-12.

In some embodiments, the ICD of the GPC2-targeting disclosed herein CAR includes a CD3ζ ICD. In some embodiments of the disclosure, the GPC2-targeting CAR includes a) an anti-GPC2 scFv region; b) a CD28 hinge domain; c) a CD28 TMD; and d) an ICD including a co-stimulatory domain derived from a 4-1BBz co-stimulatory domain or a CD28 co-stimulatory domain.

In some embodiments, the GPC2-targeting CAR includes an amino acid sequence having at least 80% sequence identity to an amino acid sequence selected from the group consisting of SEQ ID NOs: 17-25. In some embodiments, the GPC2-targeting CAR includes an amino acid sequence having at least 80%, at least 85%, at least 90%, at least 95% sequence identity to an amino acid sequence selected from the group consisting of SEQ ID NOs: 17-25. In some embodiments, the GPC2-targeting CAR includes an amino acid sequence having at least 95%, at least 96%, at least 97%, at least 98%, at least 99% sequence identity to an amino acid sequence selected from the group consisting of SEQ ID NOs: 17-25. In some embodiments, the GPC2-targeting CAR includes an amino acid sequence having 100% sequence identity to an amino acid sequence selected from the group consisting of SEQ ID NOs: 17-25.

One skilled in the art will appreciate that the complete amino acid sequence of a CAR or antibody of the disclosure can be used to construct a back-translated gene. For example, a DNA oligomer containing a nucleotide sequence coding for a given CAR or antibody can be synthesized. For example, several small oligonucleotides coding for portions of the desired CAR or antibody can be synthesized and then ligated. The individual oligonucleotides typically contain 5' or 3' overhangs for complementary assembly.

In addition to generating desired CARs or antibodies via expression of nucleic acid molecules that have been altered by recombinant molecular biological techniques, a subject CAR or antibody in accordance with the present disclosure can be chemically synthesized. Chemically synthesized polypeptides are routinely generated by those of skill in the art.

Once assembled (by synthesis, recombinant methodologies, site-directed mutagenesis or other suitable techniques), the DNA sequences encoding a CAR or antibody as disclosed herein can be inserted into an expression vector and operably linked to an expression control sequence appropriate for expression of the CAR or antibody in the desired transformed host. Proper assembly can be confirmed by nucleotide sequencing, restriction mapping, and expression of a biologically active polypeptide in a suitable host. As is known in the art, in order to obtain high expression levels of a transfected gene in a host, take should be taken to ensure that the gene is operably linked to transcriptional and translational expression control sequences that are functional in the chosen expression host.

Nucleic Acid Molecules

In one aspect, some embodiments of the disclosure relate to a recombinant nucleic acid molecule including a nucleic acid sequence that encodes a GPC2-targeting CAR as disclosed herein, or an antibody as disclosed herein.

Nucleic acid molecules of the present disclosure can be nucleic acid molecules of any length, including nucleic acid molecules that are generally between about 5 Kb and about 50 Kb, for example between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

Implementations of embodiments of the recombinant nucleic acid of the disclosure can include one or more of the following features. In some embodiments, the recombinant nucleic acid molecule includes a nucleic acid sequence encoding a CAR that includes (i) an anti-GPC2 scFv region including a VH and a VL; (ii) a TMD; and (iii) an ICD, wherein the anti-GPC2 scFv region does not include a VH or a VL sequence of SEQ ID NO: 2, SEQ ID NO: 4, SEQ ID NO: 12, SEQ ID NO: 14, SEQ ID NO: 22, or SEQ ID NO: 24 disclosed in PCT Publication No. WO/2017/083296. In some embodiments, the recombinant nucleic acid molecule includes a nucleic acid sequence encoding a CAR that includes (i) an anti-Glypican 2 scFv region, (ii) a TMD, and (iii) an ICD, wherein the anti-GPC2 scFv region includes (a) the variable heavy chain CDR 1, 2 and 3 (HCDR1, HCDR2, HCDR3) amino acid sequences as shown in SEQ ID NOS: 1, 2, and 3, respectively; and (b) the variable light chain CDR 1, 2 and 3 (LCDR1, LCDR2, LCDR3) amino acid sequences as shown in SEQ ID NOS: 4, 5, and 6, respectively, wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues. In some embodiments, the recombinant nucleic acid molecule includes a nucleic acid sequence encoding a CAR that includes a VH framework region and VL framework region having at least 80% identity to the framework regions of SEQ ID NO: 7 and SEQ ID NO: 8, respectively.

In some embodiments, the recombinant nucleic acid molecule includes a nucleic acid sequence encoding a CAR that includes (i) an anti-GPC2 scFv region, (ii) a TMD, and (iii) an ICD, wherein the anti-GPC2 scFv region includes (a) the variable heavy chain CDR 1, 2 and 3 (HCDR1, HCDR2, HCDR3) amino acid sequences as shown in SEQ ID NOS: 10, 11, and 12, respectively; and (b) the variable light chain CDR 1, 2 and 3 (LCDR1, LCDR2, LCDR3) amino acid sequences as shown in SEQ ID NOS: 13, 14, and 15, respectively, wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues. In some embodiments, the anti-GPC2 scFv region includes a VH framework region and VL framework region having at least 80% identity to the framework regions of SEQ ID NO: 15 and SEQ ID NO: 16, respectively.

In some embodiments, the HCDRs and LCDRs of the CAR do not include the CDR sequences of SEQ ID NOS: 5-10, 15-20 and 25-30 disclosed in PCT Publication No. WO/2017/083296. In some embodiments, the nucleic acid sequence has at least 80% sequence identity to a nucleic acid sequence selected from the group consisting of SEQ ID NOs: 26-33. In some embodiments, the nucleic acid sequence has at least 80%, at least 85%, at least 90%, at least 95% sequence identity to a nucleic acid sequence selected from the group consisting of SEQ ID NOs: 26-33. In some embodiments, the nucleic acid sequence has at least 95%, at least 96%, at least 97%, at least 98%, at least 99% sequence identity to a nucleic acid sequence selected from the group consisting of SEQ ID NOs: 26-33. In some embodiments, the nucleic acid sequence has 100% sequence identity to a nucleic acid sequence selected from the group consisting of SEQ ID NOs: 26-33.

In some embodiments, the recombinant nucleic acid molecule is operably linked to a heterologous nucleic acid sequence, such as, for example a structural gene that encodes a protein of interest or a regulatory sequence (e.g., promoter sequence). In some embodiments, the recombinant nucleic acid molecule is further defined as an expression cassette or a vector. In some embodiments, the vector is a lentiviral vector, an adeno virus vector, an adeno-associated virus vector, a baculovirus, or a retroviral vector.

Some embodiments disclosed herein relate to vectors or expression cassettes including a recombinant nucleic acid molecule as disclosed herein. As used herein, the term "expression cassette" refers to a construct of genetic material that contains coding sequences and enough regulatory information to direct proper transcription and/or translation of the coding sequences in a recipient cell, in vivo and/or ex vivo. The expression cassette may be inserted into a vector for targeting to a desired host cell and/or into a subject. As such, the term expression cassette may be used to refer to an expression construct.

Also provided herein are vectors, plasmids or viruses containing one or more of the nucleic acid molecules encoding any of the GPC2-targeting CARs disclosed herein. The nucleic acid molecules described above can be contained within a vector that is capable of directing their expression in, for example, a cell that has been transformed/transduced with the vector. Suitable vectors for use in eukaryotic and prokaryotic cells are known in the art and are commercially available, or readily prepared by a skilled artisan. Additional vectors can also be found in, for example, Ausubel, F. M., et al. (2014, supra) and Sambrook et al. (2012, supra).

It should be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, vectors that can be used include those that allow the DNA encoding the GPC2-targeting CARs of the present disclosure to be amplified in copy number. Such amplifiable vectors are known in the art. They include, for example, vectors able to be amplified by DHFR amplification (see, e.g., Kaufman, U.S. Pat. No. 4,470,461) or glutamine synthetase ("GS") amplification (see, e.g., U.S. Pat. No. 5,122,464 and European published application EP 338,841).

Accordingly, in some embodiments, the GPC2-targeting CARs of the present disclosure can be expressed from vectors, generally expression vectors. The vectors are useful for autonomous replication in a host cell or may be integrated into the genome of a host cell upon introduction into the host cell, and thereby are replicated along with the host genome (e.g., non-episomal mammalian vectors). Expression vectors are capable of directing the expression of coding sequences to which they are operably linked. In general, expression vectors of utility in recombinant DNA techniques are often in the form of plasmids (vectors). However, other forms of expression vectors, such as viral vectors (e.g., replication defective retroviruses, adenoviruses, and adeno-associated viruses) are also included.

Exemplary recombinant expression vectors can include one or more regulatory sequences, selected on the basis of the host cells to be used for expression, operably linked to the nucleic acid sequence to be expressed.

DNA vector can be introduced into prokaryotic or eukaryotic cells via conventional transformation or transfection techniques. Suitable methods for transforming or transfecting host cells can be found in, for example, Sambrook et al. (2012) *Molecular Cloning: A Laboratory Manual* (2nd ed., Cold Spring Harbor Laboratory Press, Plainview, N. Y.) and other standard molecular biology laboratory manuals.

The nucleic acid sequences encoding the GPC2-targeting CARs of the present disclosure can be optimized for expression in the host cell of interest. For example, the G-C content of the sequence can be adjusted to levels average for a given cellular host, as calculated by reference to known genes expressed in the host cell. Methods for codon optimization are known in the art. Codon usages within the coding sequence of the GPC2-targeting CARs disclosed herein can be optimized to enhance expression in the host cell, such that about 1%, about 5%, about 10%, about 25%, about 50%, about 75%, or up to 100% of the codons within the coding sequence have been optimized for expression in a particular host cell.

Vectors suitable for use include T7-based vectors for use in bacteria, the pMSXND expression vector for use in mammalian cells, and baculovirus-derived vectors for use in insect cells. In some embodiments nucleic acid inserts, which encode the subject GPC2-targeting CAR in such vectors, can be operably linked to a promoter, which is selected based on, for example, the cell type in which expression is sought.

In selecting an expression control sequence, a variety of factors should also be considered. These include, for example, the relative strength of the sequence, its controllability, and its compatibility with the actual DNA sequence encoding the subject GPC2-targeting CAR, particularly as regards potential secondary structures. Hosts should be selected by consideration of their compatibility with the chosen vector, the toxicity of the product coded for by the DNA sequences of this disclosure, their secretion characteristics, their ability to fold the polypeptides correctly, their fermentation or culture requirements, and the ease of purification of the products coded for by the DNA sequences.

Within these parameters one of skill in the art may select various vector/expression control sequence/host combinations that will express the desired DNA sequences on fermentation or in large scale animal cell culture, for example, using CHO cells or COS 7 cells.

The T choice of expression control sequence and expression vector, in some embodiments, will depend upon the choice of host. A wide variety of expression host/vector combinations can be employed. Non-limiting examples of useful expression vectors for eukaryotic hosts, include, for example, vectors with expression control sequences from SV40, bovine papilloma virus, adenovirus and cytomegalovirus. Non-limiting examples of useful expression vectors for bacterial hosts include known bacterial plasmids, such as plasmids from *E. coli*, including col El, pCRI, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Non-limiting examples of useful expression vectors for yeast cells include the 2u plasmid and derivatives thereof. Non-limiting examples of useful vectors for insect cells include pVL 941 and pFastBac™ 1.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans will readily appreciate numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the disclosure include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes a subject CAR disclosed herein are also features of the disclosure. A cell of the disclosure is a transfected cell, e.g., a cell into which a nucleic acid molecule, for example a nucleic acid molecule encoding a CAR targeting GPC2, has been introduced by means of recombinant DNA techniques. The progeny of such a cell are also considered within the scope of the disclosure.

Viral vectors that can be used in the disclosure include, for example, retrovirus vectors, adenovirus vectors, and adeno-associated virus vectors, lentivirus vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.). For example, a GPC2-targeting CAR or antibody as disclosed herein can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, care should be taken to ensure that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N. Y., 1993) and Pouwels et al. (Cloning Vectors: A Laboratory Manual, 1985 Suppl. 1987).

The expressed polypeptides (e.g., antibodies and CARs) can be purified from the expression system using routine biochemical procedures, and can be used, e.g., as therapeutic agents, as described herein.

In some embodiments, GPC2-targeting CARs obtained will be glycosylated or unglycosylated depending on the host organism used to produce the GPC2-targeting CARs. If bacteria are chosen as the host then the GPC2-targeting CAR produced will be unglycosylated. Eukaryotic cells, on the other hand, will glycosylate the GPC2-targeting CARs, although perhaps not in the same way as native polypeptides is glycosylated. The GPC2-targeting CARs produced by the transformed host can be purified according to any suitable methods known in the art. Produced GPC2-targeting CARs can be isolated from inclusion bodies generated in bacteria such as *E. coli*, or from conditioned medium from either mammalian or yeast cultures producing a given GPC2-targeting CAR using cation exchange, gel filtration, and or reverse phase liquid chromatography.

In addition or alternatively, another exemplary method of constructing a DNA sequence encoding the GPC2-targeting CARs of the disclosure is by chemical synthesis. This includes direct synthesis of a peptide by chemical means of the protein sequence encoding for a GPC2-targeting CAR exhibiting the properties described. This method can incorporate both natural and unnatural amino acids at positions that affect the binding affinity of the GPC2-targeting CAR with the target protein (e.g., GPC2 polypeptide). Alternatively, a gene which encodes the desired GPC2-targeting CAR can be synthesized by chemical means using an oligonucleotide synthesizer. Such oligonucleotides are designed based on the amino acid sequence of the desired GPC2-targeting CAR, and suitably selecting those codons that are favored in the host cell in which the recombinant GPC2-targeting CAR will be produced. In this regard, it is well recognized in the art that the genetic code is degenerate-that an amino acid may be coded for by more than one codon. For example, Phe (F) is coded for by two codons, TTC or TTT, Tyr (Y) is coded for by TAC or TAT and his (H) is coded for by CAC or CAT. Trp (W) is coded for by a single codon, TGG. Accordingly, it will be appreciated by those skilled in the art that for a given DNA sequence encoding a particular GPC2-targeting CAR, there will be many DNA degenerate sequences that will code for that GPC2-targeting CAR. For example, it will be appreciated that in addition to the DNA sequences for GPC2-targeting CARs provided in the Sequence Listing, there will be many degenerate DNA sequences that code for the GPC2-targeting CARs disclosed herein. These degenerate DNA sequences are considered within the scope of this disclosure. Therefore, "degenerate variants thereof" in the context of this disclosure means all DNA sequences that code for and thereby enable expression of a particular GPC2-targeting CAR.

The DNA sequence encoding the subject GPC2-targeting CAR, whether prepared by site directed mutagenesis, chemical synthesis or other methods, can also include DNA sequences that encode a signal sequence. Such signal sequence, if present, should be one recognized by the cell chosen for expression of the GPC2-targeting CAR. It can be prokaryotic, eukaryotic or a combination of the two. In general, the inclusion of a signal sequence depends on whether it is desired to secrete the GPC2-targeting CAR as disclosed herein from the recombinant cells in which it is made. If the chosen cells are prokaryotic, it generally is preferred that the DNA sequence not encode a signal sequence. If the chosen cells are eukaryotic, it generally is preferred that a signal sequence be included.

The nucleic acid molecules provided can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (e.g, either a sense or an antisense strand).

The nucleic acid molecules are not limited to sequences that encode polypeptides; some or all of the non-coding sequences that lie upstream or downstream from a coding sequence (e.g., the coding sequence of an antibody or CAR) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Exemplary isolated nucleic acid molecules of the present disclosure can include fragments not found as such in the natural state. Thus, this disclosure encompasses recombinant molecules, such as those in which a nucleic acid sequence (for example, a sequence encoding an antibody or CAR) is incorporated into a vector (e.g., a plasmid or viral vector) or into the genome of a heterologous cell (or the genome of a homologous cell, at a position other than the natural chromosomal location).

Antibodies Targeting Glypican-2

In one aspect, some embodiments disclosed herein relate to an isolated antibody or a functional fragment thereof that selectively binds GPC2. In some embodiments, the antibody includes an antigen-binding moiety which includes one or more complementarity determining regions (CDRs) having the sequences as shown in SEQ ID NOS: 1-6 and 9-14, wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues The term "functional fragment" of an antibody generally refers to a part (a partial fragment) of an antibody as defined above, e.g., an antibody fragment having qualitative biological activity in common with a full-length antibody. Non-limiting examples of such functional fragment include-F(ab')2, Fab', Fab, Fv, Fvs with disulfide bond, single chain fragment (scFv), and polymers thereof. In some embodiments, the antibody is a single domain antibody. A "single-domain antibody" refers to an antibody having a single domain (a variable domain) that is capable of selectively binding an antigen, or an epitope of an antigen, in the absence of an additional antibody domain. Single-domain antibodies include, for example, VH domain antibodies, VNAR antibodies, camelid VHH antibodies, and VL domain antibodies. In some embodiments, the antibody a single-chain antibody fragment (scFv). In some embodiments, the antibody is a mouse antibody. In some embodiments, the antibody is a chimeric, human or humanized antibody. In some embodiments, the antibody is a non-naturally occurring antibody.

In some embodiments, the antibody of the disclosure is selected from the group consisting of: (a) an antibody having a VH and VL region having at least 80% sequence identity to SEQ ID NO: 7 and SEQ ID NO: 8 (GPC2.19), respectively; and (b) an antibody having a VH and VL region having at least 80% sequence identity to SEQ ID NO: 15 and SEQ ID NO: 16 (GPC2.27), respectively. In some embodiments, the antibody includes a VH and VL region having at least 80%, at least 85%, at least 90%, at least 95% sequence identity to SEQ ID NO: 7 and SEQ ID NO: 8, respectively. In some embodiments, the antibody includes a VH and VL region having at least 95%, at least 96%, at least 97%, at least 98%, at least 99% sequence identity to SEQ ID NO: 7 and SEQ ID NO: 8, respectively. In some embodiments, the antibody includes a VH and VL region having 100% sequence identity to SEQ ID NO: 7 and SEQ ID NO: 8, respectively. In some embodiments, the antibody includes a VH and VL region having at least 80%, at least 85%, at least 90%, at least 95% sequence identity to S SEQ ID NO: 15 and SEQ ID NO: 16, respectively. In some embodiments, the antibody includes a VH and VL region having at least 95%, at least 96%, at least 97%, at least 98%, at least 99% sequence identity to SEQ ID NO: 15 and SEQ ID NO: 16, respectively. In some embodiments, the antibody includes a VH and VL region having 100% sequence identity to SEQ ID NO: 15 and SEQ ID NO: 16, respectively.

In some embodiments, the antibody is an antibody having the variable heavy chain CDR 1, 2 and 3 (HCDR1, HCDR2, HCDR3) amino acid sequences as shown in SEQ ID NOS: 1, 2, and 3, respectively (GPC2.19), wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues.

In some embodiments, the antibody is an antibody having the variable light chain CDR 1, 2 and 3 (LCDR1, LCDR2, LCDR3) amino acid sequences as shown in SEQ ID NOS: 4, 5, and 6, respectively (GPC2.19), wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues.

In some embodiments, the antibody comprises a VH framework region and VL framework region having at least 80% identity to the framework regions of SEQ ID NO: 7 and SEQ ID NO: 8 (GPC2.19), respectively. In some embodiments, the antibody comprises a VH framework region and VL framework region having at least 80%, at least 85%, at least 90%, at least 95% sequence identity to the framework regions of SEQ ID NO: 7 and SEQ ID NO: 8, respectively. In some embodiments, the antibody comprises a VH framework region and VL framework region having at least 95%, at least 96%, at least 97%, at least 98%, at least 99% sequence identity to the framework regions of SEQ ID NO: 7 and SEQ ID NO: 8, respectively. In some embodiments, the antibody comprises a VH framework region and VL framework region having 100% sequence identity to the framework regions of SEQ ID NO: 7 and SEQ ID NO: 8, respectively.

In some embodiments, the antibody is an antibody having the variable heavy chain CDR 1, 2 and 3 (HCDR1, HCDR2, HCDR3) amino acid sequences as shown in SEQ ID NOS: 9, 10, and 11, respectively (GPC2.27), wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues.

In some embodiments, the antibody is an antibody having the variable light chain CDR 1, 2 and 3 (LCDR1, LCDR2, LCDR3) amino acid sequences as shown in SEQ ID NOS:

12, 13, and 14, respectively (GPC2.27), wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues.

In some embodiments, the antibody comprises a VH framework region and VL framework region having at least 80% identity to the framework regions of SEQ ID NO: 15 and SEQ ID NO: 16 (GPC2.27), respectively. In some embodiments, the antibody comprises a VH framework region and VL framework region having at least 80%, at least 85%, at least 90%, at least 95% sequence identity to the framework regions of SEQ ID NO: 15 and SEQ ID NO: 16, respectively. In some embodiments, the antibody comprises a VH framework region and VL framework region having at least 95%, at least 96%, at least 97%, at least 98%, at least 99% sequence identity to the framework regions of SEQ ID NO: 15 and SEQ ID NO: 16, respectively. In some embodiments, the antibody comprises a VH framework region and VL framework region having 100% sequence identity to the framework regions of SEQ ID NO: 15 and SEQ ID NO: 16, respectively.

In a related aspect, some embodiments relate to a CAR including an antigen-binding region of the anti-GPC2 antibody described herein. In some embodiments, the CAR includes an anti-GPC2 single-chain antibody fragment (scFv) as described herein. In some embodiments, the CAR includes an antigen-binding moiety derived from an antibody as described herein.

Figure 2A:
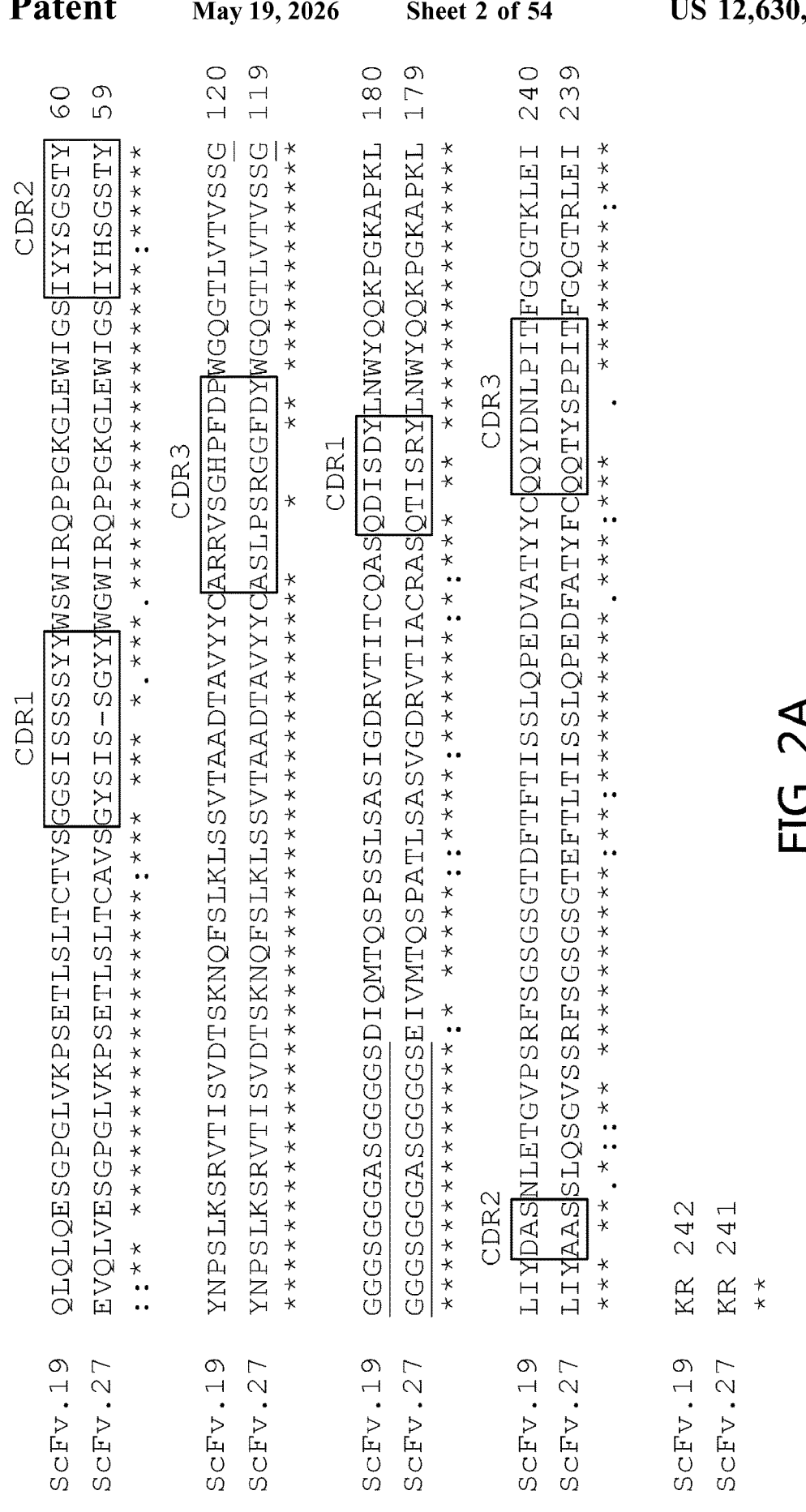
FIGS. 2A-2H schematically summarize the results of experiments performed to prioritize GPC2-targeting scFv's for utilization in CAR T-cell constructs.

The locations of the CDRs, using both the Kabat and IMGT numbering schemes, are provided in the Sequence Listing and FIG. 2A. However, one of skill in the art could readily determine the CDR boundaries using alternative numbering schemes, such as the Chothia numbering scheme. In the amino acids sequences of FIG. 2A, the CDR regions according to Kabat scheme are highlighted.

In some embodiments, the antibody is a derivative of the disclosed antibodies, e.g., an antibody comprising the CDR sequences substantially identical to those in the antibodies disclosed herein (e.g., a chimeric, humanized or CDR-grafted antibody). In some embodiments, the antibody is a fully human recombinant antibody. The present disclosure also contemplates isotype modification. By modifying the Fc region to have a different isotype, different functionalities can be achieved. For example, changing to IgG4 can reduce immune effector functions associated with other isotypes. Modified antibodies may be made by any technique known to those of skill in the art, including expression through standard molecular biological techniques, or the chemical synthesis of polypeptides.

Also provided herein are antibody-drug conjugates (ADCs) that include a drug conjugated to an antibody disclosed herein or antigen-binding fragment thereof. In some embodiments, the drug is a small molecule. In some embodiments, the drug is an anti-microtubule agent, anti-cancer agent, an anti-mitotic agent and/or a cytotoxic agent.

Further disclosed herein are multi-specific antibodies that include an antibody described herein or an antigen-binding fragment thereof and at least one additional monoclonal antibody or antigen-binding fragment thereof. In some embodiments, the multi-specific antibody is a bispecific antibody. In other embodiments, the multi-specific antibody is a trispecific antibody. In some examples, the at least one additional monoclonal antibody or antigen binding fragment thereof specifically binds a component of the T cell receptor or a natural killer (NK) cell activating receptor.

Further provided herein are CARs that include an antibody disclosed herein or an antigen-binding fragment thereof. In some embodiments, the CAR further includes one or more of a hinge domain, a TMD, a costimulatory signaling moiety, and a signaling domain. In some examples, the hinge domain includes a CD8a hinge domain. In some examples, the TMD includes a CD8a or a CD28 TMD. In some examples, the costimulatory signaling moiety comprises a 4-1BB and/or a CD28 signaling moiety. In some examples, the signaling domain comprises a CD32 signaling domain.

Recombinant Cells and Cell Cultures

The nucleic acid molecule of the present disclosure can be introduced into a host cell, such as a human T cell or cancer cell, to produce a recombinant cell containing the nucleic acid molecule. Accordingly, some embodiments of the disclosure relate to methods for making a recombinant cell, including (a) providing a host cell capable of protein expression; and transducing the provided host cell with a recombinant nucleic acid of the disclosure to produce a recombinant cell. Introduction of the nucleic acid molecules of the disclosure into cells can be achieved by methods known to those skilled in the art such as, for example, viral infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Accordingly, in some embodiments, the nucleic acid molecules can be introduced into a host cell by viral or non-viral delivery vehicles known in the art to produce a recombinant cell. For example, the nucleic acid molecule can be stably integrated in the host genome, or can be episomally replicating, or present in the recombinant host cell as a mini-circle expression vector for a stable or transient expression. Accordingly, in some embodiments disclosed herein, the nucleic acid molecule is maintained and replicated in the recombinant host cell as an episomal unit. In some embodiments, the nucleic acid molecule is stably integrated into the genome of the recombinant cell. Stable integration can be completed using classical random genomic recombination techniques or with more precise genome editing techniques such as using zinc-finger proteins (ZNF), guide RNA directed CRISPR/Cas9, DNA-guided endonuclease genome editing NgAgo (*Natronobacterium gregoryi* Argonaute), or TALEN genome editing (transcription activator-like effector nucleases).

The nucleic acid molecules can be encapsulated in a viral capsid or a lipid nanoparticle, or can be delivered by viral or non-viral delivery means and methods known in the art, such as electroporation. For example, introduction of nucleic acids into cells may be achieved by viral transduction. In a non-limiting example, baculoviral virus or adeno-associated virus (AAV) can be engineered to deliver nucleic acids to target cells via viral transduction. Several AAV serotypes have been described, and all of the known serotypes can infect cells from multiple diverse tissue types. AAV is capable of transducing a wide range of species and tissues in vivo with no evidence of toxicity, and it generates relatively mild innate and adaptive immune responses.

Lentiviral-derived vector systems are also useful for nucleic acid delivery and gene therapy via viral transduction. Lentiviral vectors offer several attractive properties as gene-delivery vehicles, including: (i) sustained gene delivery through stable vector integration into host genome; (ii) the capability of infecting both dividing and non-dividing cells; (iii) broad tissue tropisms, including important gene- and cell-therapy-target cell types; (iv) no expression of viral proteins after vector transduction; (v) the ability to deliver complex genetic elements, such as polycistronic or intron-containing sequences; (vi) a potentially safer integration site profile; and (vii) a relatively easy system for vector manipulation and production.

In some embodiments, host cells can be genetically engineered (e.g., transduced or transformed or transfected) with, for example, a vector construct of the present application that can be, for example, a viral vector or a vector for homologous recombination that includes nucleic acid sequences homologous to a portion of the genome of the host cell, or can be an expression vector for the expression of the polypeptides of interest. Host cells can be either untransformed cells or cells that have already been transfected with at least one nucleic acid molecule.

In some embodiments, the recombinant cell is a prokaryotic cell or a eukaryotic cell. In some embodiments, the cell is in vivo. In some embodiments, the cell is ex vivo. In some embodiments, the cell is in vitro. In some embodiments, the recombinant cell is an animal cell. In some embodiments, the animal cell is a mammalian cell. In some embodiments, the animal cell is a mouse cell. In some embodiments, the animal cell is a human cell. In some embodiments, the cell is a non-human primate cell. In some embodiments, the recombinant cell is an immune system cell, e.g., a B cell, a monocyte, a NK cell, a natural killer T (NKT) cell, a basophil, an eosinophil, a neutrophil, a dendritic cell, a macrophage, a regulatory T cell, a helper T cell ($T_H$), a cytotoxic T cell ($T_{CTL}$), a memory T cell, a gamma delta ($\gamma\delta$) T cell, another T cell, a hematopoietic stem cell, or a hematopoietic stem cell progenitor.

In some embodiments, the immune system cell is a lymphocyte. In some embodiments, the lymphocyte is a T lymphocyte. In some embodiments, the lymphocyte is a T lymphocyte progenitor. In some embodiments, the T lymphocyte is a CD4+ T cell or a CD8+ T cell. In some embodiments, the T lymphocyte is a CD8+T cytotoxic lymphocyte cell. Non-limiting examples of CD8+T cytotoxic lymphocyte cell suitable for the compositions and methods disclosed herein include naïve CD8+ T cells, central memory CD8+ T cells, effector memory CD8+ T cells, effector CD8+ T cells, CD8+ stem memory T cells, and bulk CD8+ T cells. In some embodiments, the T lymphocyte is a CD4+T helper lymphocyte cell. Suitable CD4+T helper lymphocyte cells include, but are not limited to, naïve CD4+ T cells, central memory CD4+ T cells, effector memory CD4+ T cells, effector CD4+ T cells, CD4+ stem memory T cells, and bulk CD4+ T cells.

As outlined above, some embodiments of the disclosure relate to various methods for making a recombinant cell, including (a) providing a host cell capable of protein expression; and transducing the provided host cell with a recombinant nucleic acid of the disclosure to produce a recombinant cell. Non-limiting exemplary embodiments of the disclosed methods for making a recombinant cell can further include one or more of the following features. In some embodiments, the host cell is obtained by leukapheresis performed on a sample obtained from a subject, and the cell is transduced ex vivo. In some embodiments, the recombinant nucleic acid is encapsulated in a viral capsid or a lipid nanoparticle. In some embodiments, the methods further include isolating and/or purifying the produced cells. Accordingly, the recombinant cells produced by the methods disclosed herein are also within the scope of the disclosure.

Techniques for transforming a wide variety of the above-mentioned host cells and species are known in the art and described in the technical and scientific literature. For example, DNA vectors can be introduced into eukaryotic cells via conventional transformation or transfection techniques. Suitable methods for transforming or transfecting cells can be found in Sambrook et al. (2012, supra) and other standard molecular biology laboratory manuals, such as, calcium phosphate transfection, DEAE-dextran mediated transfection, transfection, microinjection, cationic lipid-mediated transfection, electroporation, transduction, scrape loading, ballistic introduction, nucleoporation, hydrodynamic shock, and infection. In some embodiments, the nucleic acid molecule is introduced into a host cell by a transduction procedure, electroporation procedure, or a biolistic procedure. Accordingly, cell cultures including at least one recombinant cell as disclosed herein are also within the scope of this application. Methods and systems suitable for generating and maintaining cell cultures are known in the art.

In one aspect, some embodiments of the disclosure relate to a recombinant cell including: (a) a CAR as described herein; and/or a nucleic acid molecule according as described herein. In some embodiments, the recombinant cell of the disclosure includes a nucleic acid molecule encoding a CAR that includes (i) an anti-GPC2 scFv region including a VH and a VL; (ii) a TMD; and (iii) an ICD, wherein the anti-GPC2 scFv region does not include a VH or a VL sequence of SEQ ID NO: 2, SEQ ID NO: 4, SEQ ID NO: 12, SEQ ID NO: 14, SEQ ID NO: 22, or SEQ ID NO: 24 disclosed in PCT Publication No. WO/2017/083296.

In some embodiments, the recombinant cell includes a nucleic acid molecule including a nucleic acid sequence encoding a CAR that includes (i) an anti-GPC2 scFv region, (ii) a TMD, and (iii) an ICD, wherein the anti-GPC2 scFv region includes (a) the variable heavy chain CDR 1, 2 and 3 (HCDR1, HCDR2, HCDR3) amino acid sequences as shown in SEQ ID NOS: 1, 2, and 3, respectively; and (b) the variable light chain CDR 1, 2 and 3 (LCDR1, LCDR2, LCDR3) amino acid sequences as shown in SEQ ID NOS: 4, 5, and 6, respectively, wherein one, two, three, four, or five of the amino acid residues in any one of the CDRs is optionally substituted by a different amino acid residue. In some embodiments, the recombinant cell includes a nucleic acid molecule including a nucleic acid sequence encoding a CAR that includes a VH framework region and VL framework region having at least 80% identity to the framework regions of SEQ ID NO: 7 and SEQ ID NO: 8, respectively.

In some embodiments, the recombinant cell includes a nucleic acid molecule including a nucleic acid sequence encoding a CAR that includes (i) an anti-GPC2 scFv region, (ii) a TMD, and (iii) an ICD, wherein the anti-GPC2 scFv region includes (a) the variable heavy chain CDR 1, 2 and 3 (HCDR1, HCDR2, HCDR3) amino acid sequences as shown in SEQ ID NOS: 10, 11, and 12, respectively; and (b)

the variable light chain CDR 1, 2 and 3 (LCDR1, LCDR2, LCDR3) amino acid sequences as shown in SEQ ID NOS: 13, 14, and 15, respectively, wherein one, two, three, four, or five of the amino acid residues in any one of the CDRs is optionally substituted by a different amino acid residue. In some embodiments, one amino acid residue in any one of the CDRs is optionally substituted by a different amino acid residue. In some embodiments, two amino acid residues in any one of the CDRs are optionally substituted by different amino acid residues. In some embodiments, three amino acid residues in any one of the CDRs are optionally substituted by different amino acid residues. In some embodiments, three amino acid residues in any one of the CDRs are optionally substituted by different amino acid residues. In some embodiments, four amino acid residues in any one of the CDRs are optionally substituted by different amino acid residues. In some embodiments, five amino acid residues in any one of the CDRs are optionally substituted by different amino acid residues.

In some embodiments, the recombinant cell includes a nucleic acid molecule including a nucleic acid sequence encoding a CAR that includes (i) a VH framework region and VL framework region having at least 80% identity to the framework regions of SEQ ID NO: 15 and SEQ ID NO: 16, respectively.

In some embodiments, the recombinant cell includes a nucleic acid molecule including a nucleic acid sequence encoding a CAR, wherein the HCDRs and LCDRs of the GPC2-targeting CAR do not include the CDR sequences of SEQ ID NOS: 5-10, 15-20 and 25-30 disclosed in PCT Publication No. WO/2017/083296. In some embodiments, the recombinant cell includes a nucleic acid molecule including a nucleic acid sequence having at least 80% sequence identity to a nucleic acid sequence selected from the group consisting of SEQ ID NOs: 26-33.

In a related aspect, some embodiments of the disclosure relate to a cell culture including at least one recombinant cell as disclosed herein, and a culture medium. Generally, the culture medium can be any one of suitable culture media for the cell cultures described herein. In some embodiments, the recombinant cell expresses a GPC2-targeting CAR described herein. Accordingly, cell cultures including at least one recombinant cell as disclosed herein are also within the scope of this application. Methods and systems suitable for generating and maintaining cell cultures are known in the art.

Pharmaceutical Compositions

The antibodies, CARs, nucleic acids, recombinant cells, and/or cell cultures of the disclosure can be incorporated into compositions, including pharmaceutical compositions. Such compositions generally include the antibodies, CARs, nucleic acids, recombinant cells, and/or cell cultures as described herein and a pharmaceutically acceptable carrier. Accordingly, in one aspect, some embodiments of the disclosure relate to pharmaceutical compositions for treating, preventing, ameliorating, reducing or delaying the onset of health condition, for example a proliferative disease (e.g., cancer). In some embodiments, the pharmaceutical composition includes at least one antibody, CAR, nucleic acid, recombinant cell, and/or cell culture as disclosed herein, in an admixture with a pharmaceutically acceptable carrier.

In certain embodiments, the pharmaceutical compositions in accordance with some embodiments disclosed herein include cell cultures that can be washed, treated, combined, supplemented, or otherwise altered prior to administration to an individual in need thereof. Furthermore, administration can be at varied doses, time intervals or in multiple administrations.

The pharmaceutical compositions provided herein can be in any form that allows for the composition to be administered to an individual. In some specific embodiments, the pharmaceutical compositions are suitable for human administration. As used herein, the term "pharmaceutically acceptable" means approved by a regulatory agency of the Federal or a state government or listed in the U.S. Pharmacopeia or other generally recognized pharmacopeia for use in animals, and more particularly in humans. The carrier can be a diluent, adjuvant, excipient, or vehicle with which the pharmaceutical composition is administered. Saline solutions and aqueous dextrose and glycerol solutions can also be employed as liquid carriers, including injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. In some embodiments, the pharmaceutical composition is sterilely formulated for administration into an individual. In some embodiments, the individual is a human. One of ordinary skilled in the art will appreciate that the formulation should suit the mode of administration.

In some embodiments, the pharmaceutical compositions of the present disclosure are formulated to be suitable for the intended route of administration to an individual. For example, the pharmaceutical composition may be formulated to be suitable for parenteral, intrapleural, inhalation, intraperitoneal, oral, intradermal, colorectal, intraperitoneal, and intratumoral administration. In some embodiments, the pharmaceutical composition may be formulated for intravenous, oral, intraperitoneal, intranasal, intratracheal, subcutaneous, intramuscular, topical, pulmonary, or intratumoral administration.

Methods of Treatment

Administration of any one of the therapeutic compositions described herein, e.g., antibodies, CARs, nucleic acids, recombinant cells, cell cultures, and/or pharmaceutical compositions, can be used in the treatment of relevant conditions, such as health disorders and proliferative diseases (e.g., cancer). In some embodiments, the antibodies, CARs, nucleic acids, recombinant cells, cell cultures, and/or pharmaceutical compositions as described herein can be incorporated into therapeutic agents for use in methods of treating an individual who has, who is suspected of having, or who may be at high risk for developing one or more health conditions associated with Glypican-2, such as health disorders and proliferative diseases (e.g., cancers). In some embodiments, the individual is a patient under the care of a physician. In some embodiments, the one or more health conditions includes a cancer. In some embodiments, the cancer is a pediatric cancer. In some embodiments, the pediatric cancer can be a cancer that develops in children ages 0 to 14. Examples of pediatric cancers suitable for the treatment methods disclosed herein include, but are not limited to, neuroblastoma, acute lymphoblastic leukemia (ALL), embryonal rhabdomyosarcoma (ERMS), alveolar rhabdomyosarcoma (ARMS), Ewing's sarcoma, (EWS) desmoplastic small round cell tumor (DRCT), osteosarcoma, brain and other CNS tumors, Wilm's tumor, non-Hodgkin lymphoma, and retinoblastoma. In some embodiments, the cancer is an adult malignancy.

In some embodiments, therapeutic agents described herein, e.g., antibodies, CARs, nucleic acids, recombinant cells, cell cultures, and/or pharmaceutical compositions, can be used in methods of treating individual who have, who are suspected of having, or who may be at high risk for developing a cancer expressing the GPC2 antigen (e.g., a GPC2-positive cancer). In some embodiments, the cancer overexpresses the GPC2 antigen. In some embodiments, the GPC2-positive cancer is a leukemia. In these instances, the leukemia can generally be of any type of leukemia. Suitable leukemia that can be treated using the compositions described herein (e.g., antibodies, CARs, nucleic acids, recombinant cells, cell cultures, and/or pharmaceutical compositions) include, but are not limited to, acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), and hairy cell leukemia. In some embodiments, the leukemia is AML.

In some embodiments, the therapeutic agents described herein, e.g., antibodies, CARs, nucleic acids, recombinant cells, cell cultures, and/or pharmaceutical compositions, can be used in methods of treating individual who have, who are suspected of having, or who may be at high risk for developing a GPC2-positive cancer which is a solid tumor cancer. In some embodiments, the solid tumor cell is lung cancer, liver cancer, pancreatic cancer, stomach cancer, colon cancer, kidney cancer, brain cancer, head and neck cancer, breast cancer, skin cancer, rectal cancer, uterine cancer, cervical cancer, ovarian cancer, testicular cancer, skin cancer, or esophageal cancer. In some embodiments, the cancer includes a sarcoma cell, a rhabdoid cancer cell, a neuroblastoma cell, retinoblastoma cell, or a medulloblastoma cell. In some embodiments, the GPC2-positive cancer is uterine carcinosarcoma (UCS), brain lower grade glioma (LGG), thymoma (THYM), testicular germ cell tumors (TGCT), glioblastoma multiforme (GBM) and skin cutaneous melanoma (SKCM), liver hepatocellular carcinoma (LIHC), uveal melanoma (UVM), kidney chromophobe (KICH), thyroid cancer (THCA), kidney renal clear cell carcinoma (KIRC), kidney renal papillary cell carcinoma (KIRP), stomach adenocarcinoma (STAD), cholangiocarcinoma (CHOL), adenoid cystic carcinoma (ACC), prostate adenocarcinoma (PRAD), pheochromocytoma and paraganglioma (PCPG), DLBC, lung adenocarcinoma (LUAD), small-cell lung cancer (SCLC), head-neck squamous cell carcinoma (HNSC), pancreatic adenocarcinoma (PAAD), breast cancer (BRCA), mesothelioma (MESO), colon and rectal adenocarcinoma (COAD), rectum adenocarcinoma (READ), esophageal carcinoma (ESCA), ovarian cancer (OV), lung squamous cell carcinoma (LUSC), bladder urothelial carcinoma (BLCA), sarcoma (SARC), or uterine corpus endometrial carcinoma (UCEC). In some embodiments, the administered composition inhibits tumor growth or metastasis of the GPC2-positive cancer in the subject. In some embodiments, the GPC2-positive cancer includes a metastatic cancer cell, a multiply drug resistant cancer cell, or a recurrent cancer cell. In some embodiments, the administered composition results in increased production of interferon gamma (IFNγ) and/or interleukin-2 (IL-2) in the subject. In some embodiments, the cancer has elevated expression of GPC2. In some embodiments, the cancer having elevated GPC2 expression can be uterine carcinosarcoma (UCS), brain lower grade glioma (LGG), thymoma (THYM), testicular germ cell tumors (TGCT), glioblastoma multiforme (GBM), or skin cutaneous melanoma (SKCM).

The terms "administration" and "administering", as used herein, refer to the delivery of a bioactive composition or formulation by an administration route including, but not limited to, oral, intravenous, intra-arterial, intramuscular, intraperitoneal, subcutaneous, intramuscular, and topical administration, or combinations thereof. The term includes, but is not limited to, administering by a medical professional and self-administering.

Administration of therapeutic agents described herein, e.g., antibodies, CARs, nucleic acids, recombinant cells, cell cultures, and/or pharmaceutical compositions, can be used in the stimulation of an immune response. In some embodiments, antibodies, CARs, nucleic acids, recombinant cells, cell cultures, and/or pharmaceutical compositions as described herein are administered to an individual after induction of remission of cancer with chemotherapy, or after autologous or allogeneic hematopoietic stem cell transplantation. In some embodiments, therapeutic agents described herein are administered to an individual in need of increasing the production of interferon gamma (IFNγ) and/or interleukin-2 (IL-2) in the treated subject relative to the production of these molecules in subjects who have not been administered one of the therapeutic compositions disclosed herein.

An effective amount of the therapeutic agents described herein, e.g., antibodies, CARs, nucleic acids, recombinant cells, cell cultures, and/or pharmaceutical compositions, is determined based on the intended goal, for example tumor regression. For example, where existing cancer is being treated, the amount of a therapeutic agent disclosed herein to be administered may be greater than where administration of the therapeutic agent is for prevention of cancer. One of ordinary skill in the art would be able to determine the amount of a therapeutic agent to be administered and the frequency of administration in view of this disclosure. The quantity to be administered, both according to number of treatments and dose, also depends on the individual to be treated, the state of the individual, and the protection desired. Precise amounts of the therapeutic agent also depend on the judgment of the practitioner and are peculiar to each individual. Frequency of administration could range from 1-2 days, to 2-6 hours, to 6-10 hours, to 1-2 weeks or longer depending on the judgment of the practitioner.

Longer intervals between administration and lower amounts of therapeutic agents may be employed where the goal is prevention. For instance, amounts of therapeutic agents administered per dose may be 50% of the dose administered in treatment of active disease, and administration may be at weekly intervals. One of ordinary skill in the art, in light of this disclosure, would be able to determine an effective amount of therapeutic agents and frequency of administration. This determination would, in part, be dependent on the particular clinical circumstances that are present (e.g., type of cancer, severity of cancer).

In certain embodiments, it may be desirable to provide a continuous supply of the therapeutic agents to the subject to be treated, e.g., a patient. In some embodiments, continuous perfusion of the region of interest (such as the tumor) may be suitable. The time period for perfusion would be selected by the clinician for the particular subject and situation, but times could range from about 1-2 hours, to 2-6 hours, to about 6-10 hours, to about 10-24 hours, to about 1-2 days, to about 1-2 weeks or longer. Generally, the dose of the therapeutic agent via continuous perfusion will be equivalent to that given by single or multiple injections, adjusted for the period of time over which the doses are administered.

In some embodiments, administration is by bolus injection. In some embodiments, administration is by intravenous infusion. In some embodiments, a therapeutic agent is administered in a dosage of about 100 ng/kg of body weight per day to about 100 mg/kg of body weight per day. In some embodiments, a therapeutic agent is administered in a dosage of about 0.001 mg/kg to 100 mg/kg of body weight per day. In some embodiments, the therapeutic agents are administered in a single administration. In some embodiments, therapeutic agents are administered in multiple administrations, (e.g., once or more per week for one or more weeks). In some embodiments, doses are administered about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days. In some embodiments, there are 1, 2, 3, 4, 5, 6, 7, 8, 9, 10, or more total doses. In some embodiments, 4 doses are administered, with a 3 week span between doses.

One of ordinary skill in the art would be familiar with techniques for administering therapeutic agents to an individual. Furthermore, one of ordinary skill in the art would be familiar with techniques and pharmaceutical reagents necessary for preparation of these therapeutic agents prior to administration to an individual.

In certain embodiments of the present disclosure, the therapeutic agents will be an aqueous composition that includes the antibodies, CARs, nucleic acids, recombinant cells, cell cultures, and/or pharmaceutical compositions as described herein. Aqueous compositions of the present disclosure contain an effective amount of a therapeutic agent disclosed herein in a pharmaceutically acceptable carrier or aqueous medium. Thus, the "pharmaceutical preparation" or "pharmaceutical composition" of the disclosure can include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the recombinant cells disclosed herein, its use in the manufacture of the pharmaceutical compositions is contemplated. Supplementary active ingredients can also be incorporated into the compositions. For human administration, preparations should meet sterility, pyrogenicity, general safety, and purity standards as required by the FDA Center for Biologics.

One of ordinary skill in the art would appreciate that biological materials should be extensively dialyzed to remove undesired small molecular weight molecules and/or lyophilized for more ready formulation into a desired vehicle, where appropriate. The therapeutic agents described herein, e.g., antibodies, CARs, nucleic acids, recombinant cells, cell cultures, and/or pharmaceutical compositions, will then generally be formulated for administration by any known route, such as parenteral administration. Determination of the amount of therapeutic agents to be administered will be made by one of skill in the art, and will in part be dependent on the extent and severity of cancer, and whether the recombinant cells are being administered for treatment of existing cancer or prevention of cancer. The preparation of the therapeutic agents containing the antibodies, CARs, nucleic acids, recombinant cells, cell cultures, and/or pharmaceutical compositions of the disclosure will be known to those of skill in the art in light of the present disclosure.

Upon formulation, therapeutic agents will be administered in a manner compatible with the dosage formulation and in such amount as is therapeutically effective. The therapeutic agents can be administered in a variety of dosage forms, such as the type of injectable solutions described above. For parenteral administration, the therapeutic agents disclosed herein should be suitably buffered. As discussed in greater detail below, the therapeutic agents as described herein may be administered with other therapeutic agents that are part of the therapeutic regiment of the individual, such as other immunotherapy or chemotherapy.

The antibodies, CARs, nucleic acids, recombinant cells, cell cultures, and/or pharmaceutical compositions described herein can be used to cure established tumors, inhibit tumor growth or metastasis of the GPC2-positive cancer in the treated subject relative to the tumor growth or metastasis in subjects who have not been administered one of the therapeutic compositions disclosed herein. In some embodiments, the antibodies, CARs, nucleic acids, recombinant cells, cell cultures, and/or pharmaceutical compositions described herein can be used to stimulate immune responses against the tumor via inducing the production of interferon gamma (IFN$\gamma$) and/or interleukin-2 (IL-2) and other pro-inflammatory cytokines. In some embodiments, the antibodies, CARs, nucleic acids, recombinant cells, cell cultures, and/or pharmaceutical compositions described herein can be used to stimulate proliferation and/or killing capacity of CAR T-cells in the treated subject relative to the production of these molecules in subjects who have not been administered one of the therapeutic compositions disclosed herein. The production of interferon gamma (IFN$\gamma$) and/or interleukin-2 (IL-2) can be stimulated to produce up to about 20 fold, such as any of about 2 fold, 3 fold, 4 fold, 5 fold, 6 fold, 7 fold, 8 fold, 9 fold, 10 fold, 11 fold, 12 fold, 13 fold, 14 fold, 15 fold 16 fold, 17 fold, 18 fold, 19 fold, or 20 fold or higher compared to the production of interferon gamma (IFN$\gamma$) and/or interleukin-2 (IL-2) in subjects who have not been administered one of the therapeutic compositions disclosed herein.

Administration of Recombinant Cells to a Subject

In some embodiments, the methods of the disclosure involve administering an effective amount or number of the recombinant cells provided herein to a subject in need thereof. This administering step can be accomplished using any method of implantation delivery in the art. For example, the recombinant cells can be infused directly in the subject's bloodstream or otherwise administered to the subject.

In some embodiments, the methods disclosed herein include administering, which term is used interchangeably with the terms "introducing," implanting," and "transplanting," recombinant cells into an individual, by a method or route that results in at least partial localization of the introduced cells at a desired site such that a desired effect(s) is/are produced. The recombinant cells or their differentiated progeny can be administered by any appropriate route that results in delivery to a desired location in the individual where at least a portion of the administered cells or components of the cells remain viable. The period of viability of the cells after administration to a subject can be as short as a few hours, e.g., twenty-four hours, to a few days, to as long as several years, or even the lifetime of the individual, i.e., long-term engraftment.

When provided prophylactically, the recombinant cells described herein can be administered to a subject in advance of any symptom of a disease or condition to be treated. Accordingly, in some embodiments the prophylactic administration of a recombinant cell population prevents the occurrence of symptoms of the disease or condition.

When provided therapeutically in some embodiments, recombinant cells are provided at (or after) the onset of a symptom or indication of a disease or condition, e.g., upon the onset of disease or condition.

For use in the various embodiments described herein, an effective amount of recombinant cells as disclosed herein, can be at least $10^2$ cells, at least $5\times10^2$ cells, at least $10^3$ cells, at least $5\times10^3$ cells, at least 10+ cells, at least $5\times10^4$ cells, at least $10^5$ cells, at least $2\times10^5$ cells, at least $3\times 10^5$ cells, at least $4\times10^5$cells, at least $5\times10^5$cells, at least $6\times10^5$cells, at least $7\times10^5$cells, at least $8\times10^5$cells, at least $9\times10^5$cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof. The recombinant cells can be derived from one or more donors or can be obtained from an autologous source. In some embodiments, the recombinant cells are expanded in culture prior to administration to a subject in need thereof.

In some embodiments, the delivery of a recombinant cell composition (e.g., a composition including a plurality of recombinant cells according to any of the cells described herein) into a subject by a method or route results in at least partial localization of the cell composition at a desired site. A composition including recombinant cells can be administered by any appropriate route that results in effective treatment in the subject, e.g., administration results in delivery to a desired location in the subject where at least a portion of the composition delivered, e.g., at least $1\times10^4$ cells, is delivered to the desired site for a period of time. Modes of administration include injection, infusion, and instillation. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. In some embodiments, the route is intravenous. For the delivery of cells, delivery by injection or infusion is a standard mode of administration.

In some embodiments, the recombinant cells are administered systemically, e.g., via infusion or injection. For example, a population of recombinant cells are administered other than directly into a target site, tissue, or organ, such that it enters, the subject's circulatory system and, thus, is subject to metabolism and other similar biological processes.

The efficacy of a treatment including any of the compositions provided herein for the treatment of a disease or condition can be determined by a skilled clinician. However, one skilled in the art will appreciate that a treatment is considered effective if any one or all of the signs or symptoms or markers of disease are improved or ameliorated. Efficacy can also be measured by failure of a subject to worsen as assessed by decreased hospitalization or need for medical interventions (e.g., progression of the disease is halted or at least slowed). Methods of measuring these indicators are known to those of skill in the art and/or described herein. Treatment includes any treatment of a disease in a subject or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

Measurement of the degree of efficacy is based on parameters selected with regard to the disease being treated and the symptoms experienced. In general, a parameter is selected that is known or accepted as correlating with the degree or severity of the disease, such as a parameter accepted or used in the medical community. For example, in the treatment of a solid cancer, suitable parameters can include reduction in the number and/or size of metastases, number of months of progression-free survival, overall survival, stage or grade of the disease, the rate of disease progression, the reduction in diagnostic biomarkers (for example without limitation, a reduction in circulating tumor DNA or RNA, a reduction in circulating cell-free tumor DNA or RNA, and the like), and combinations thereof. It will be understood that the effective dose and the degree of efficacy will generally be determined with relation to a single subject and/or a group or population of subjects. Therapeutic methods of the disclosure reduce symptoms and/or disease severity and/or disease biomarkers by at least about 1, 2, 3, 4, 5, 10, 15, 20, 25, 30, 35, 40, 45, 50, 55, 60, 65, 70, 75, 80, 85, 90, 95, 96, 97, 98, 99, or 100%.

As discussed above, a therapeutically effective amount includes an amount of a therapeutic composition that is sufficient to promote a particular beneficial effect when administered to a subject, such as one who has, is suspected of having, or is at risk for a disease. In some embodiments, an effective amount includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

Additional Therapies

As discussed supra, any one of the antibodies, CARs, nucleic acids, recombinant cells, cell cultures, and/or pharmaceutical compositions described herein can be administered to a subject in need thereof as a single therapy (e.g., monotherapy). In addition or alternatively, in some embodiments of the disclosure, the antibodies, CARs, nucleic acids, recombinant cells, cell cultures, and/or pharmaceutical compositions described herein can be administered to a subject in combination with one or more additional therapeutic agents, e.g., at least one, two, three, four, or five additional therapies. Suitable therapies to be administered in combination with the compositions of the disclosure include, but are not limited to chemotherapy, radiotherapy, immunotherapy, hormonal therapy, toxin therapy, targeted therapy, and surgery. Other suitable therapies include chemotherapeutics, anti-cancer agents, and anti-cancer therapies.

Administration "in combination with" one or more additional therapeutic includes simultaneous (concurrent) and consecutive administration in any order. In some embodiments, the one or more additional therapies is selected from the group consisting of chemotherapy, radiotherapy, immunotherapy, hormonal therapy, toxin therapy, and surgery. The term chemotherapy as used herein encompasses anti-cancer agents. Various classes of anti-cancer agents can be suitably used for the methods disclosed herein. Non-limiting examples of anti-cancer agents include: alkylating agents, antimetabolites, anthracyclines, plant alkaloids, topoisomerase inhibitors, podophyllotoxin, antibodies (e.g., monoclonal or polyclonal), checkpoint inhibitors, immunomodulators, cytokines, nanoparticles, radiation therapy, tyrosine kinase inhibitors (e.g., imatinib mesylate (Gleevec® or Glivec®)), hormone treatments, soluble receptors and other antineoplastics.

Topoisomerase inhibitors are also another class of anti-cancer agents that can be used herein. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecin such as irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Antineoplastics include the immunosuppressant dactinomycin, doxorubicin, epirubicin, bleomycin, mechlorethamine, cyclophosphamide, chlorambucil, ifosfamide. The antineoplastic compounds generally work by chemically modifying a cell's DNA.

Alkylating agents can alkylate many nucleophilic functional groups under conditions present in cells. Cisplatin and carboplatin, and oxaliplatin are alkylating agents. They impair cell function by forming covalent bonds with the amino, carboxyl, sulfhydryl, and phosphate groups in biologically important molecules.

Vinca alkaloids bind to specific sites on tubulin, inhibiting the assembly of tubulin into microtubules (M phase of the cell cycle). The vinca alkaloids include: vincristine, vinblastine, vinorelbine, and vindesine.

Anti-metabolites resemble purines (azathioprine, mercaptopurine) or pyrimidine and prevent these substances from becoming incorporated in to DNA during the "S" phase of the cell cycle, stopping normal development and division. Anti-metabolites also affect RNA synthesis.

Plant alkaloids and terpenoids are obtained from plants and block cell division by preventing microtubule function. Since microtubules are vital for cell division, without them, cell division cannot occur. The main examples are *vinca* alkaloids and taxanes.

Podophyllotoxin is a plant-derived compound which has been reported to help with digestion as well as used to produce two other cytostatic drugs, etoposide and teniposide. They prevent the cell from entering the G1 phase (the start of DNA replication) and the replication of DNA (the S phase).

Taxanes as a group includes paclitaxel and docetaxel. Paclitaxel is a natural product, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

In some embodiments, the anti-cancer agents can be selected from remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, gefitinib (Iressa®), taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib (Velcade®), bisphosphonate, arsenic trioxide, vincristine, doxorubicin (Doxil®), paclitaxel, ganciclovir, adriamycin, estrainustine sodium phosphate (Emcyt®), sulindac, etoposide, and combinations of any thereof.

In other embodiments, the anti-cancer agent can be selected from bortezomib, cyclophosphamide, dexamethasone, doxorubicin, interferon-alpha, lenalidomide, melphalan, pegylated interferon-alpha, prednisone, thalidomide, or vincristine.

In some embodiments, the methods of prevention and/or treatment as described herein further include administration of a compound that inhibits one or more immune checkpoint molecules. In some embodiments, the one or more immune checkpoint molecules include one or more of CTLA4, PD-1, PD-L1, A2AR, B7-H3, B7-H4, TIM3, and combinations of any thereof. In some embodiments, the compound that inhibits the one or more immune checkpoint molecules includes an antagonistic antibody. In some embodiments, the antagonistic antibody is ipilimumab, nivolumab, pembrolizumab, durvalumab, atezolizumab, tremelimumab, or avelumab.

In some aspects, the one or more anti-cancer therapy is radiation therapy. In some embodiments, the radiation therapy can include the administration of radiation to kill cancerous cells. Radiation interacts with molecules in the cell such as DNA to induce cell death. Radiation can also damage the cellular and nuclear membranes and other organelles. Depending on the radiation type, the mechanism of DNA damage may vary as does the relative biologic effectiveness. For example, heavy particles (i.e. protons, neutrons) damage DNA directly and have a greater relative biologic effectiveness. Electromagnetic radiation results in indirect ionization acting through short-lived, hydroxyl free radicals produced primarily by the ionization of cellular water. Clinical applications of radiation consist of external beam radiation (from an outside source) and brachytherapy (using a source of radiation implanted or inserted into the patient). External beam radiation consists of X-rays and/or gamma rays, while brachytherapy employs radioactive nuclei that decay and emit alpha particles, or beta particles along with a gamma ray. Radiation also contemplated herein includes, for example, the directed delivery of radioisotopes to cancer cells. Other forms of DNA damaging factors are also contemplated herein such as microwaves and UV irradiation.

Radiation may be given in a single dose or in a series of small doses in a dose-fractionated schedule. The amount of radiation contemplated herein ranges from about 1 to about 100 Gy, including, for example, about 5 to about 80, about 10 to about 50 Gy, or about 10 Gy. The total dose may be applied in a fractioned regime. For example, the regime may include fractionated individual doses of 2 Gy. Dosage ranges for radioisotopes vary widely, and depends on the half-life of the isotope and the strength and type of radiation emitted. When the radiation includes use of radioactive isotopes, the isotope may be conjugated to a targeting agent, such as a therapeutic antibody, which carries the radionucleotide to the target tissue (e.g., tumor tissue).

Surgery described herein includes resection in which all or part of a cancerous tissue is physically removed, exercised, and/or destroyed. Tumor resection refers to physical removal of at least part of a tumor. In addition to tumor resection, treatment by surgery includes laser surgery, cryosurgery, electrosurgery, and microscopically controlled surgery (Mohs surgery). Removal of precancers or normal tissues is also contemplated herein. Accordingly, in some embodiments, the methods of the disclosure include administration of a composition disclosed herein to a subject individually as a single therapy (e.g., monotherapy). In some embodiments, a composition of the disclosure is administered to a subject as a first therapy in combination with a second therapy, such as an anti-cancer agent, a chemotherapeutic, or an anti-cancer therapy. In some embodiments, the second therapy is selected from the group consisting of chemotherapy, radiotherapy, immunotherapy, hormonal therapy, toxin therapy, and surgery. In some embodiments, the first therapy and the second therapy are administered concomitantly. In some embodiments, the first therapy and the second therapy are administered sequentially. In some embodiments, the first therapy is administered before the second therapy. In some embodiments, the first therapy is administered before and/or after the second therapy. In some embodiments, the first therapy and the second therapy are administered in rotation. In some embodiments, the first therapy is administered at the same time as the second therapy. In some embodiments, the first therapy and the second therapy are administered together in a single formulation.

Further provided herein are methods of detecting expression of GPC2 in a sample. In some embodiments, the method includes contacting the sample with an antibody disclosed herein; and detecting binding of the antibody to the sample, thereby detecting expression of GPC2 in the sample. In some embodiments, the antibody is directly labeled. In some embodiments, the method further includes contacting the antibody of the disclosure with a second antibody, and detecting the binding of the second antibody to the antibody of the disclosure. In some embodiments, the sample is obtained from a subject suspected of having a GPC2-positive cancer. In some examples, the sample is a tumor biopsy.

Kits

Also provided herein are various kits for the practice of a method described herein. In particular, some embodiments of the disclosure provide kits for the diagnosis of a condition in a subject. Some other embodiments relate to kits for the prevention of a condition in a subject in need thereof. Some other embodiments relate to kits for methods of treating a condition in a subject in need thereof. For example, provided herein, in some embodiments, are kits that include one or more of the CARs, recombinant nucleic acids, recombinant cells, antibodies, or pharmaceutical compositions as provided and described herein, as well as written instructions for making and using the same.

In some embodiments, the kits of the disclosure further include one or more means useful for the administration of any one of the provided CARs, recombinant nucleic acids, recombinant cells, or pharmaceutical compositions to an individual. For example, in some embodiments, the kits of the disclosure further include one or more syringes (including pre-filled syringes) and/or catheters (including pre-filled syringes) used to administer any one of the provided CARs, recombinant nucleic acids, recombinant cells, or pharmaceutical compositions to an individual. In some embodiments, a kit can have one or more additional therapeutic agents that can be administered simultaneously or sequentially with the other kit components for a desired purpose, e.g., for diagnosing, preventing, or treating a condition in a subject in need thereof.

Any of the above-described kits can further include one or more additional reagents, where such additional reagents can be selected from: dilution buffers; reconstitution solutions, wash buffers, control reagents, control expression vectors, negative control polypeptides, positive control polypeptides, reagents suitable for in vitro production of the CARs.

In some embodiments, the components of a kit can be in separate containers. In some other embodiments, the components of a kit can be combined in a single container. In some embodiments, a kit can further include instructions for using the components of the kit to practice the methods disclosed herein. The instructions for practicing the methods are generally recorded on a suitable recording medium. For example, the instructions can be printed on a substrate, such as paper or plastic, etc. The instructions can be present in the kit as a package insert, in the labeling of the container of the kit or components thereof (e.g., associated with the packaging or sub-packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), can be provided. An example of this embodiment is a kit that includes a web address where the instructions can be viewed and/or from which the instructions can be downloaded. As with the instructions, this means for obtaining the instructions can be recorded on a suitable substrate.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

Additional embodiments are disclosed in further detail in the following examples, which are provided by way of illustration and are not in any way intended to limit the scope of this disclosure or the claims.

Example 1

Binder Selection and Modification of Spacer Domain

This Example describes experiments performed to identify new antibodies, such as single chain variable fragments (scFv) capable of binding a recombinant GPC2, and the prioritization of GPC2-targeting scFvs for utilization in CAR T-cell constructs. It has been recognized that utilizing single chain variable fragment (scFv) sequences as GPC2-specific binding moiety of CAR constructs often requires extensive optimization of constructs for optimal efficacy. Antigen-independent clustering of scFv domains can induce tonic signaling and decrease functionality of CAR constructs. Without being bound to any particular theory, it is also believed that CAR T-cell functionality is often associated with the suitable distance between the T-cell and the targeted epitope on the tumor cell, which can be achieved by including a spacer domain and choosing suitable hinge/transmembrane and signaling domains are important for efficacy.

With the aim to develop GPC2-targeted CAR T-cell constructs, several experiments were performed to identify anti-GPC2 binding sequences utilizing a human naïve Fab phage library for panning against recombinant human GPC2. Two newly identified binders GPC2.19 and GPC2.27 were converted into single-chain variable fragments (scFvs). Utilizing single chain variable fragment (scFv) sequences as target-specific binding moiety of chimeric antigen receptor constructs requires extensive optimization of constructs for optimal efficacy. Antigen-independent clustering of scFv domains can induce tonic signaling and decrease functionality of CAR constructs. CAR T-cell functionality is associated with the optimal distance between the T-cell and the targeted epitope on the tumor cell, which can be achieved by including a spacer domain and choosing the optimal hinge/transmembrane and signaling domains are crucial for optimal efficacy.

Figure 2B:
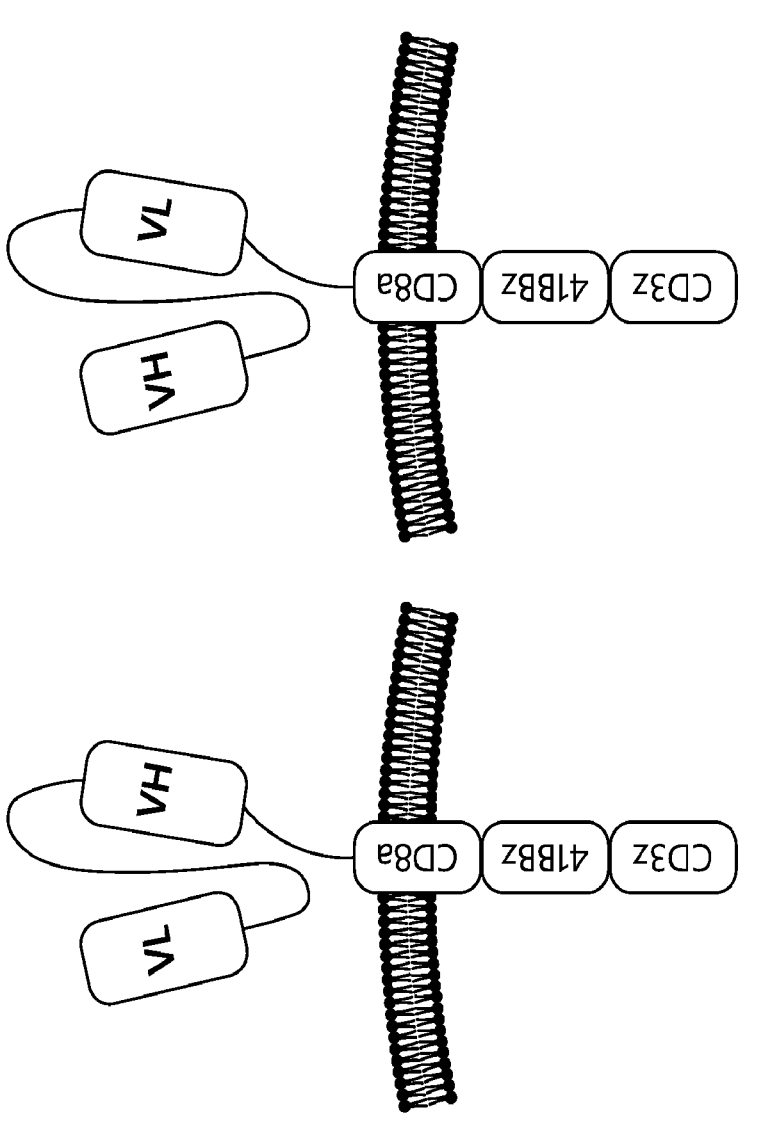
Figure 2C:
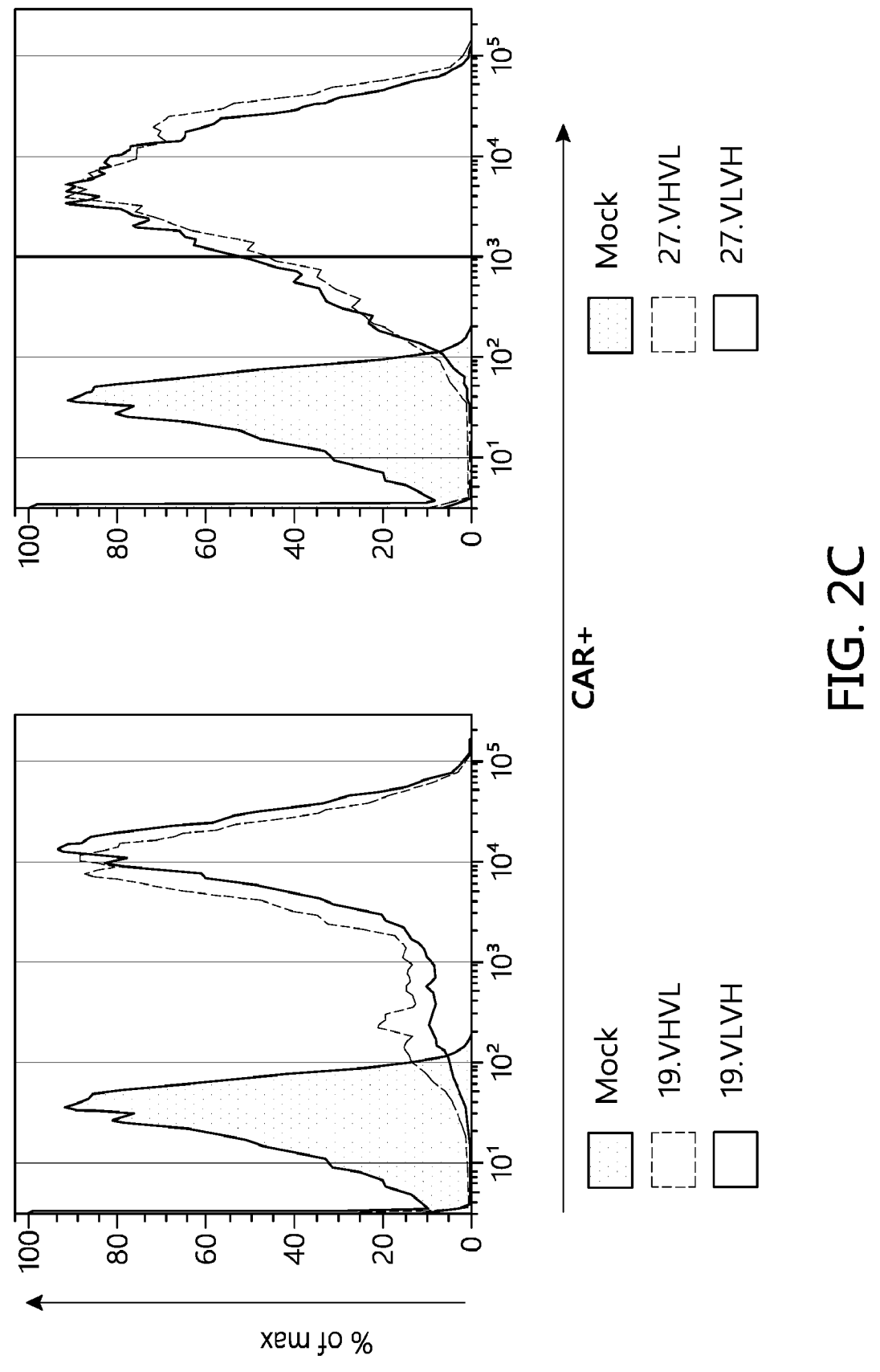
Figure 2:
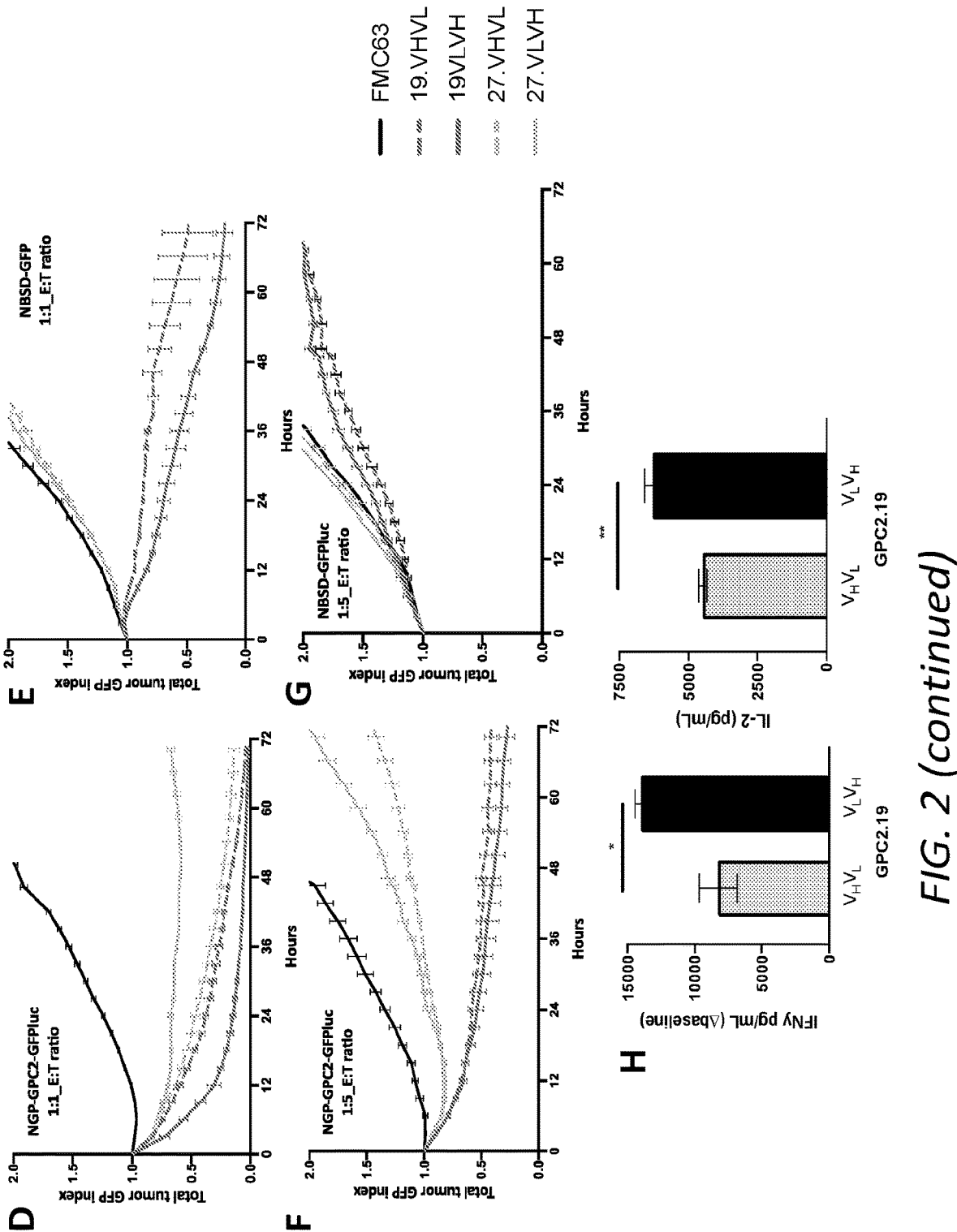

All scFv sequences (FIG. 2A) were expressed in a second-generation CAR-T retroviral vector, possessing a CD8a hinge and transmembrane domain and a 41BBz signaling domain, in two orientations with either N-terminal variable heavy chain or N-terminal variable light chain (FIG. 2B). CARs incorporating all 4 constructs were found to express on the cell surface of primary, activated T-cells and bound soluble, recombinant GPC2 (FIG. 2C).

To identify the most promising construct for clinical CAR development, CAR-T cells were co-cultured against tumor cells with native GPC2 expression (GPC2$^N$: NBSD) or an isogenic cell line engineered to express GPC2 at supra-physiological levels (GPC2$^{Hi}$: NGP-GPC2) and assessed for in vitro functionality assessed by cytokine production and killing capacity.

While all constructs showed potent killing against GPC2$^{Hi}$ (FIG. 2D) only GPC2.19 based constructs showed efficacy against GPC2$^N$ at 1:1 effector to target ratios (FIG. 2E) and residual killing capacity when challenged with 5× excess of GPC2$^{Hi}$ tumor cells (FIG. 2F), but failed against the same amount of GPC2$^N$ tumor cells (FIG. 2G). GPC2.19 based constructs were further assessed for cytokine production post co-culture with GPC2$^{Hi}$ tumor cells and displayed superior secretion of IFNγ and IL-2 in the VL/VH orientation (FIG. 2H).

Example 2

Antigen Density Drives GPC2-Targeting CAR T-Cell Efficacy

This Example summarizes the results of experiments performed to illustrate that GPC2-targeting CAR T-cell efficacy is limited by target site density.

Figure 3:
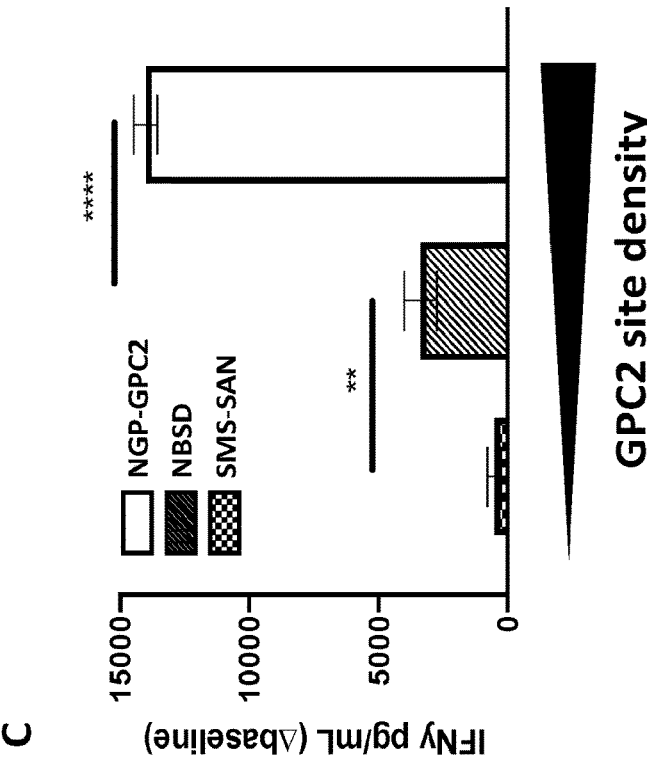
FIGS. 3A-3K schematically summarize the results of experiments illustrating that GPC2 CAR T-cell efficacy is limited by target site density.
Figure 3:
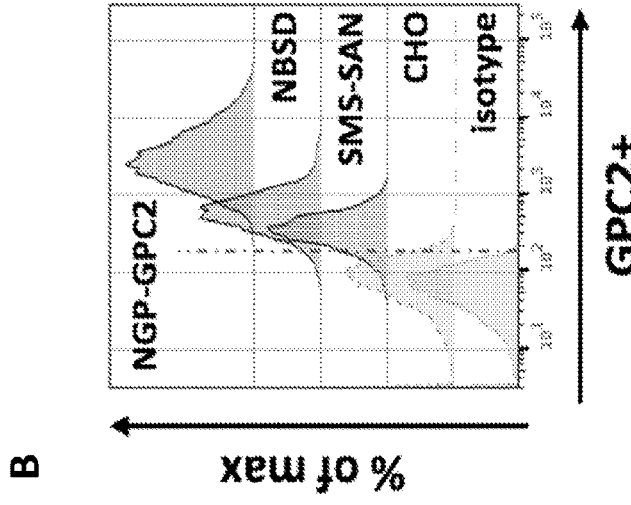
Figure 3:
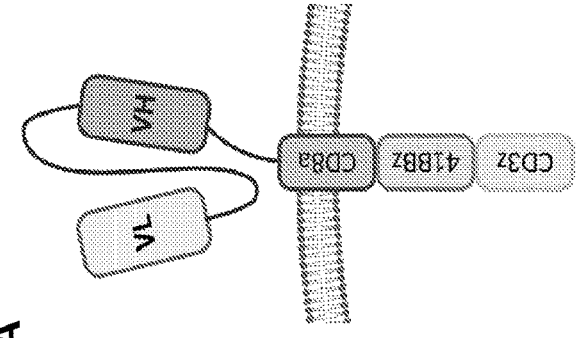
Figure 3:
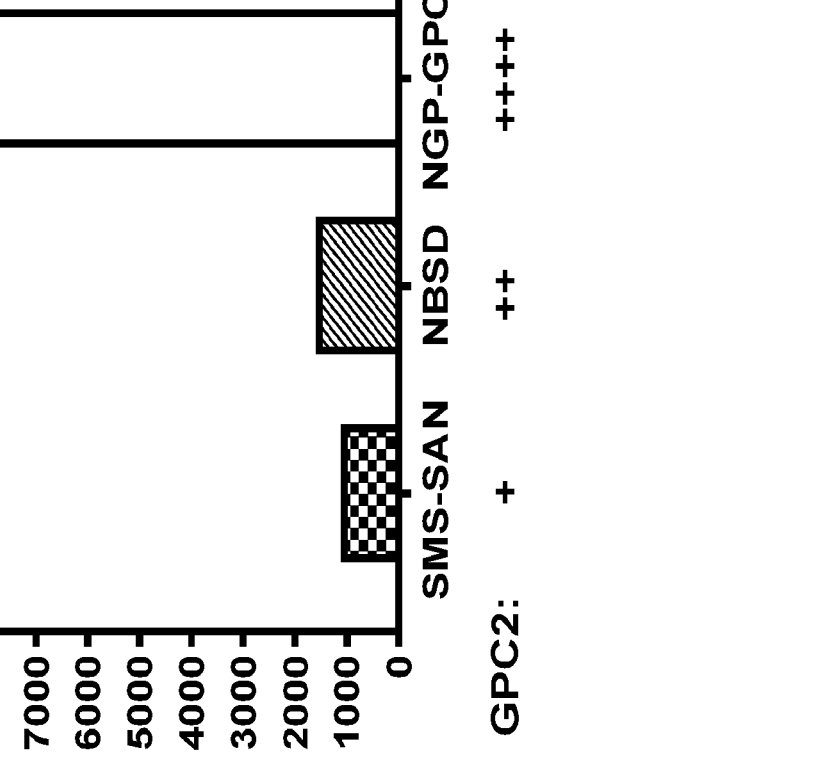
Figure 3E:
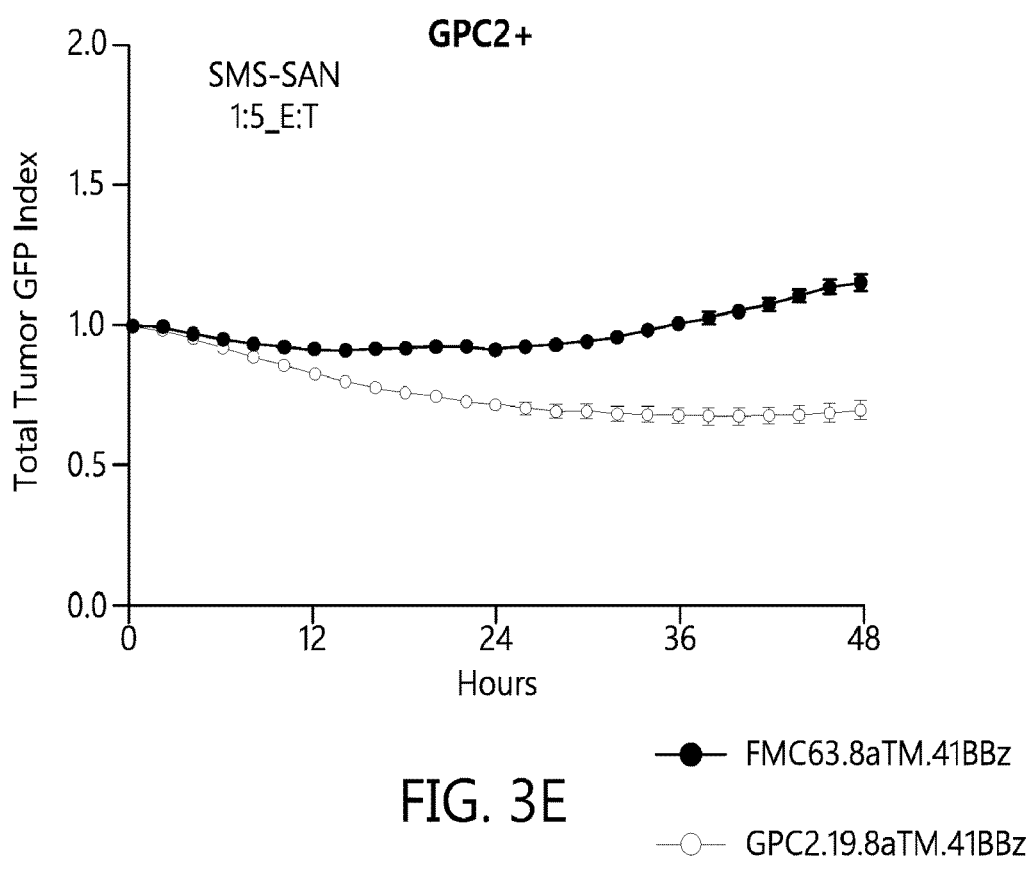
Figure 3F:
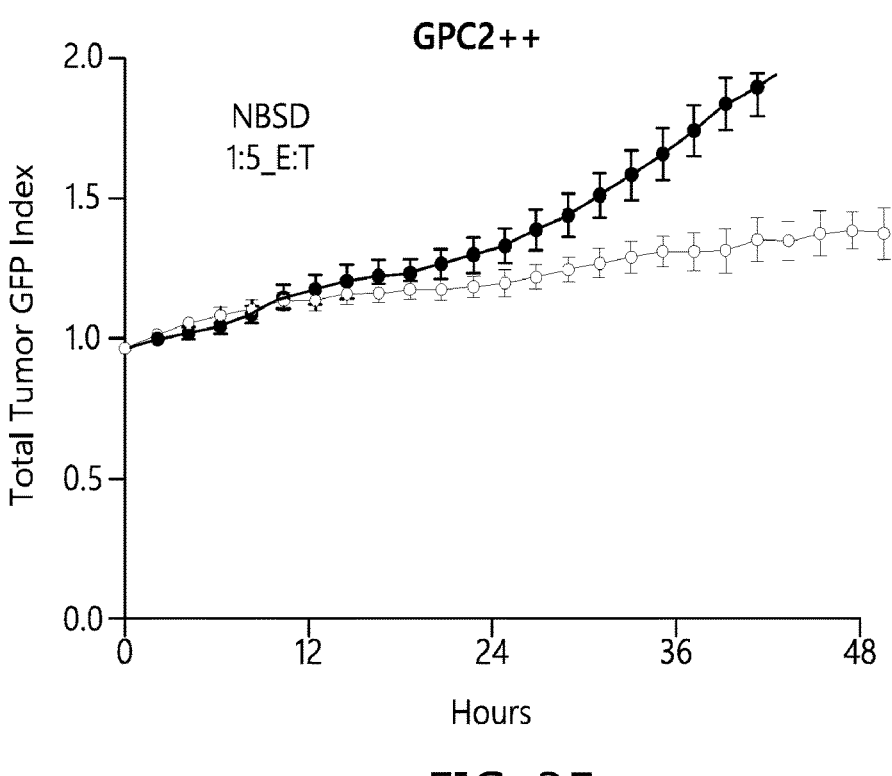
Figure 3G:
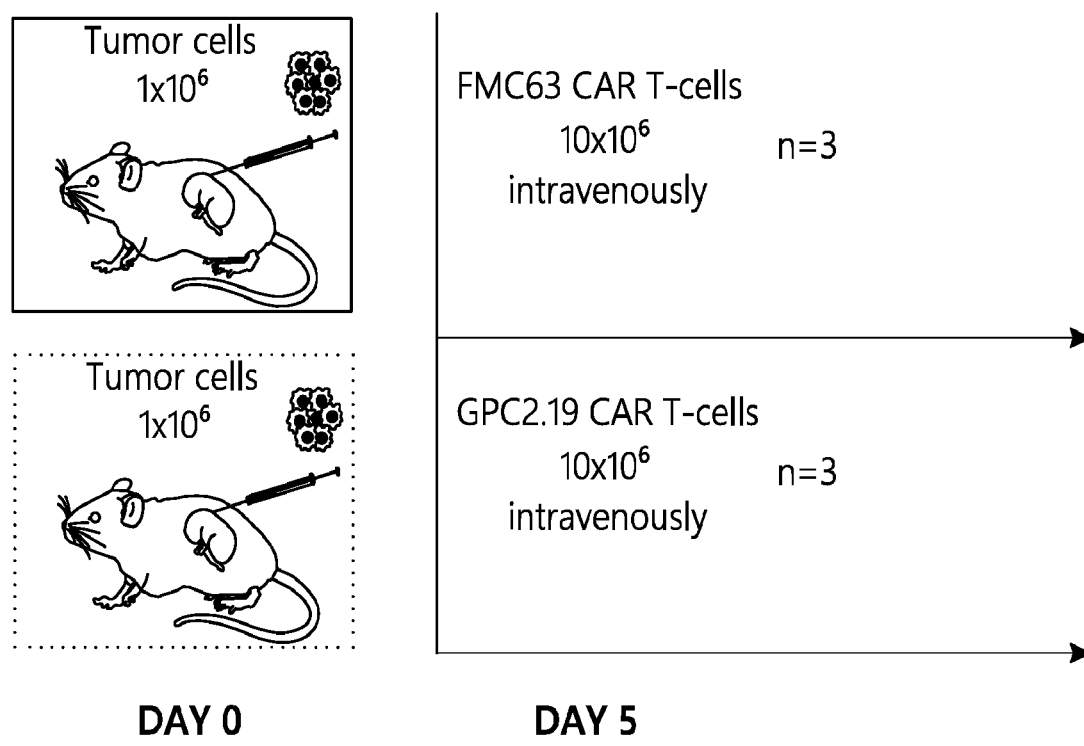
Figure 3H:
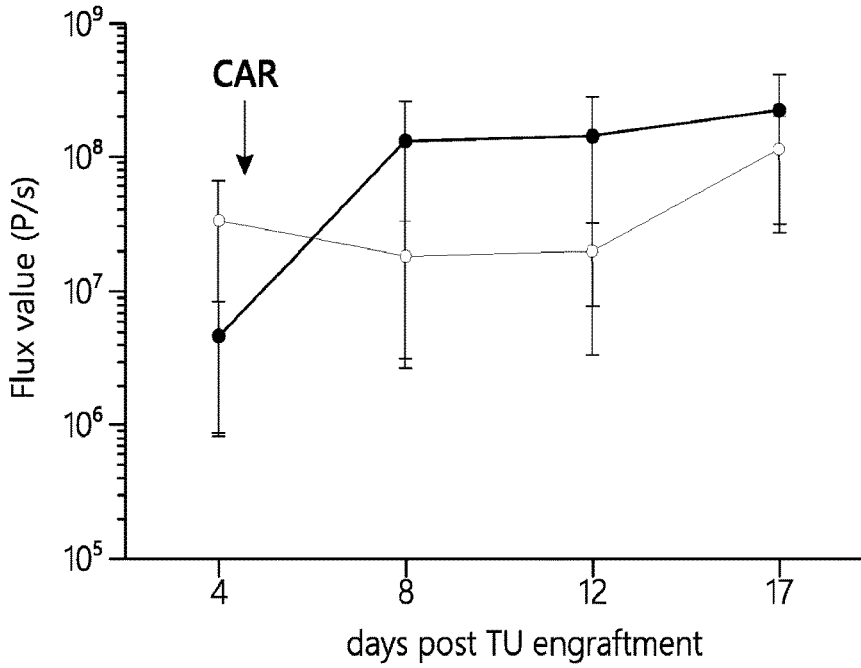
Figure 3I:
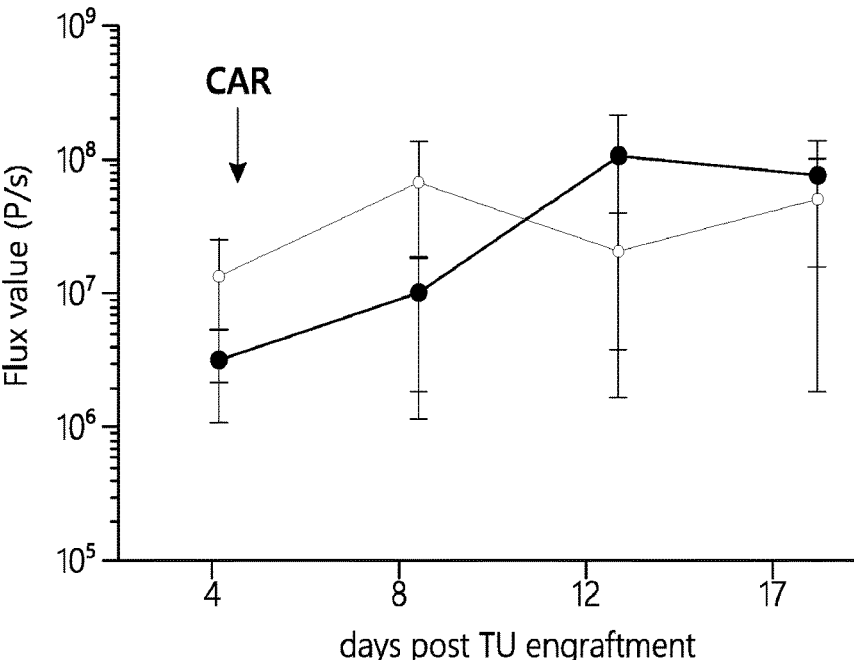
Figure 3J:
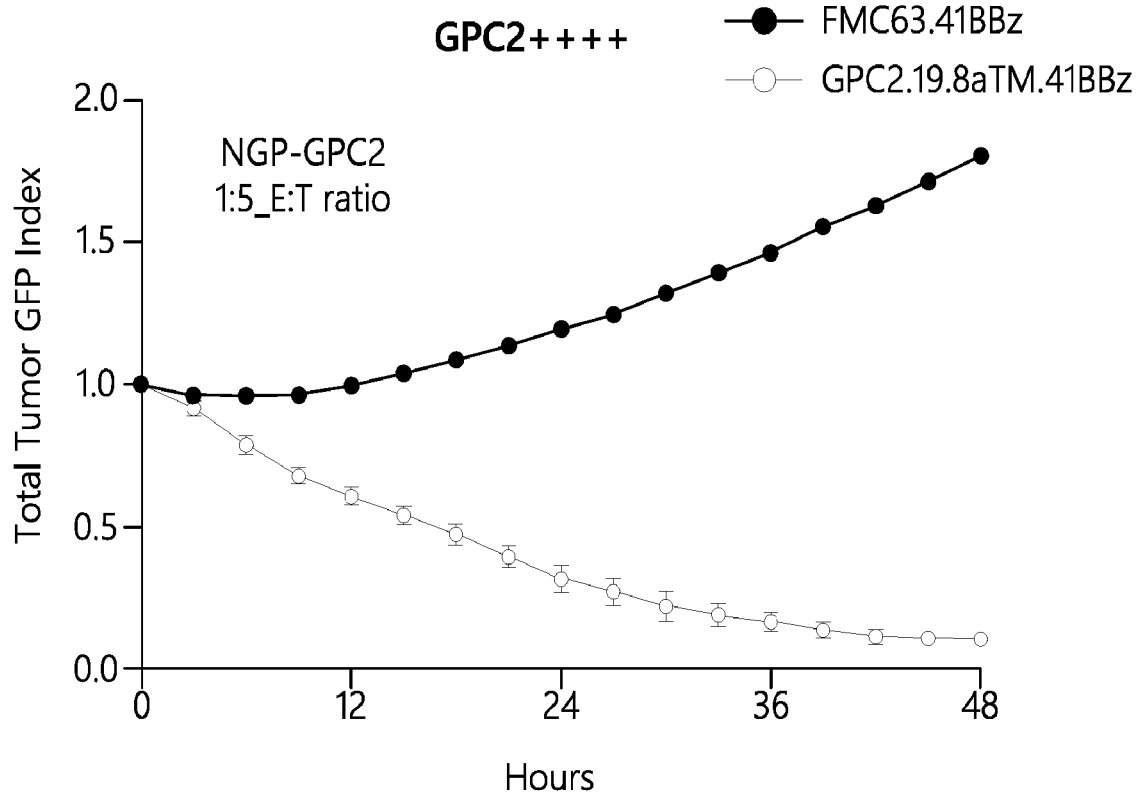
Figure 3K:
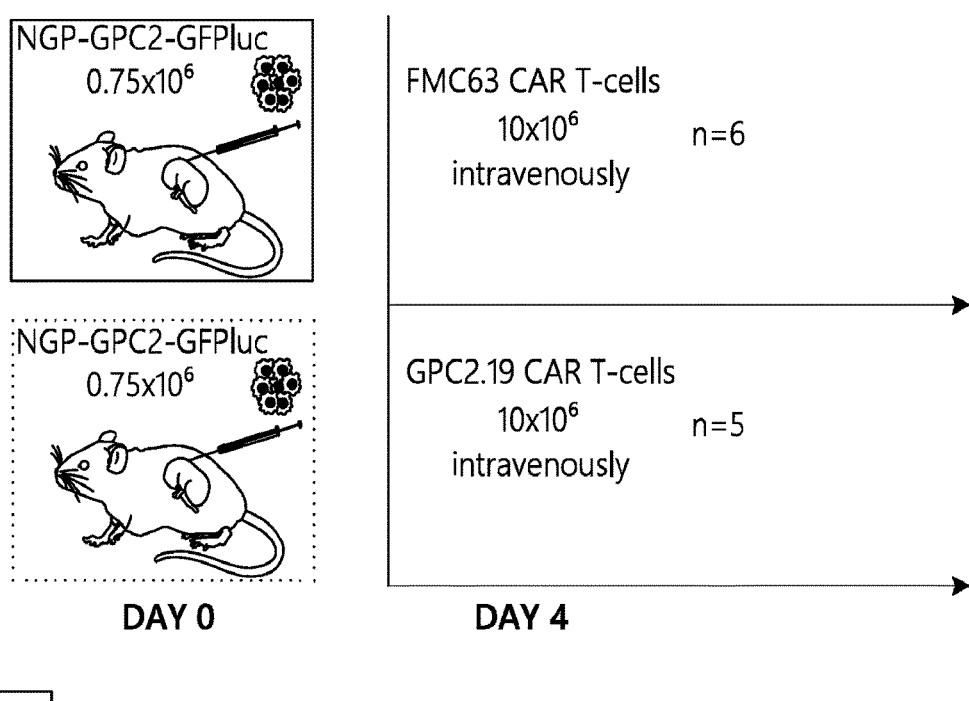
Figure 3K:
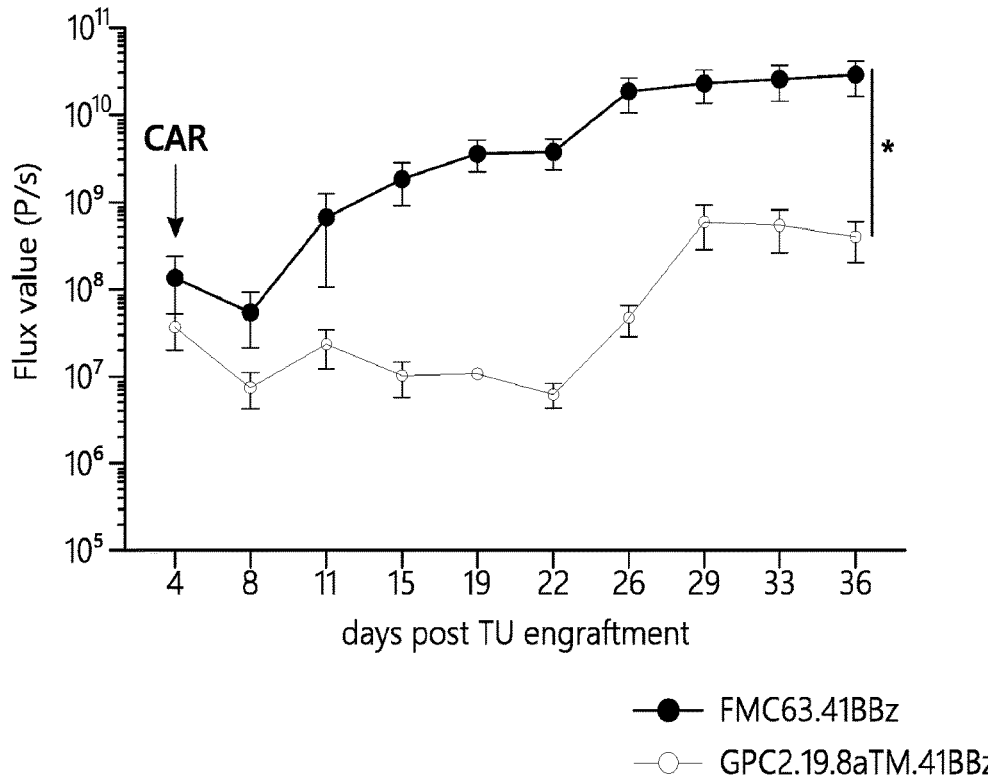

Based on in vitro efficacy, the GPC2.19 CAR T-cells in the VL/VH orientation were prioritized as the lead candidate construct (FIG. 3A). Overall, it was observed that GPC2.19 CAR T-cells followed a trend in which antigen density on target cells (FIG. 3B) is a determining factor for better CAR functionality, as GPC2.19 CAR T-cells secrete IFNγ in an antigen density-dependent manner (FIG. 3C), with low levels induced by native GPC2 expressing cell lines SMS-SAN (1116 molecules/cell), slightly increased levels induced by NBSD (1601 molecules/cell) and high levels in response to isogenic tumor cells NGP-GPC2 (9851 molecules/cell) expressing the antigen at supraphysiolocial levels (FIG. 3D). This is raising concerns that the moderate site density predicted to be present on human tumors would be insufficient for effective CAR activity. In fact, GPC2.19 CAR T-cells fail to kill native GPC2 site density tumor cell lines SMS-SAN (GPC2+) and NBSD (GPC2++) when challenged with 5× excess of tumor cells per CAR positive T-cell (FIGS. 3E-3F) and fail to induce anti-tumor effects in vivo against GPC2\ neuroblastoma xenograft models, when SMS-SAN (FIG. 3H) or NBSD (FIG. 3I) tumor cells were engrafted in an orthotopic manner into the subrenal capsule in comparison to CD19-targeted (FMC63) control CAR T-cells. Contrary, GPC2 CAR T-cells were still able to kill GPC2$^{Hi}$ cells in vitro, even when challenged with a 5× excess of tumor cells (FIG. 3J) and significant in vivo anti-tumor effects could be achieved when engrafting GPC21 expressing tumors, recapitulating in vitro findings (FIG. 3K) yet, lacking complete tumor control. In conclusion, these results indicate that GPC2 CAR T-cell constructs in this architecture, do not meet the activation threshold required to effectively target native levels of GPC2 expressed on neuroblastoma tumor cells and are not expected to result in striking clinical outcomes.

Example 3

Integration of an Extracellular Spacer Domain does not Improve CAR Functionality This Example describes experiments performed to illustrate that integration of an extracellular spacer domain does not improve CAR functionality.

Figure 4A:
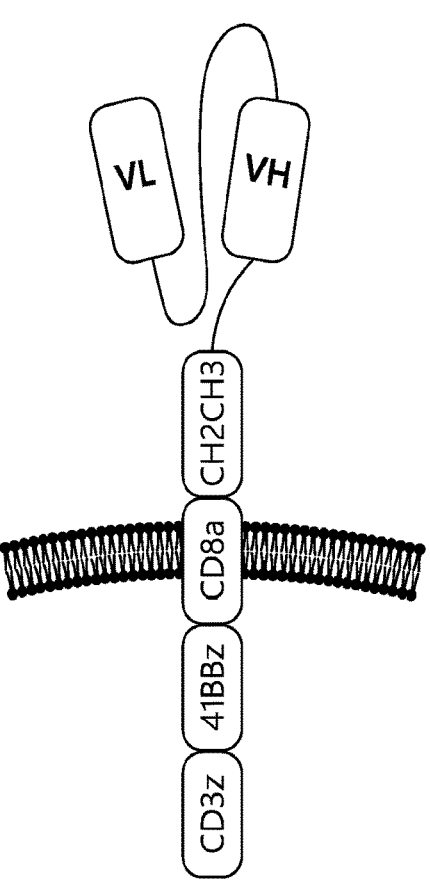
FIGS. 4A-4E schematically summarize the results of experiments performed to illustrate that integration of an extracellular spacer domains does not improve CAR functionality.
Figure 4B:
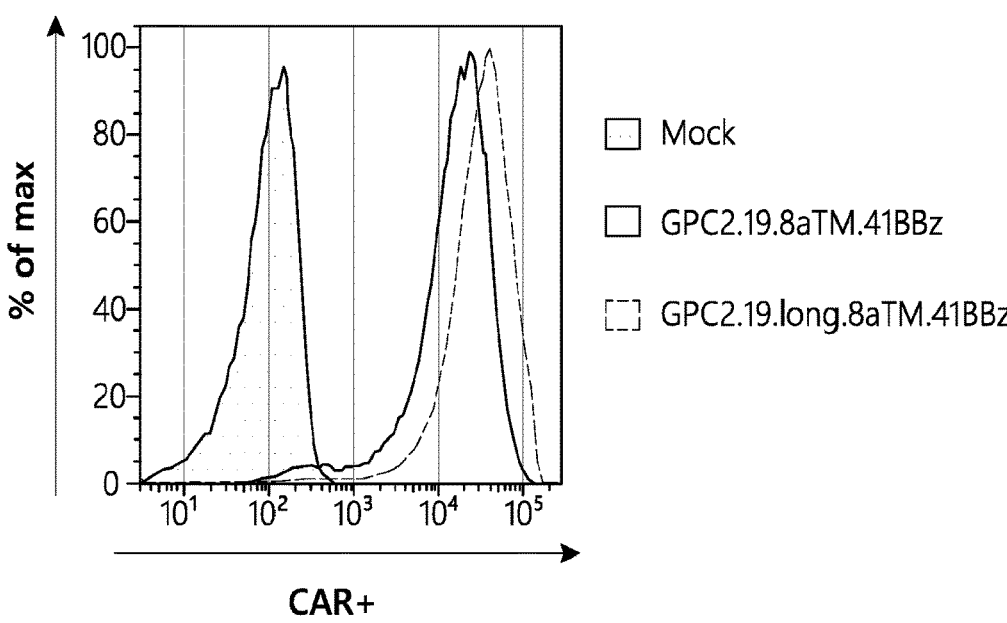
Figure 4:
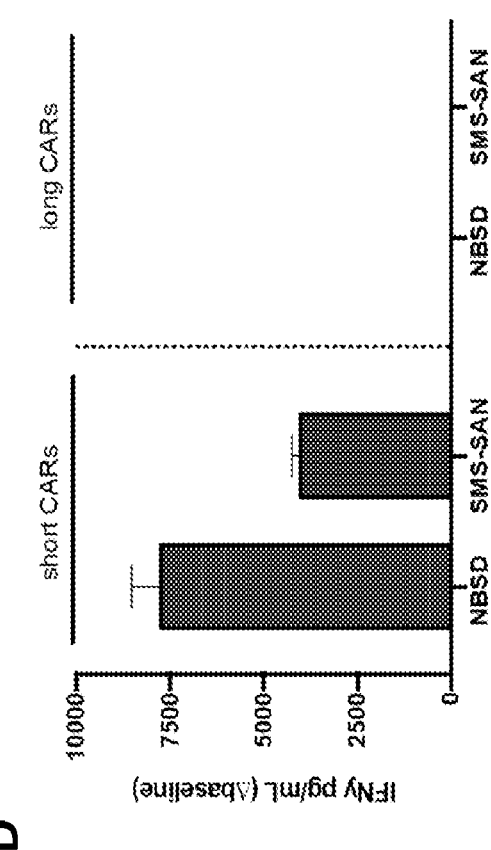
Figure 4:
Figure 4:
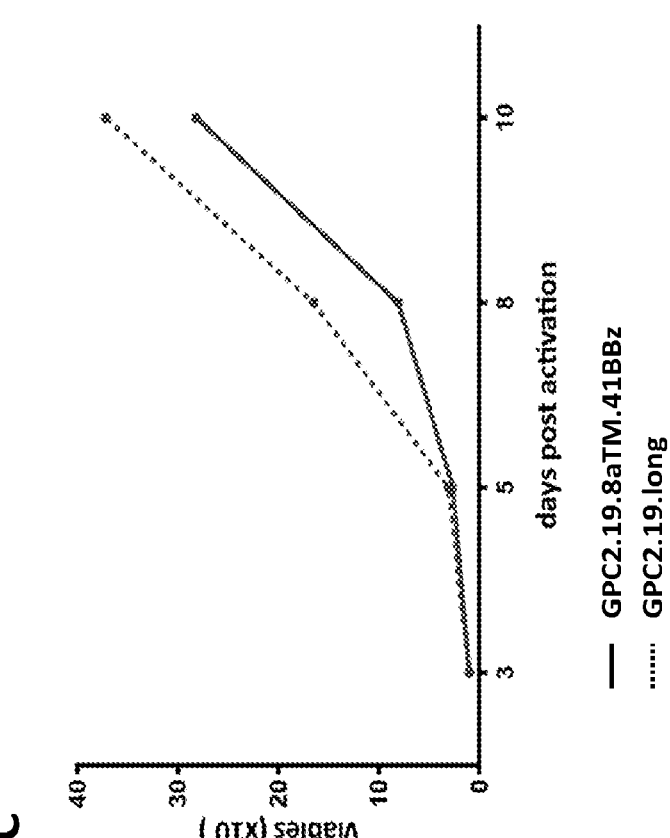
Figure 4E:
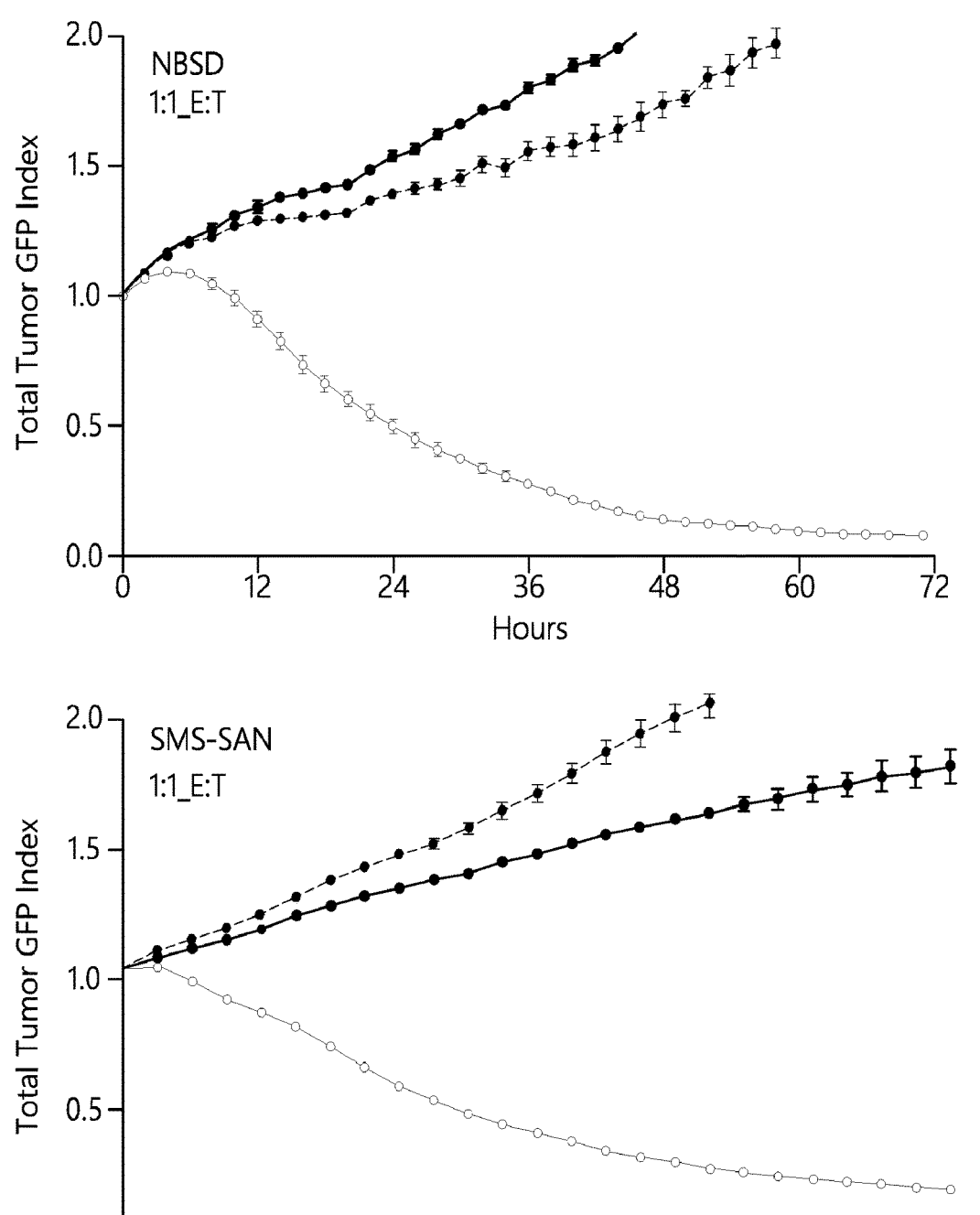
Figure 4E:
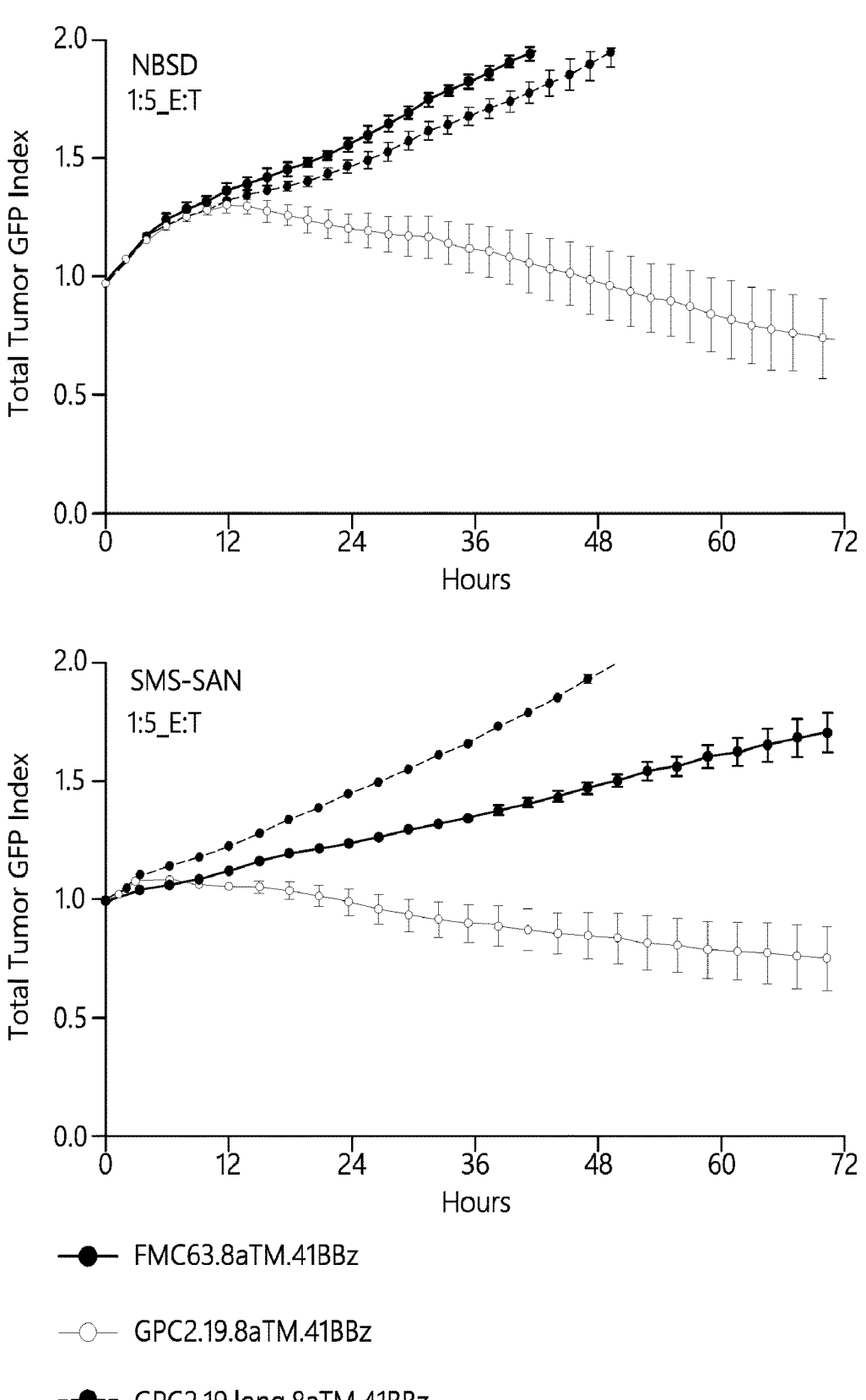

Previous studies have suggested that inclusion of an extracellular spacer domain can improve functionality of CAR T-cell constructs, in particular when targeting proximal epitopes on the tumor cell. To evaluate whether GPC2 CAR constructs with a spacer domain demonstrate enhanced functionality, GPC2.19 were cloned into retroviral expression vectors incorporating an IgG4 derived CH2CH3 spacer domain, mutated to reduce Fc receptor binding by myeloid cells (FIG. 4A). Both constructs expressed well on primary, activated T-cells, bound soluble, recombinant GPC2 (FIG. 4B) and expanded well in vitro (FIG. 4C). Nevertheless, long GPC2.19 constructs showed impaired production of IFNγ in response to tumor compared to their short counterparts without a spacer domain (FIG. 4D) and lacked cytolytic activity against native antigen density tumor cell lines NBSD (GPC2++) and SMS-SAN (GPC2+) when challenged with 5× excess of tumor, as well as at a 1:1 effector to target ratios (FIG. 4E). In conclusion, these findings indicate that incorporation of a spacer domain did not enhance functionality and implied that additional engineering was required to render GPC2-CAR potent enough to target native GPC2 site density.

Example 4

Figure 5:
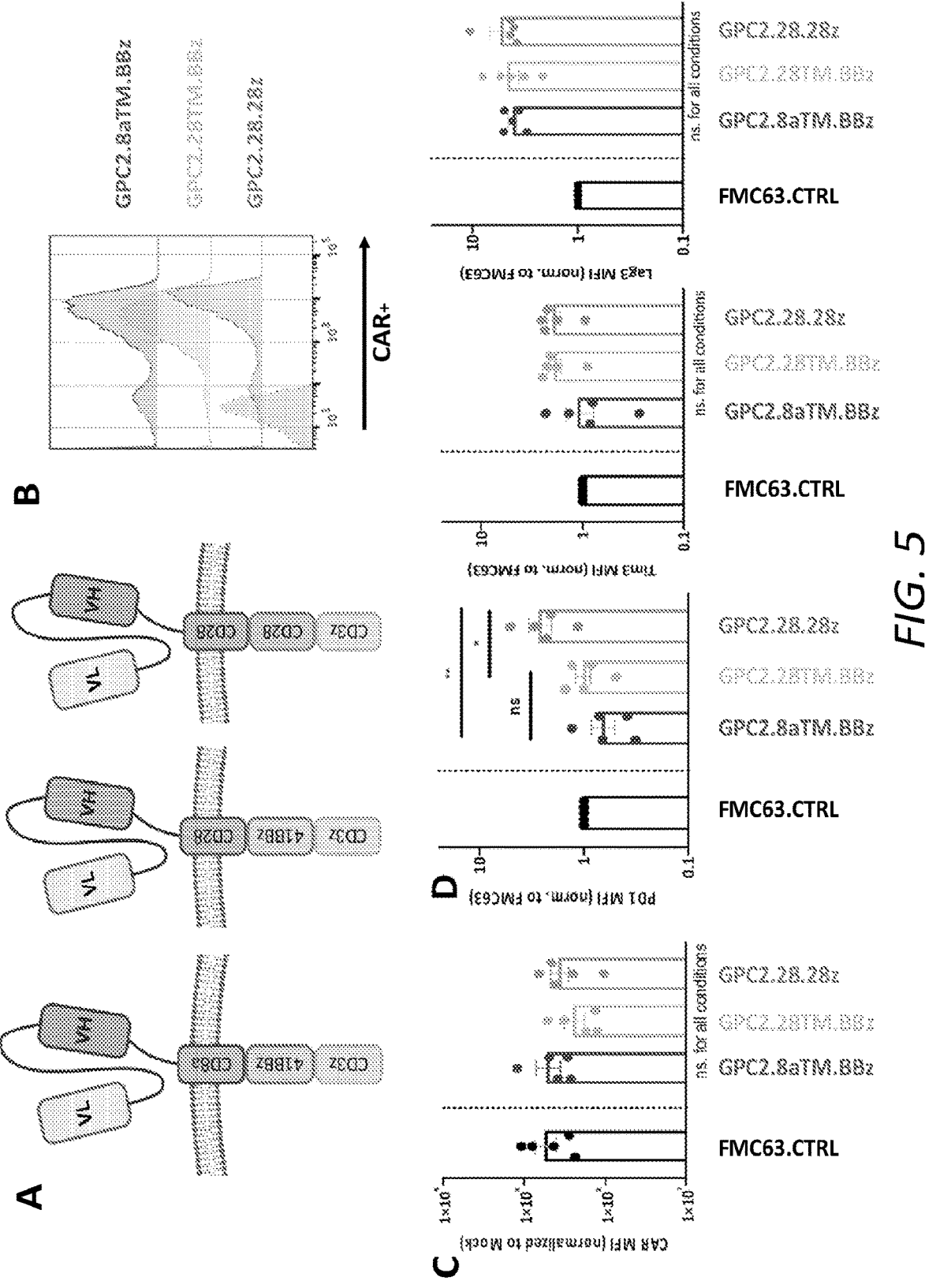
FIGS. 5A-5I graphically summarize the results of experiments performed to demonstrate that incorporation of CD28 hinge-transmembrane domains renders GPC2 CAR T-cells efficacious towards native target site density.
Figure 5:
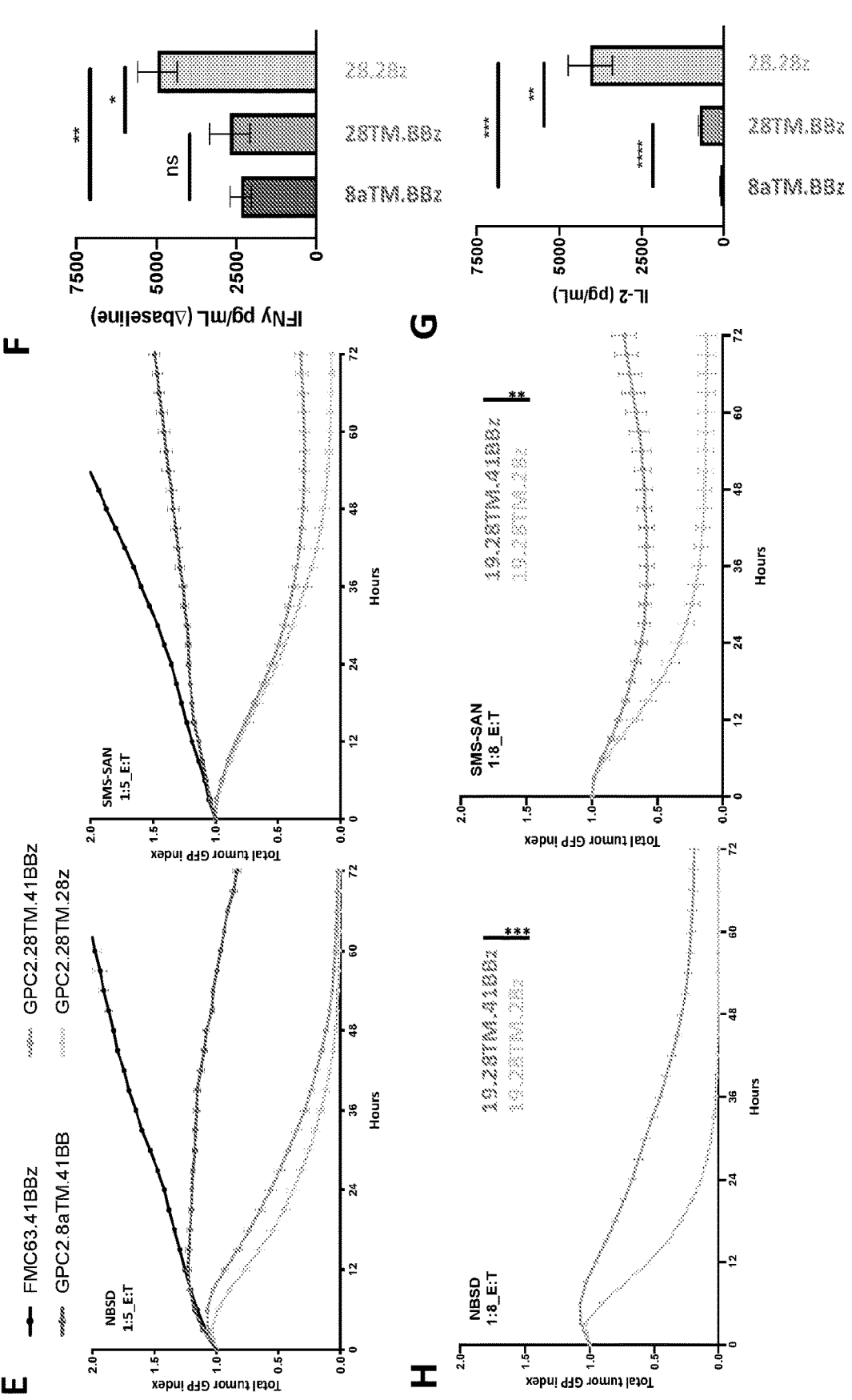
Figure 5I:
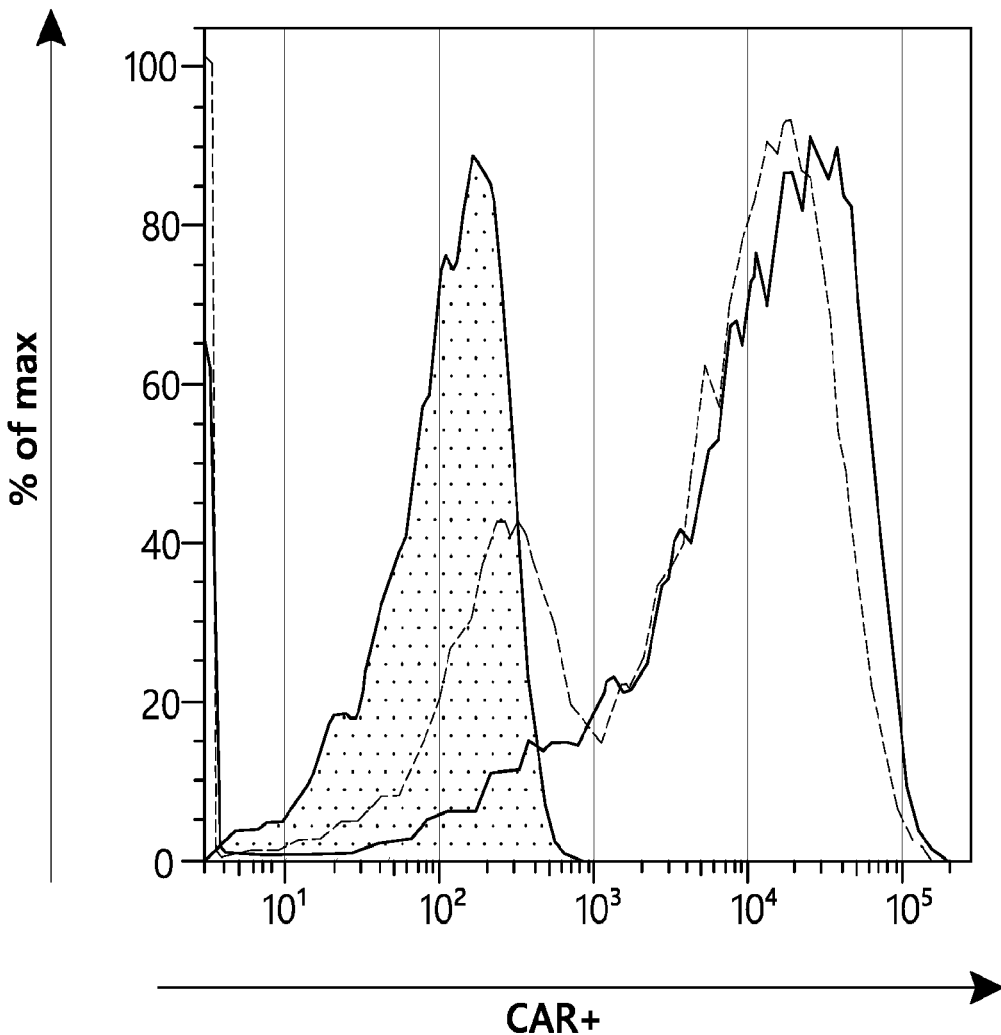
Figure 6A:
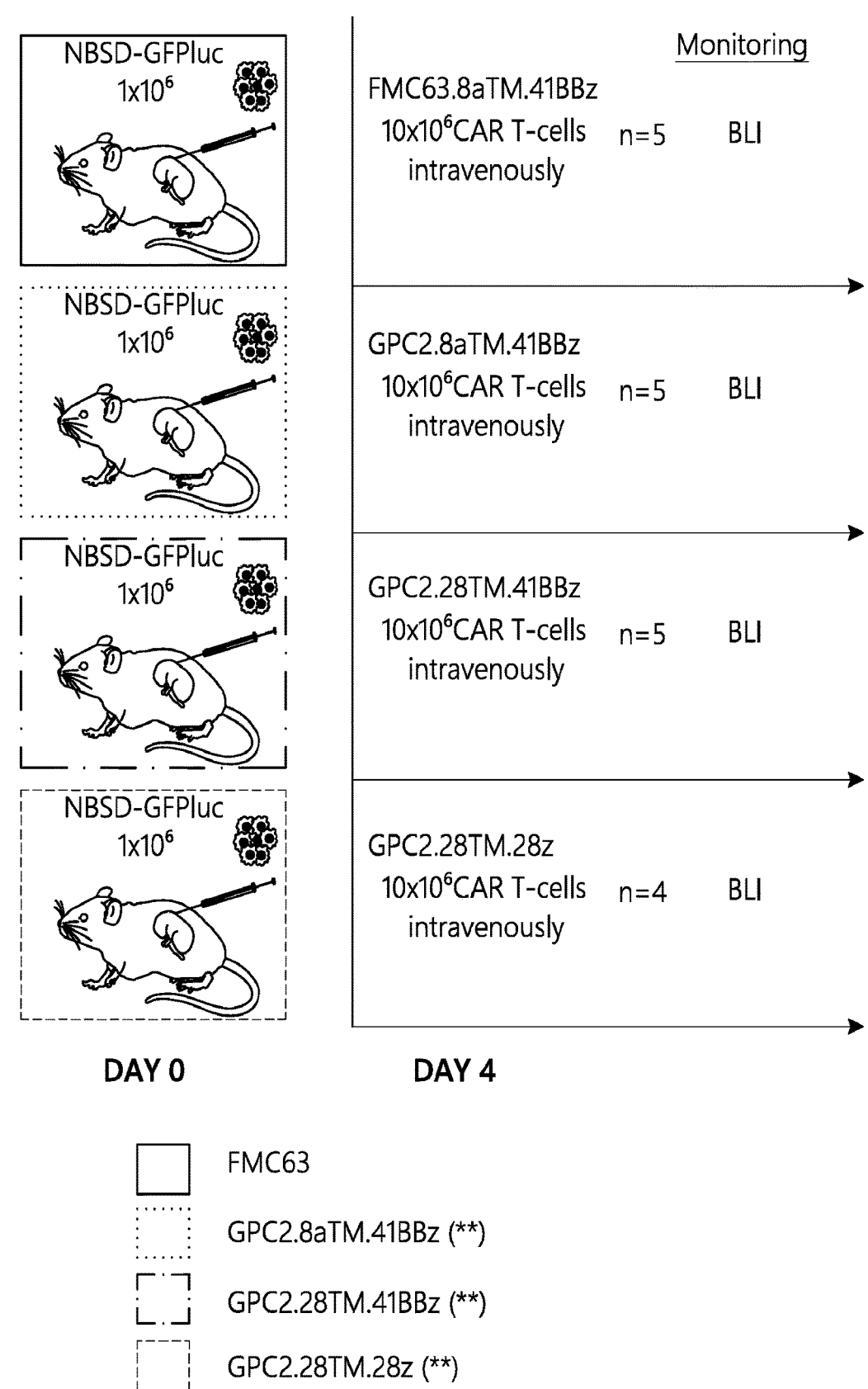
FIGS. 6A-6G graphically summarize the results of experiments performed to demonstrate that optimized GPC2 CAR T-cells effectively control native antigen density tumors in representative in vivo xenograft models.
Figure 6B:
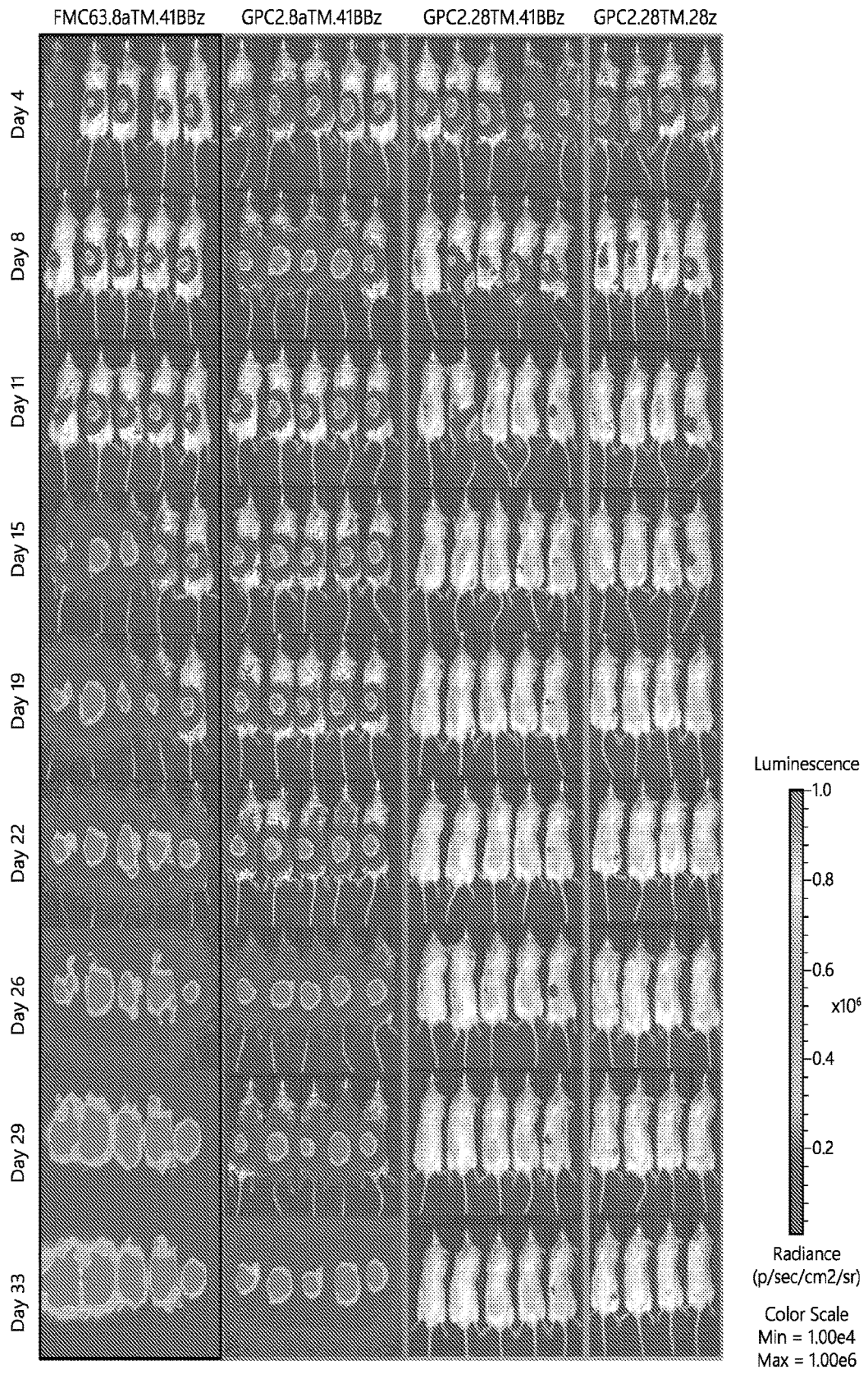
Figures 6C, 6D:
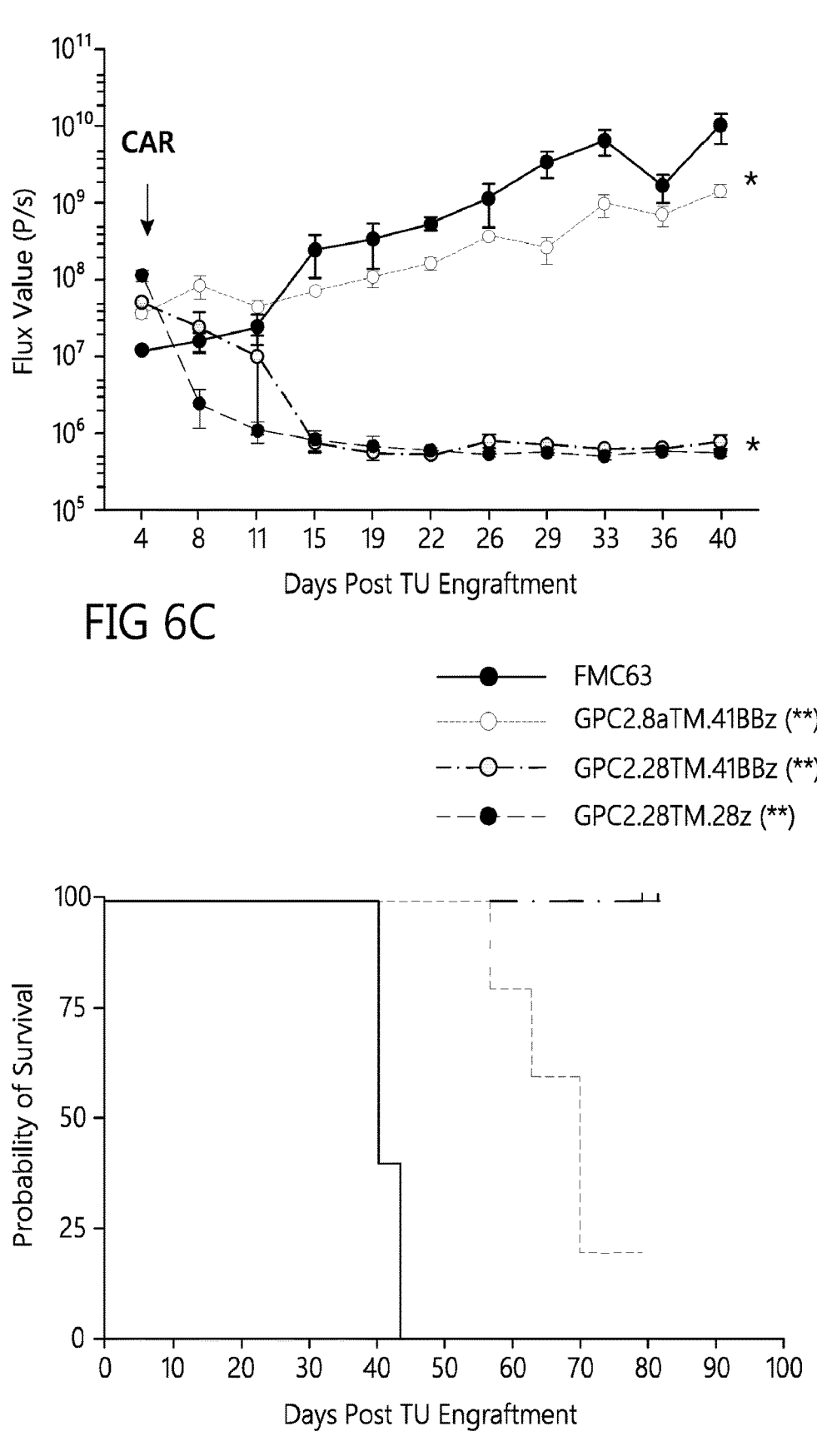
Figure 6E:
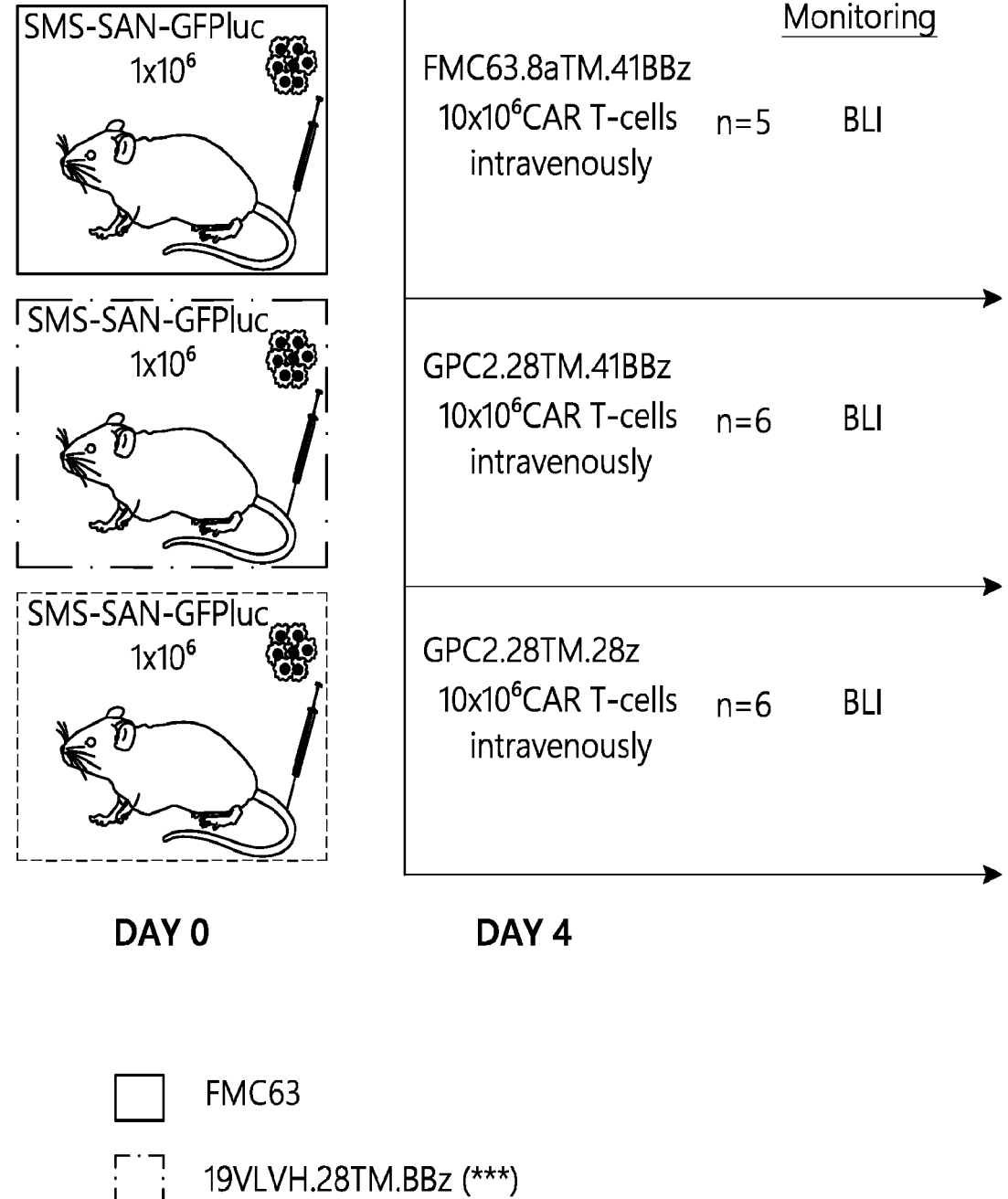
Figure 6F:
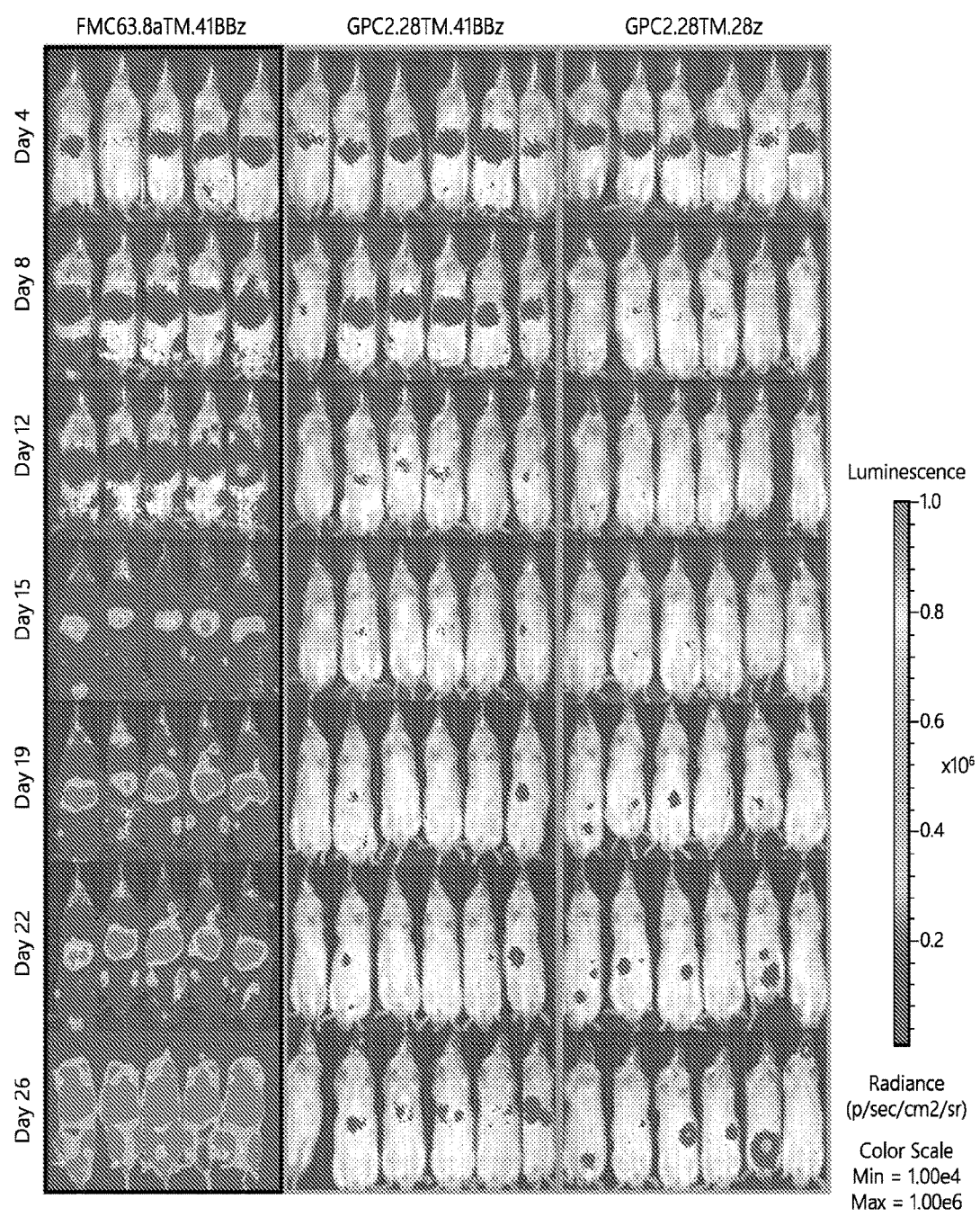
Figure 6G:
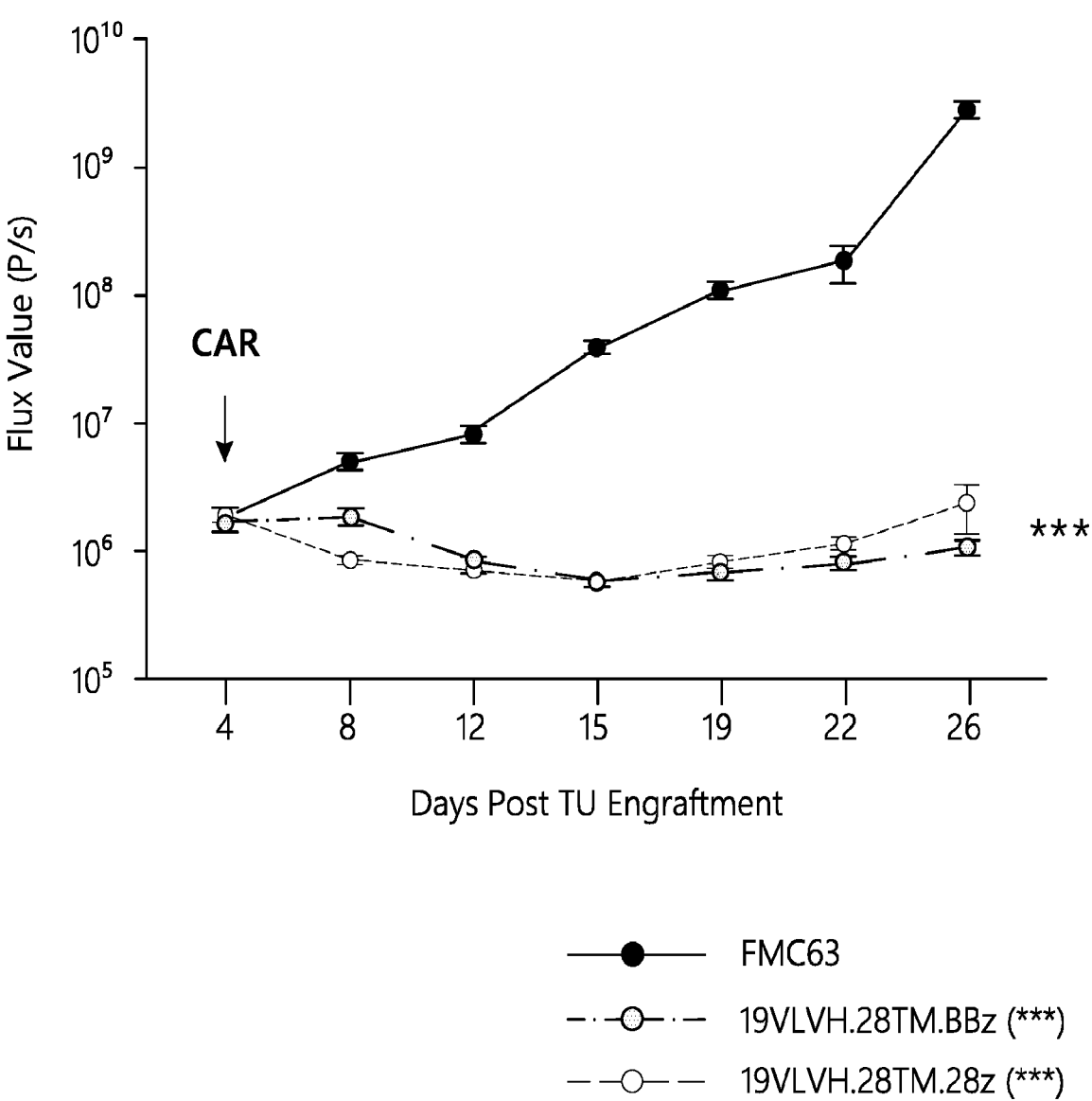
Figure 6:
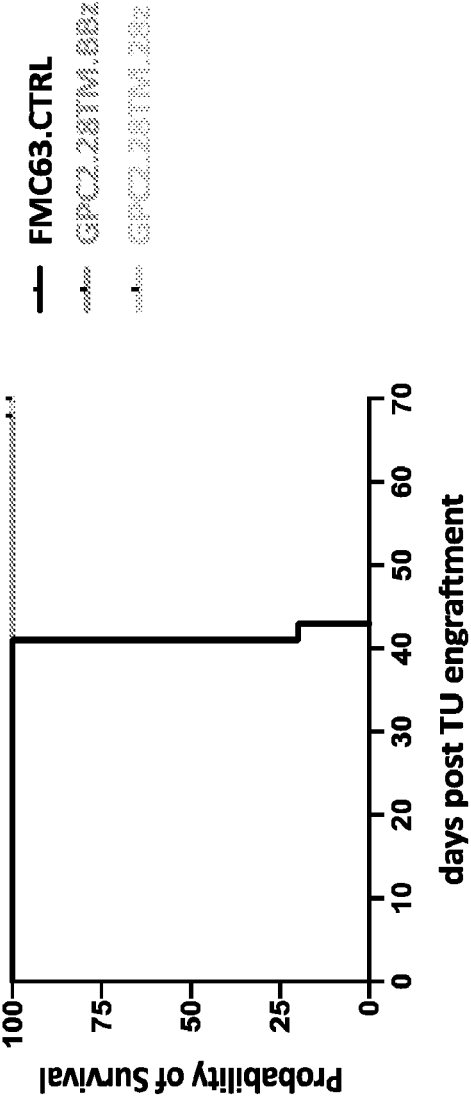
FIG. 6H: Kaplan-Meier survival analysis of treatment arms shown in FIG. 6E.
Figure 6:

Incorporation of CD28 Hinge-Transmembrane Domains Renders GPC2 CAR T-Cells Efficacious Towards Native Target Site Density Tumors Given that GPC2.19 CAR T-cells express well on the surface of primary T-cells and show proper binding to soluble recombinant antigen (FIG. 2C) and the inclusion of a spacer domain did not result in improved functionality, transmembrane and signaling domains were modulated in an attempt to lower the activation threshold. CAR T-cell constructs incorporating CD28 transmembrane domains, and/or CD28 signaling domains were tested for their activity in the context of GPC2.19 CAR constructs (FIG. 5A). These GPC2.19 CAR constructs did not exhibit differences in their cell surface expression on activated T-cells after retroviral transduction (FIGS. 5B and 5C) and or exhaustion profiles (FIG. 5D). However, incorporating CD28 hinge-transmembrane domains instead of CD8a in second generation GPC2.19 CAR T-cell constructs possessing either 41BB signaling or CD28 signaling domains drastically ameliorated cytolytic activity against GPC2\ cell lines NBSD (GPC2++) and SMS-SAN (GPC2+) in vitro, when challenged with 5× excess tumor while constructs incorporating CD8aTM.41BBz constructs fail (FIG. 5E). In addition, improved cytokine production of IFNγ and IL-2 in response to native antigen density tumor cell lines NBSD (GPC2++) was observed (FIGS. 5F and 5G). When challenged with even higher tumor excess (1:8 effector to target ratios), constructs incorporating CD28 hinge-transmembrane domains and CD28 costimulatory domains and outperformed those with 41BBz costimulatory domains (FIG. 5H). Those differences are not related to differences in CAR cell surface expression (FIG. 5I).

These improved results are mirrored by strikingly improved in vivo effects, as all constructs incorporating CD28 hinge-transmembrane domains with either CD28 or 41BB co-stimulatory domains mediated complete responses in GPC2' site density tumor bearing mice engrafted with neuroblastoma tumor cells (NBSD: GPC2++) into the subrenal capsule in an orthotopic manner, while constructs incorporating the original CD8a hinge-transmembrane domain and 41BB costimulatory domains only show a modest anti-tumor effect (FIGS. 6A-6D). Similar anti-tumor responses were achieved in a metastatic model of neuroblastoma, in which mice were engrafted with GPC2\ cell lines SMS-SAN (GPC2+) via tail vein injection. Again, GPC2.19 CAR T-cell constructs incorporating CD28 hinge-transmembrane domains with either CD28 or 41BB co-stimulatory domains mediated complete responses in this model and led to a significant survival advantage (FIGS. 6E-6H). In conclusion, we have optimized GPC2 CAR T-cell constructs for the ideal scFv, orientation of variable light and heavy chains, distance between the CAR T-cell and the targeted epitope, transmembrane and signaling domains to effectively target native GPC2 site density on tumors.

Example 5

GPC2 CAR T-Cells Control Tumor without Evidence of Toxicity

Figure 7:
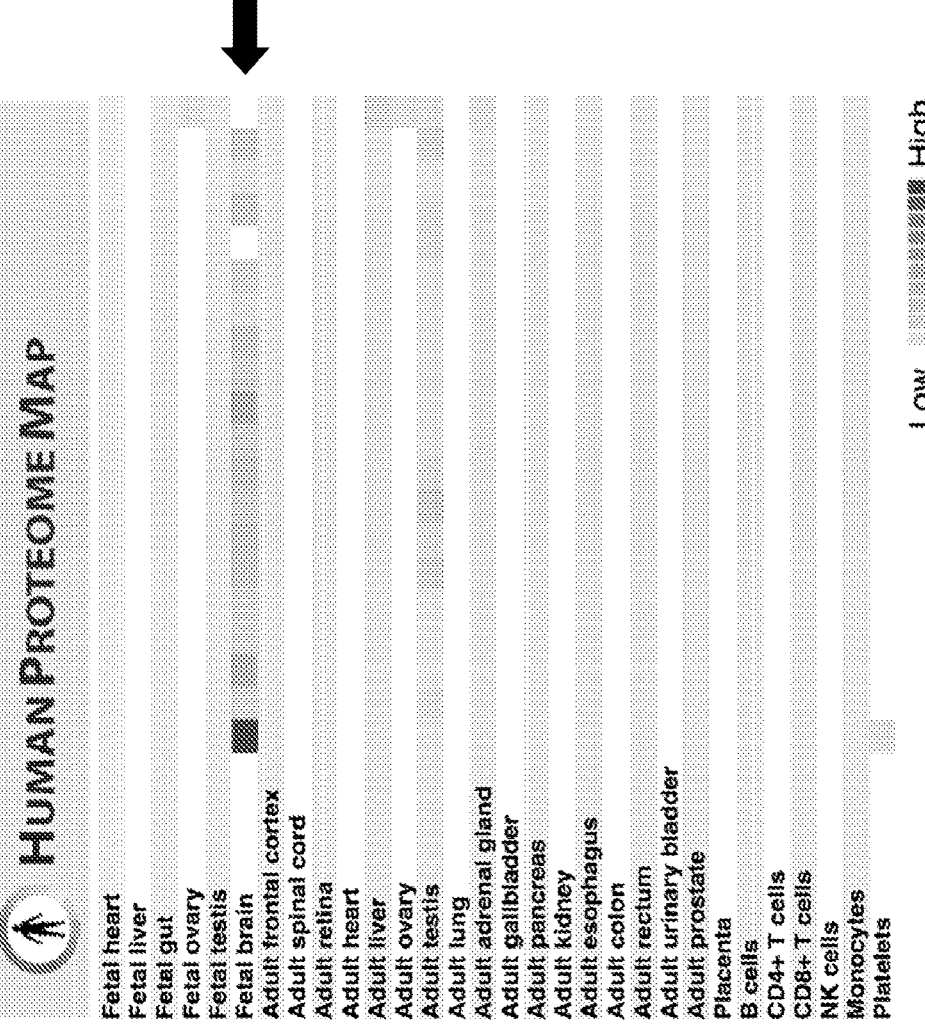
FIG. 7 graphically summarize the results of findings illustrating that GPC2 expression is restricted to fetal brain development. Protein expression of GPC2 in various normal tissues and organs assessed by Mass Spectrometry sourced from the Human Proteome Map.
Figure 8A:
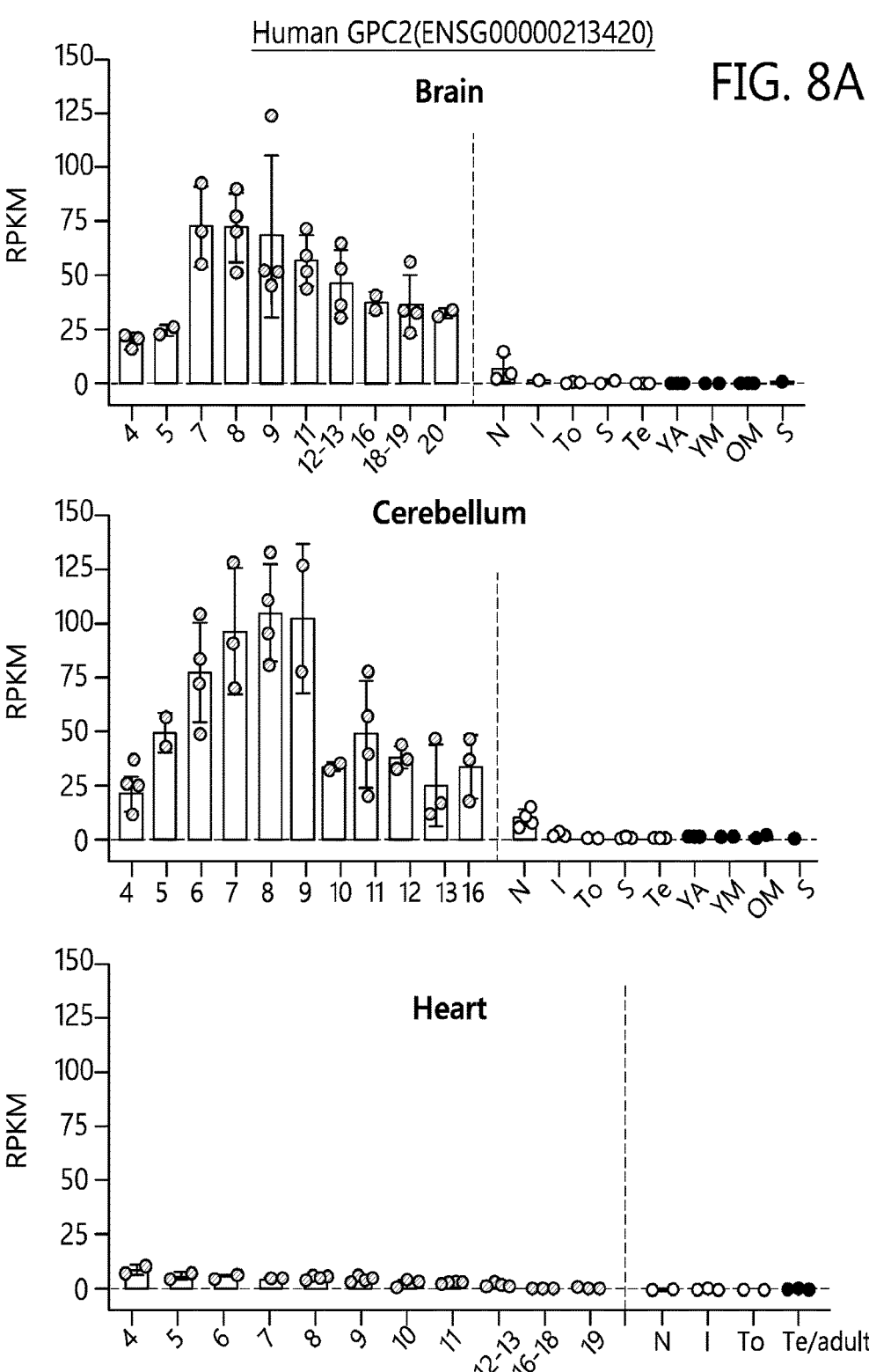
FIGS. 8A-8B graphically summarize the results of findings illustrating that pattern of GPC2 expression restricted to fetal brain is similar between murine and human tissues.
Figure 8A:
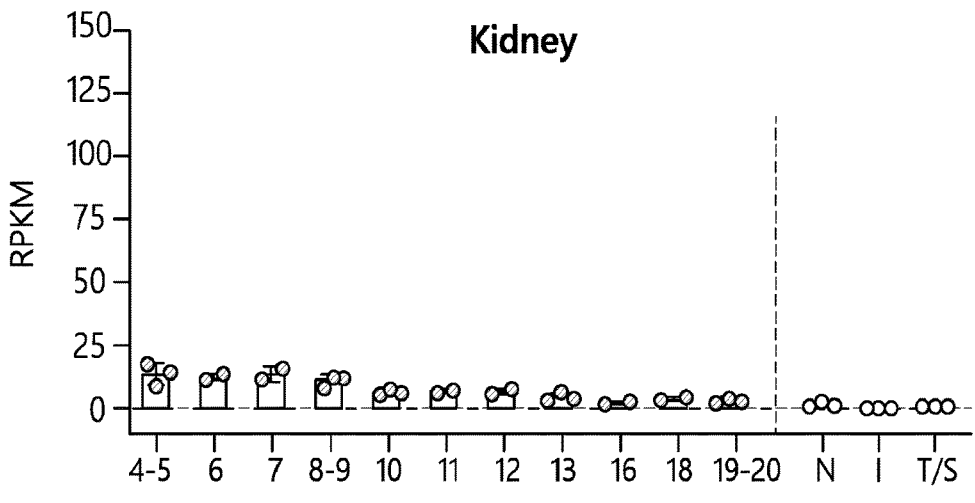
Figure 8A:
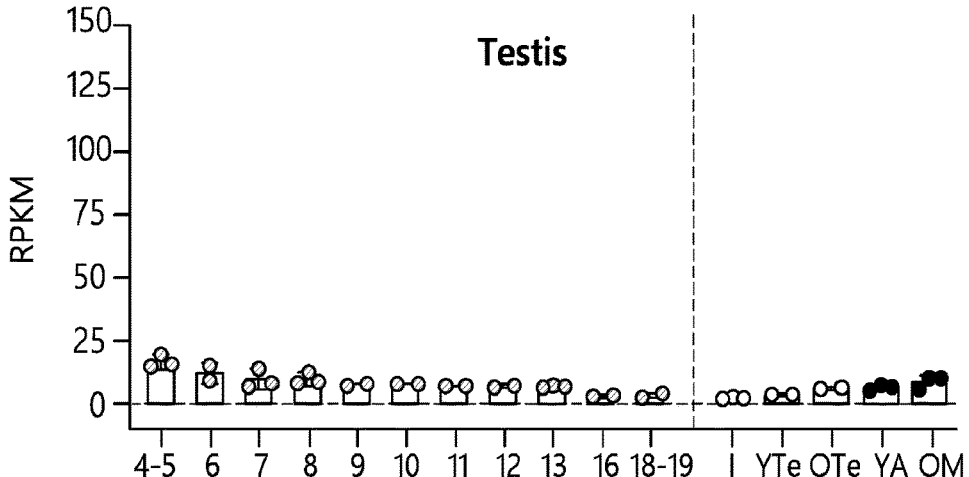
Figure 8B:
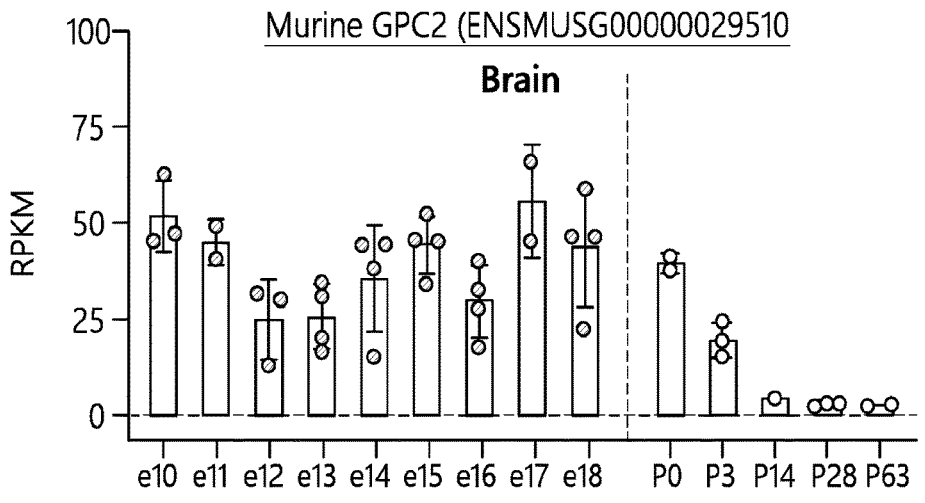
Figure 8B:
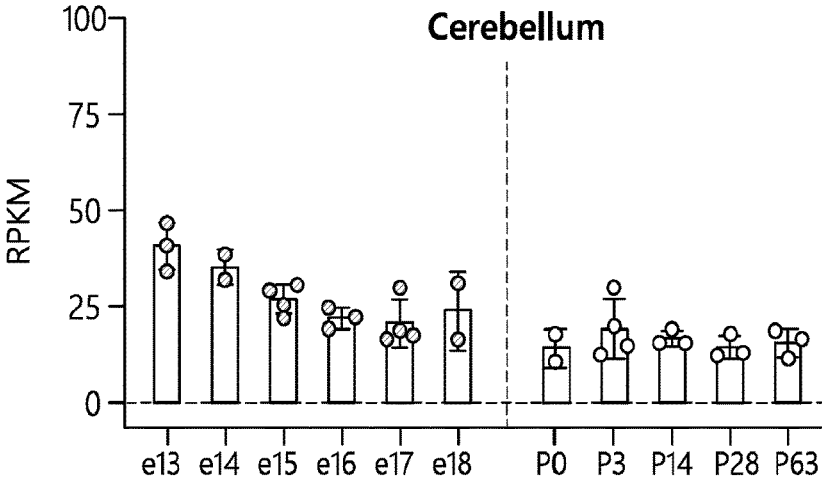
Figure 8B:
Figure 8B:
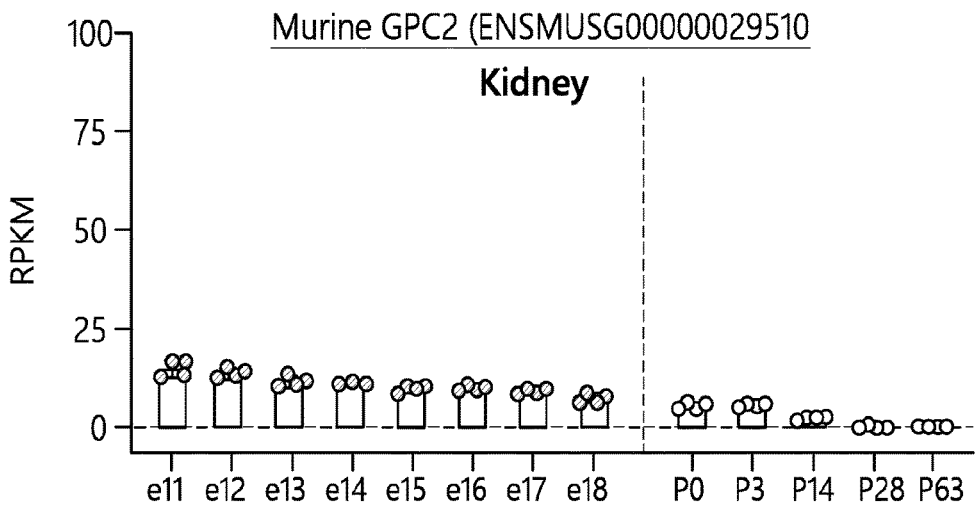
Figure 8B:
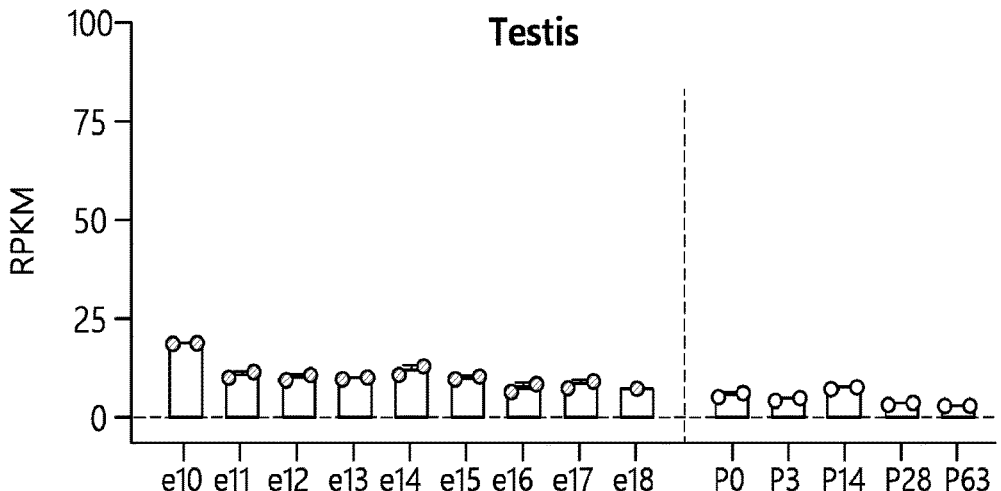
Figure 9:
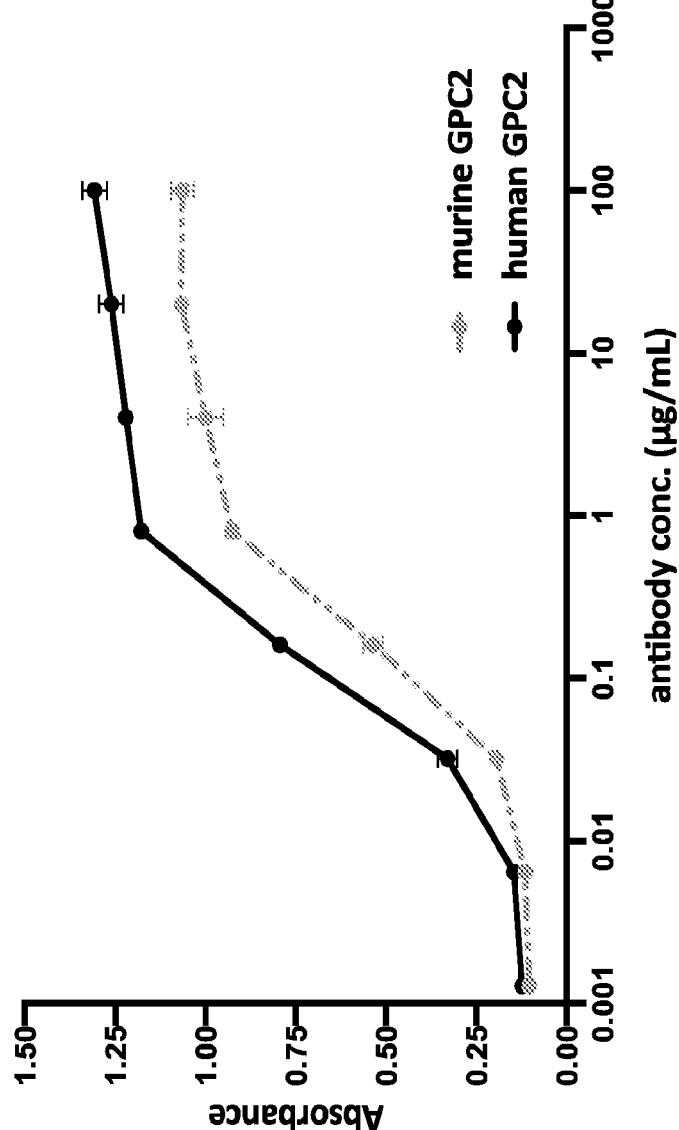
FIGS. 9A-9D graphically summarize the results of experiments illustrating that GPC2.CAR T-cells specifically recognize human and murine GPC2.
Figure 9B:
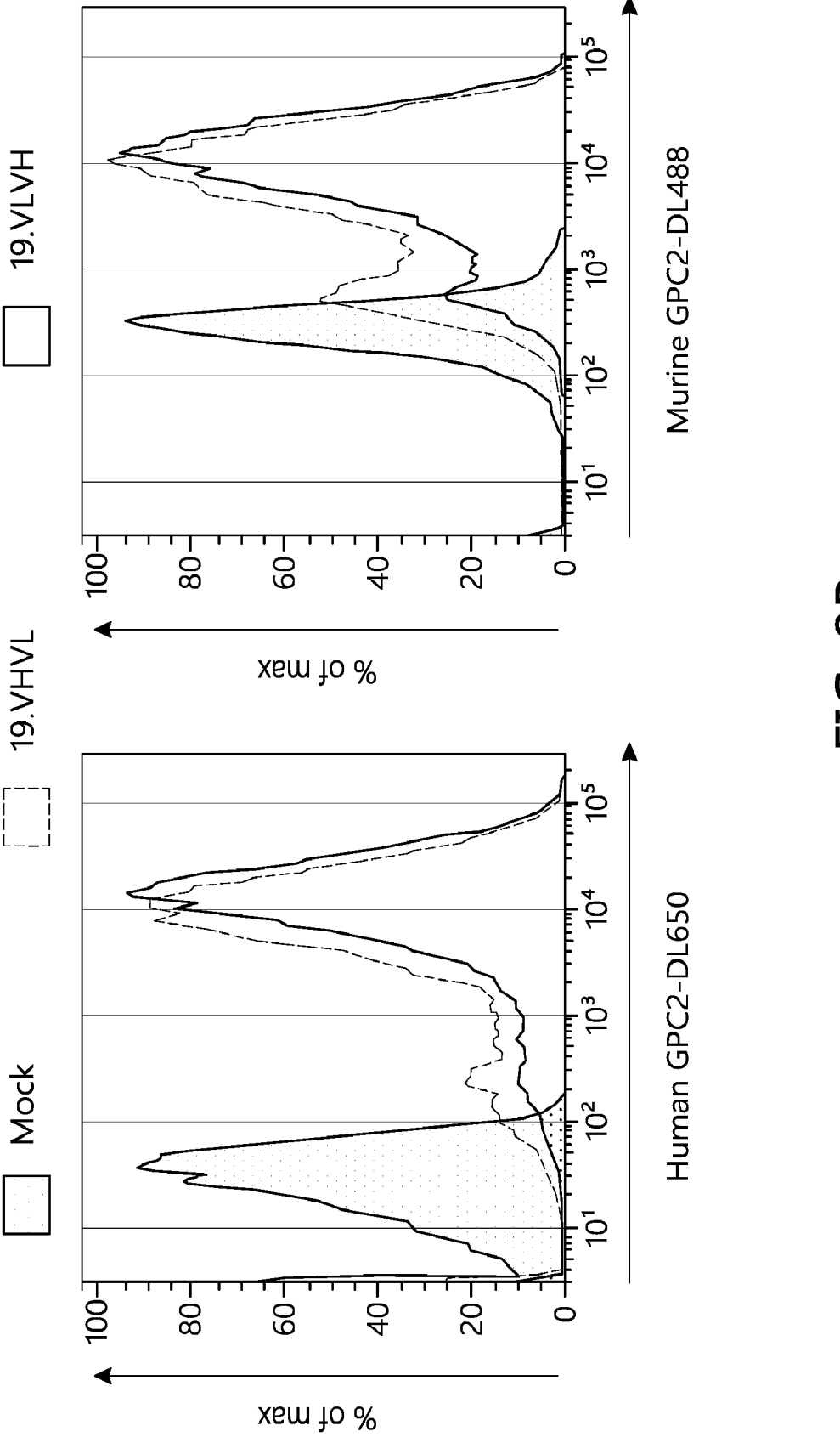
Figure 9:
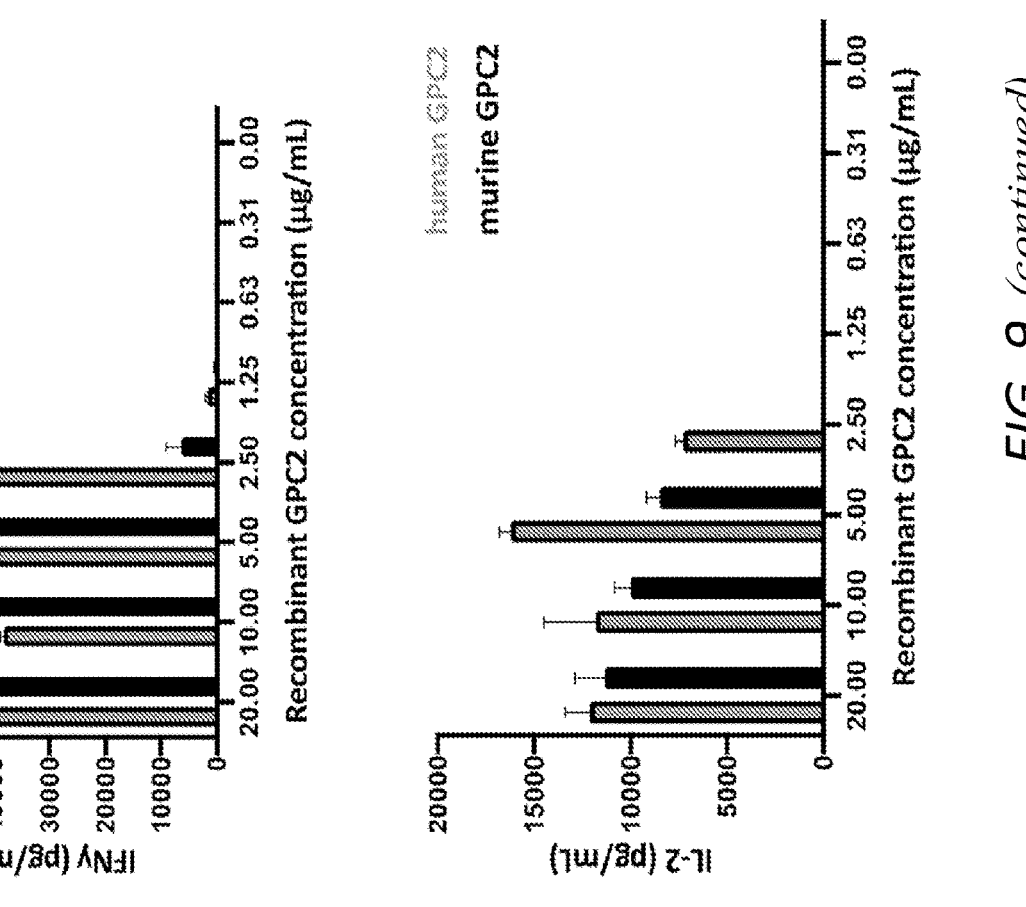
Figure 10A:
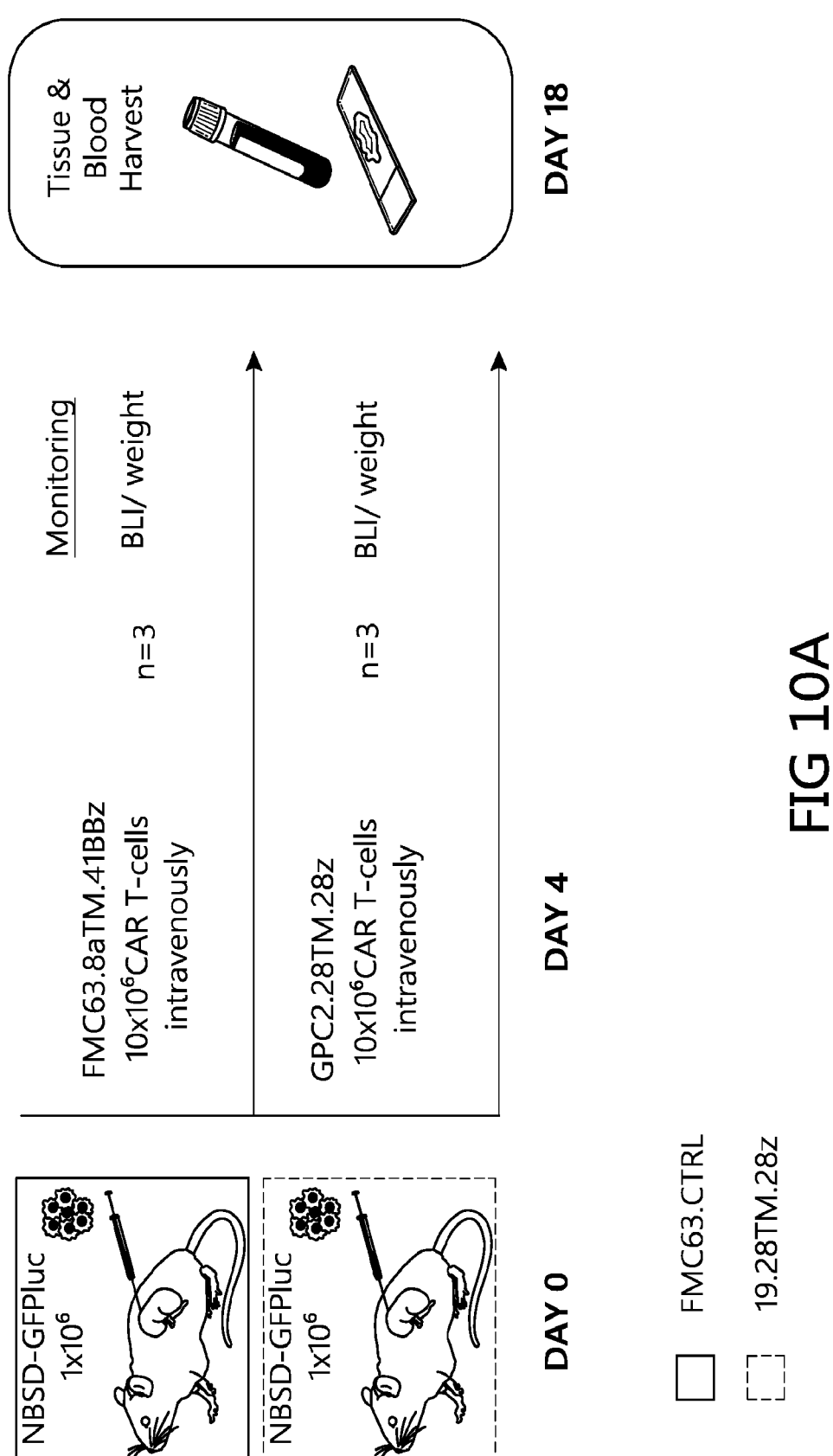
FIGS. 10A-10F graphically summarize the results of experiments performed to demonstrate that GPC2.CAR T-cells control tumor without evidence of toxicity.
Figure 10D:
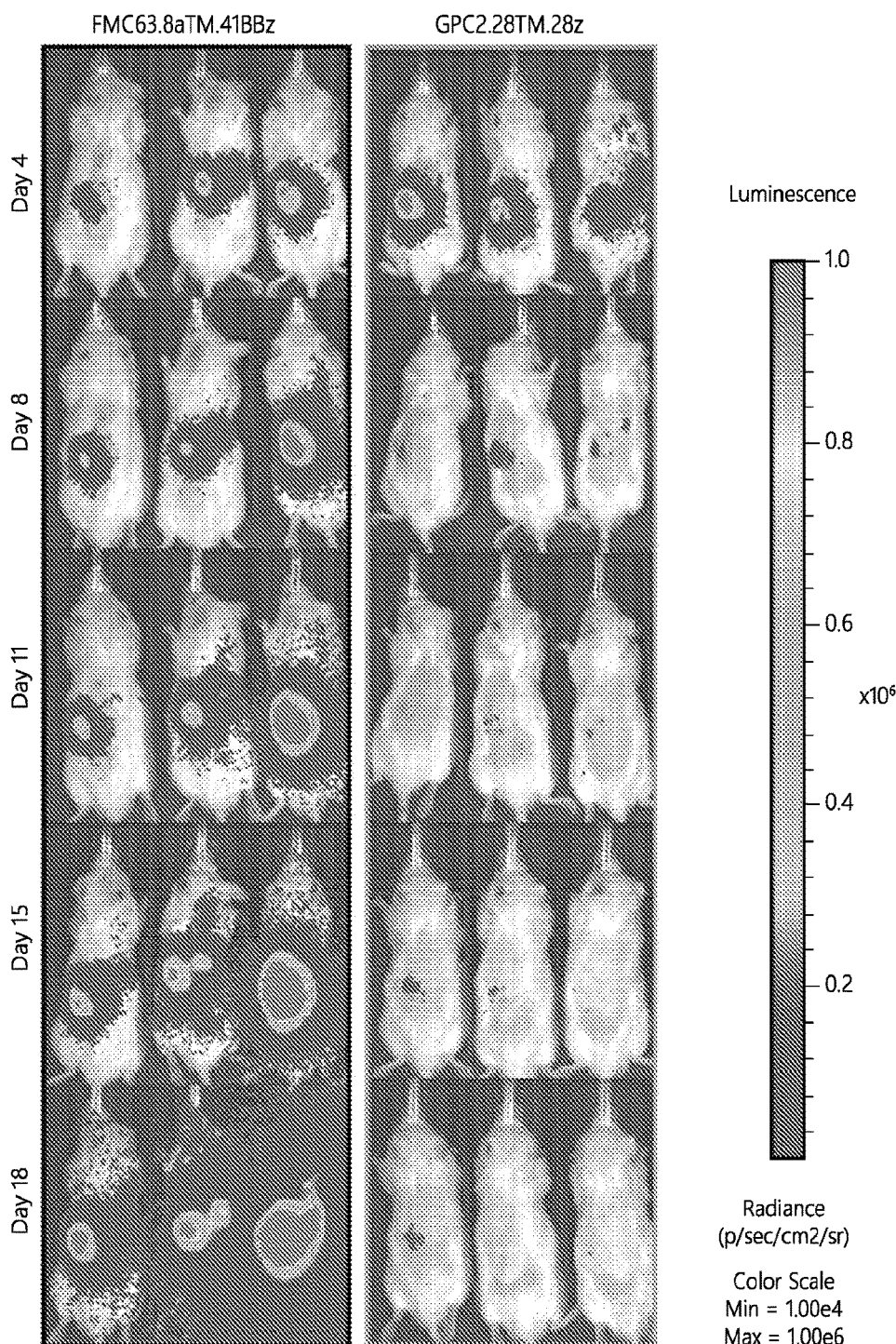
Figure 10E:
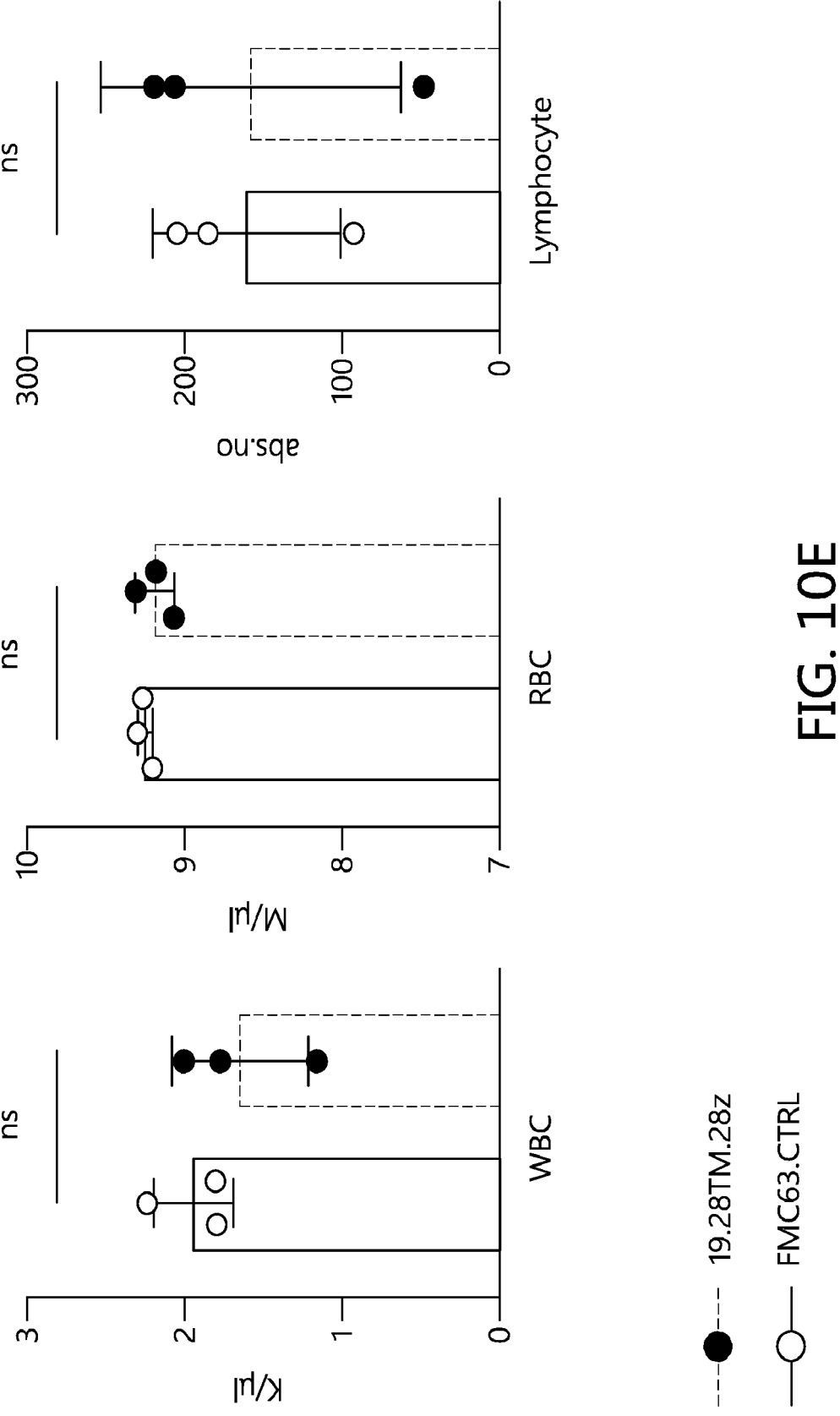
Figure 10E:
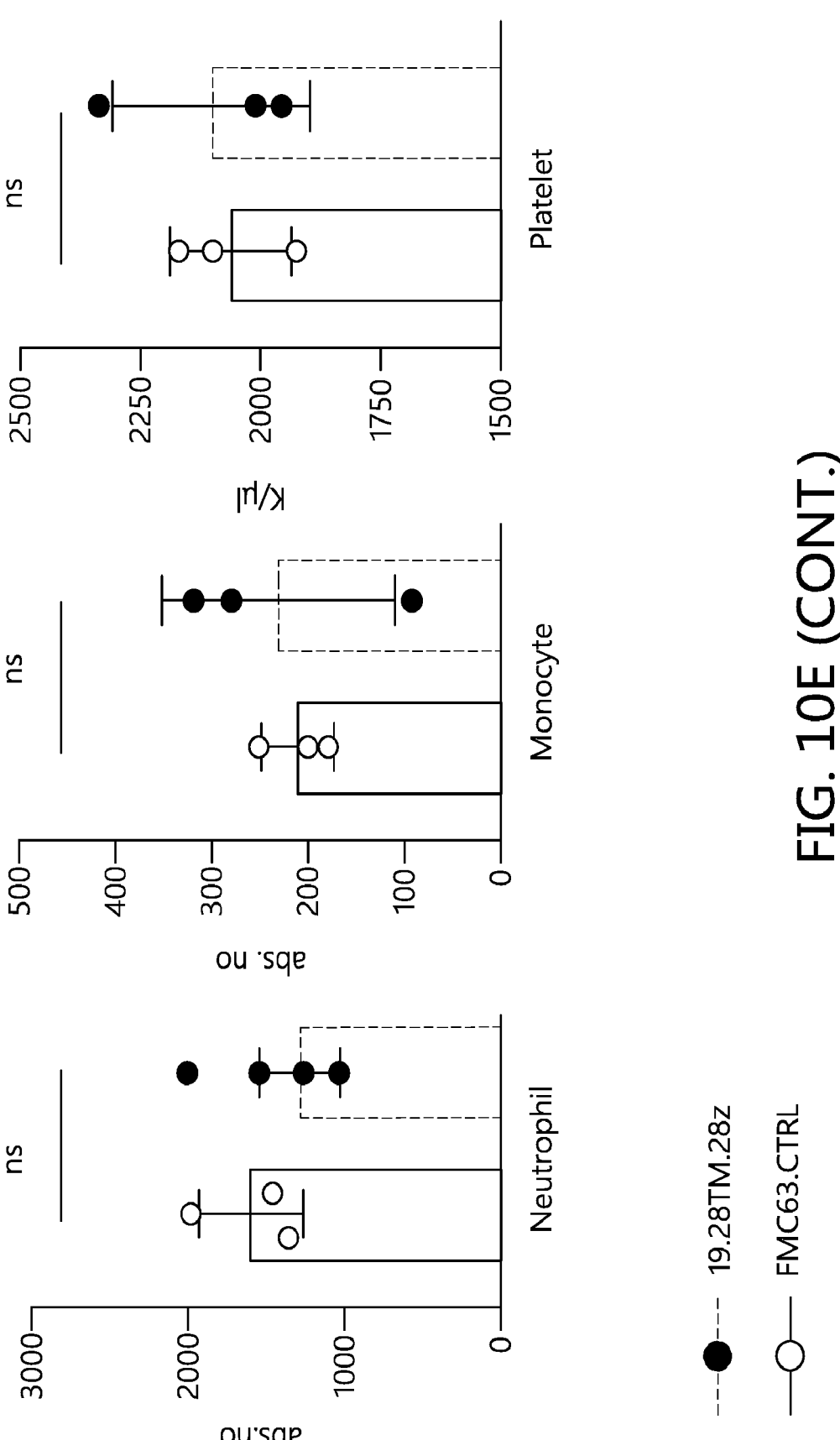
Figure 10E:
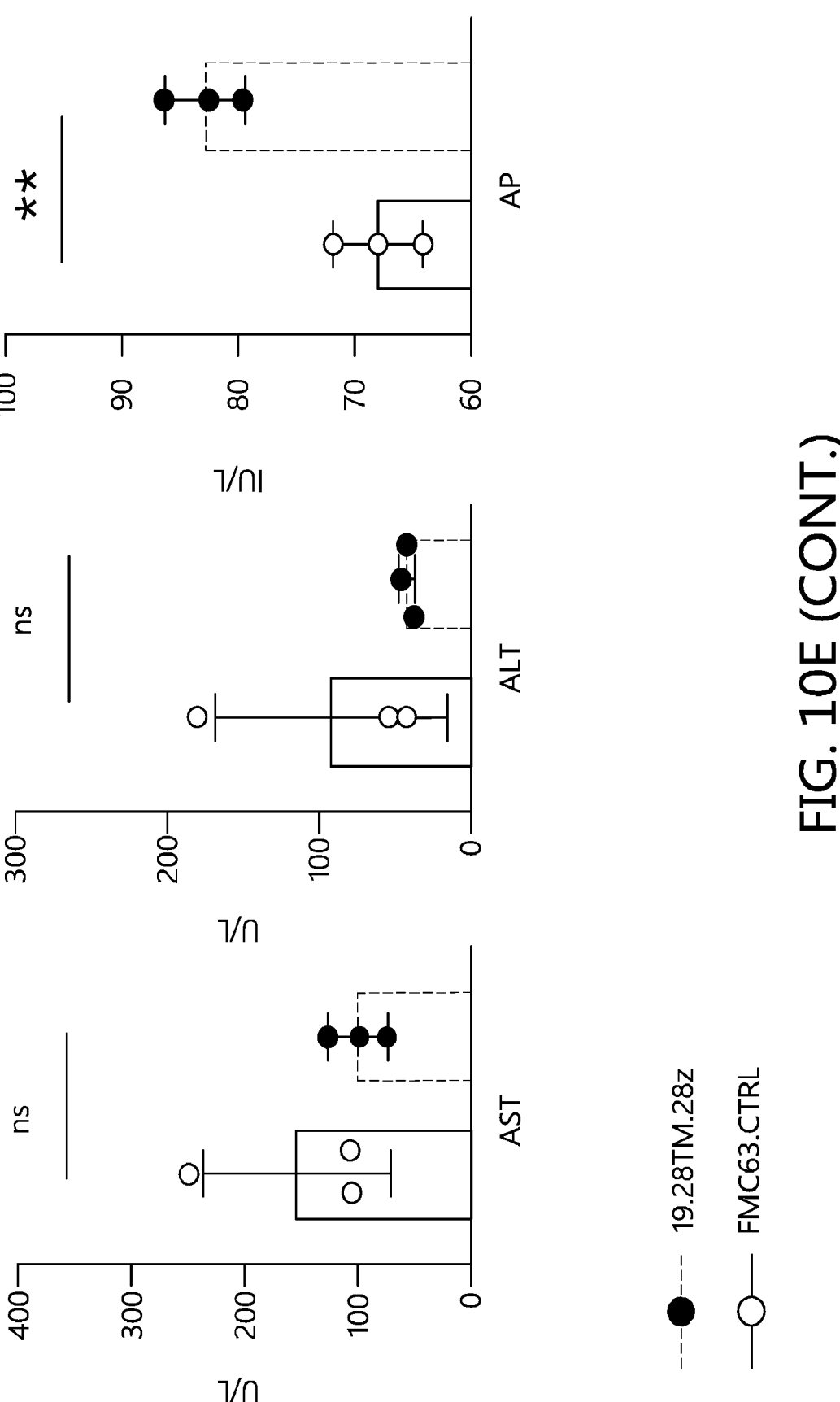
Figure 10:
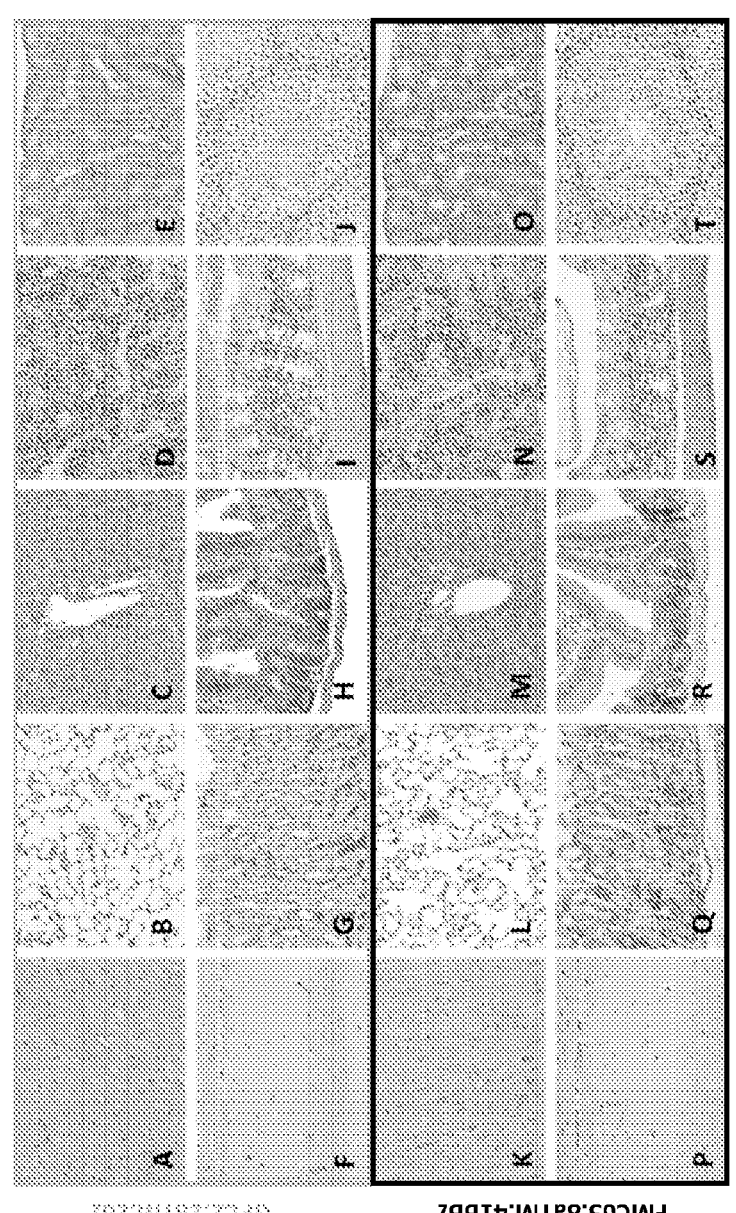
Figure 10:

Additional experiments were performed to evaluate the safety of our lead-candidate CAR construct and address potential on-target/off-tumor toxicity of GPC2-directed CAR T-cells in a relevant in vivo disease model. In normal tissues, GPC2 protein expression is restricted to fetal brain development (FIG. 7). Gene expression patterns are shared between human and murine GPC2 in fetal brain, which is silenced after birth (FIGS. 8A-8B). To assess whether our GPC2.19 CAR T-cells can recognize murine GPC2 in a similar manner, we assessed the binding of GPC2.19-IgG1 to murine and human GPC2 by ELISA and observed a comparable binding capacity (FIG. 9A), indicating cross-recognition. Likewise, GPC2.19 CAR T-cells expressed on activated T-cells were able to recognize both murine and human recombinant GPC2 (FIG. 9B) and showed effective cytokine production against plate-bound human and murine GPC2 (FIGS. 9C-9D). Thus, we chose our previously established subrenal capsule neuroblastoma xenograft model for assessment of any potential on-target/off-tumor effects. Tumor bearing mice, treated with either GPC2.19 CAR-T cells or FMC63 control CAR-T cells were submitted for necropsy and blood analysis 14 days post treatment (FIG. 10A). Despite the expected anti-tumor effect implying CAR T-cell activation and proliferation (FIGS. 10B and 10D), animals exhibited no weight loss or clinical sign of toxicity (FIG. 10C), significant changes in blood cell counts or liver enzymes AST/ALT (F FIG. 10E), the only exception being increased levels of Alkaline Phosphatase. As evaluated by a blinded pathologist, all tissues examined were grossly and histologically within normal limits for both GPC2 CAR treated and FMC63 control-treated animals (FIG. 10F) including heart (A, K), lung (B, L), liver (C, M), spleen (D, N), kidney (E, O), brain (F, P), stomach (G, Q), small intestine (H, R), colon (I, S), and testes (J, T). In conclusion, GPC2.19 CAR T-cells effectively control tumor in representative disease models without evidence of toxicity.

Example 6

Figure 11A:
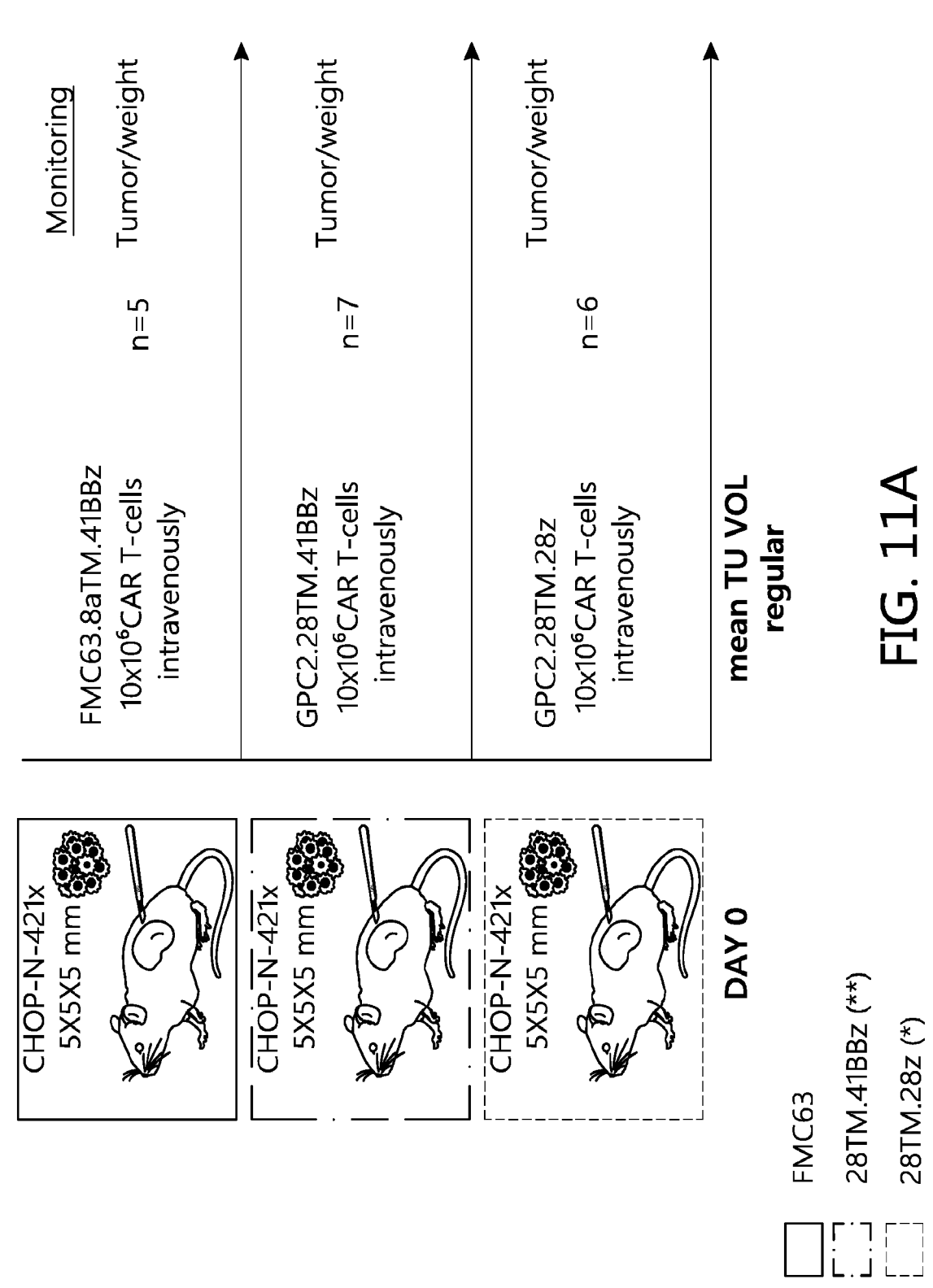
FIGS. 11A-11H graphically summarize the results of experiments performed to demonstrate that GPC2 CAR T-cells control regular and high tumor in patient-derived xenograft model.
Figure 11:
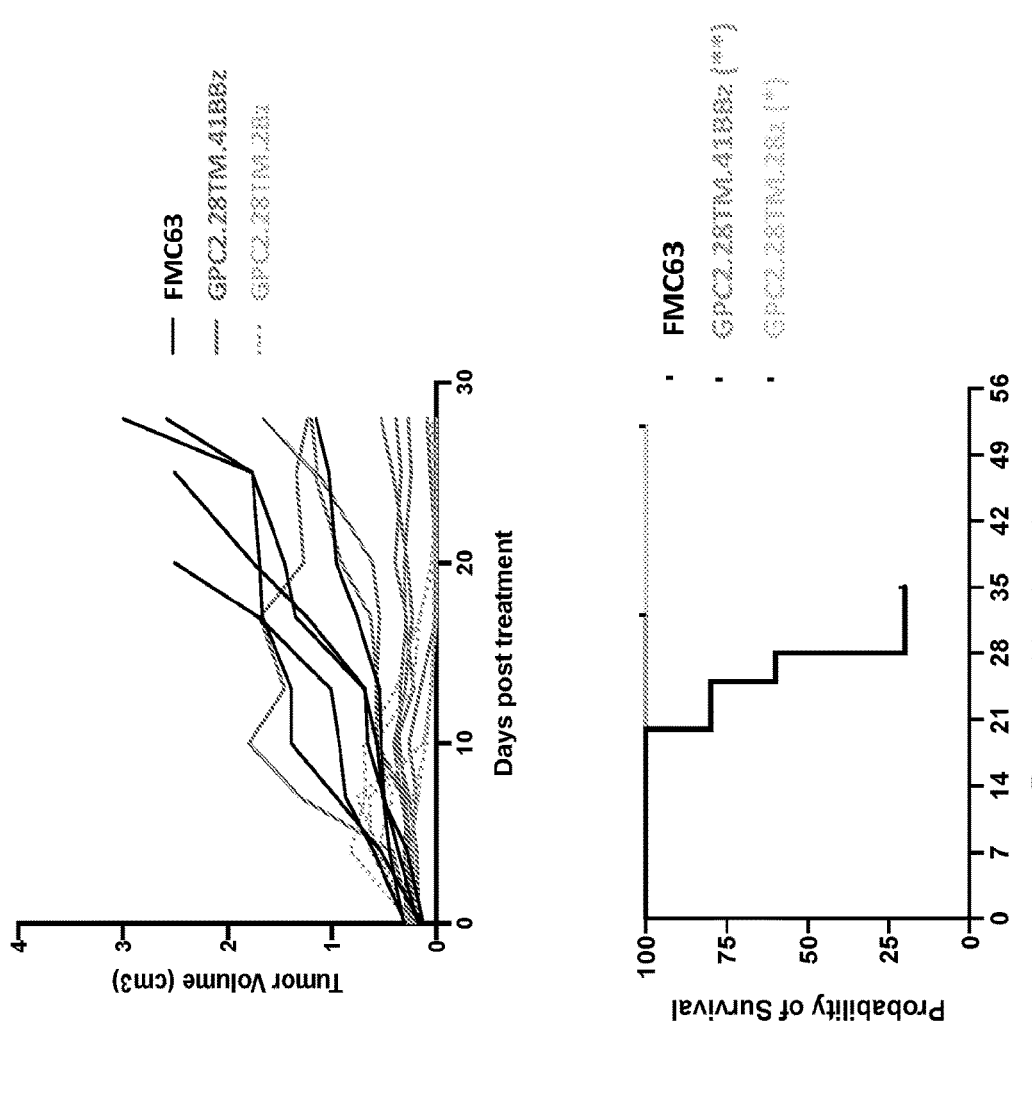
Figure 11:
Figure 11D:
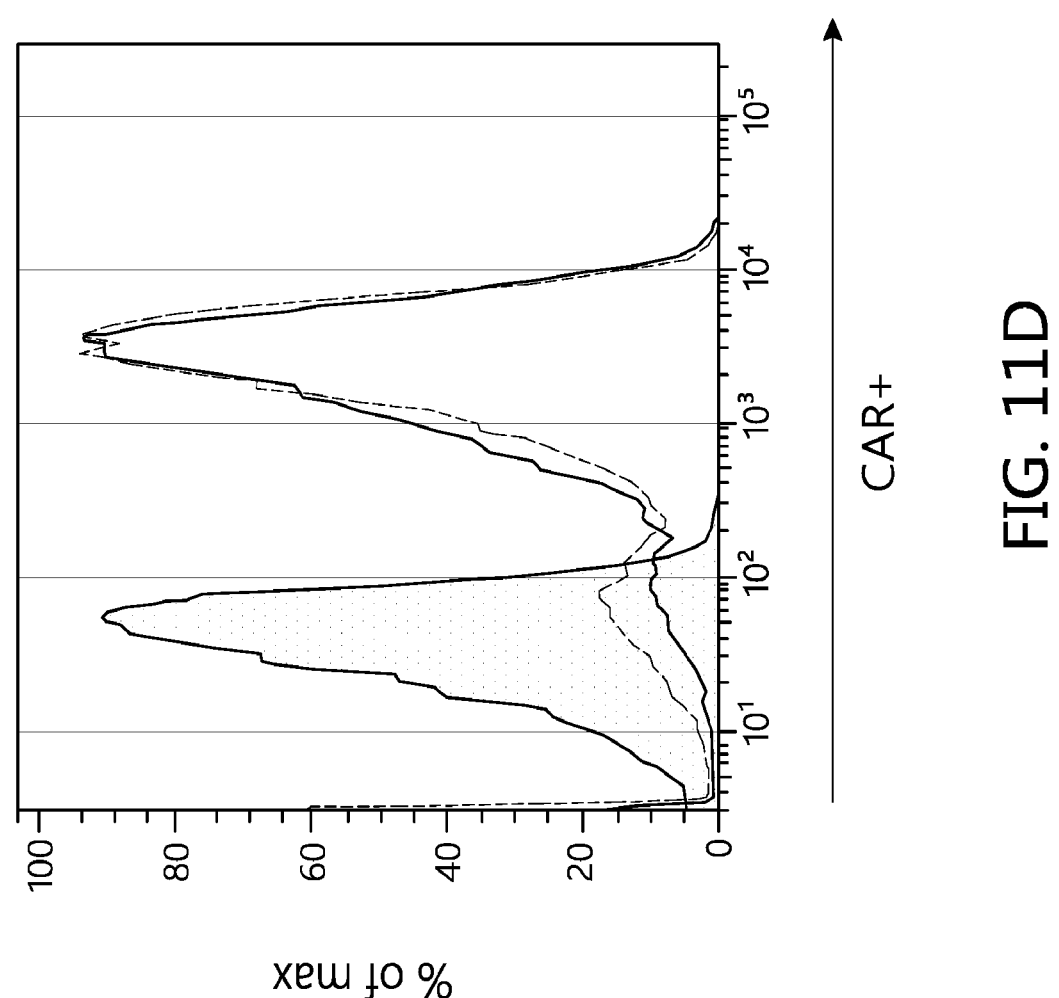
Figure 11E:
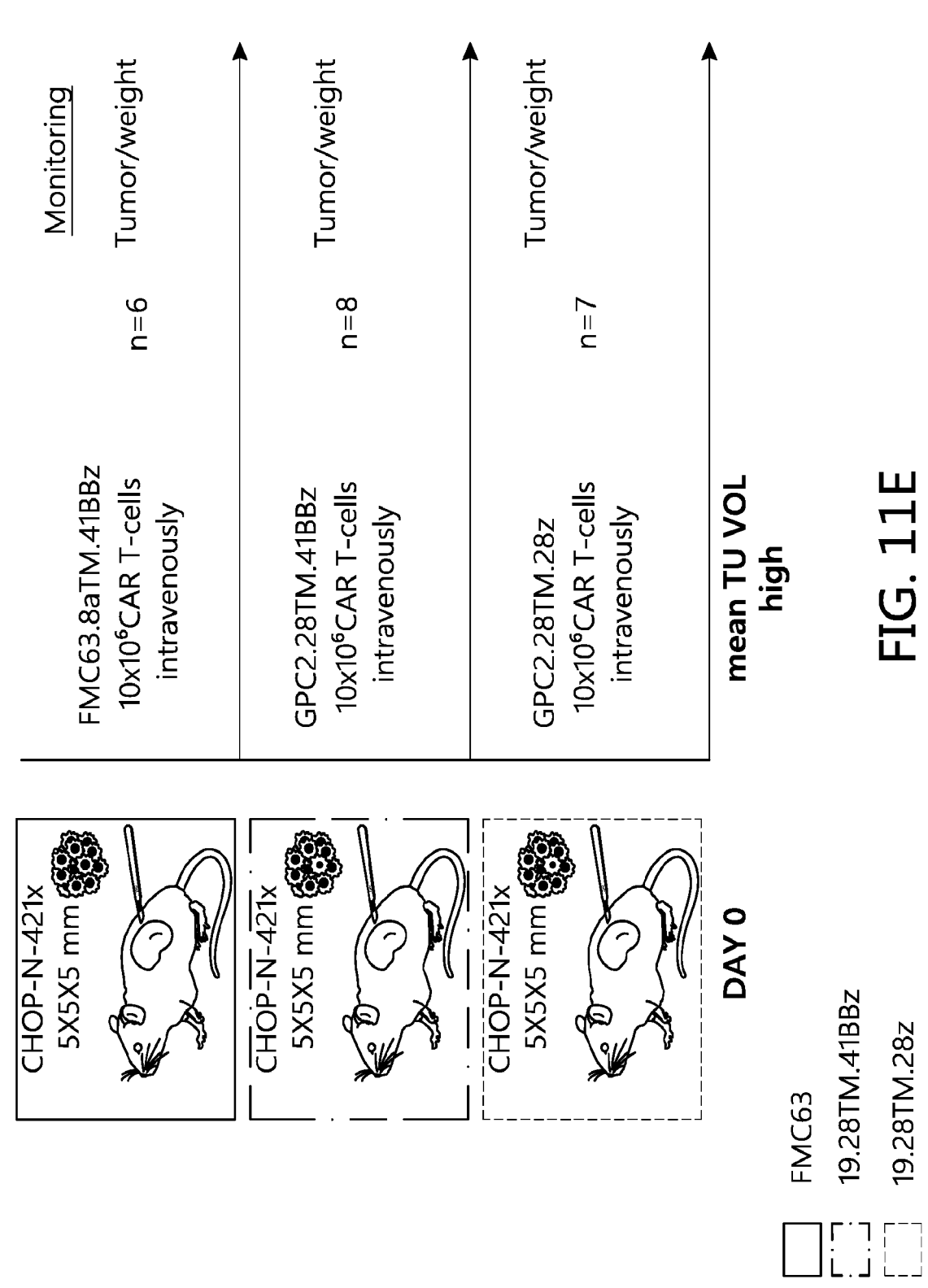
Figure 11:
Figure 12:
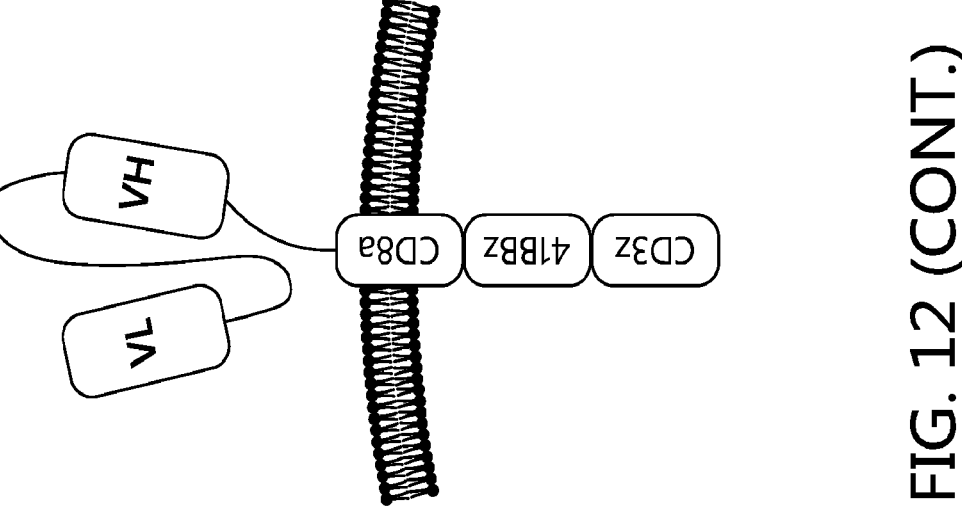
FIG. 12 is a schematic diagram of an exemplary GPC2-targeting CAR in accordance with some embodiments disclosed herein, GPC2.19VLVH.8aH-8aTM.41BBz (SEQ ID NO: 17). The amino acid sequences corresponding to each of the components are shown.
Figure 14:
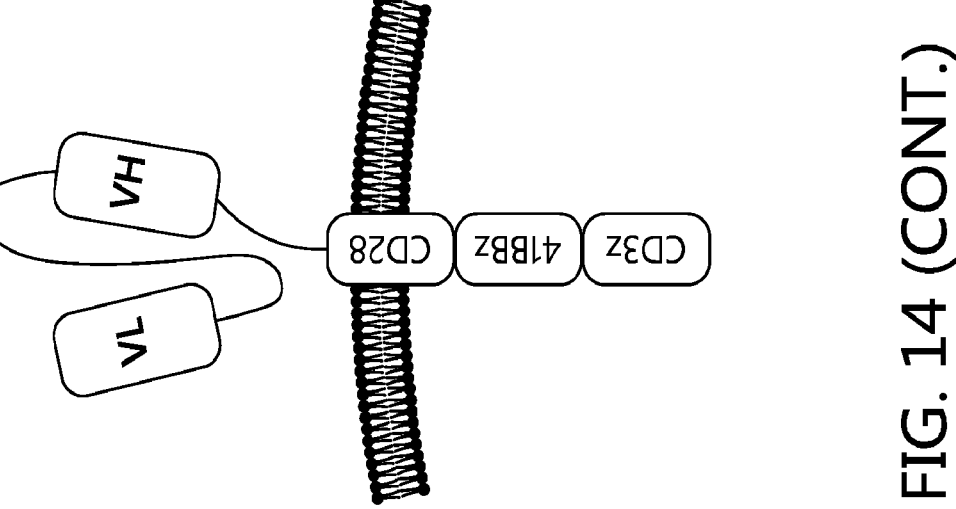
FIG. 14 is a schematic diagram of another exemplary GPC2-targeting CAR, GPC2.19VLVH.28H-28TM.41BBz (SEQ ID NO: 19). As discussed in greater detail below, this GPC2 CAR design demonstrated very good in vivo functional efficacy. The amino acid sequences corresponding to each of the components are shown.
Figure 15:
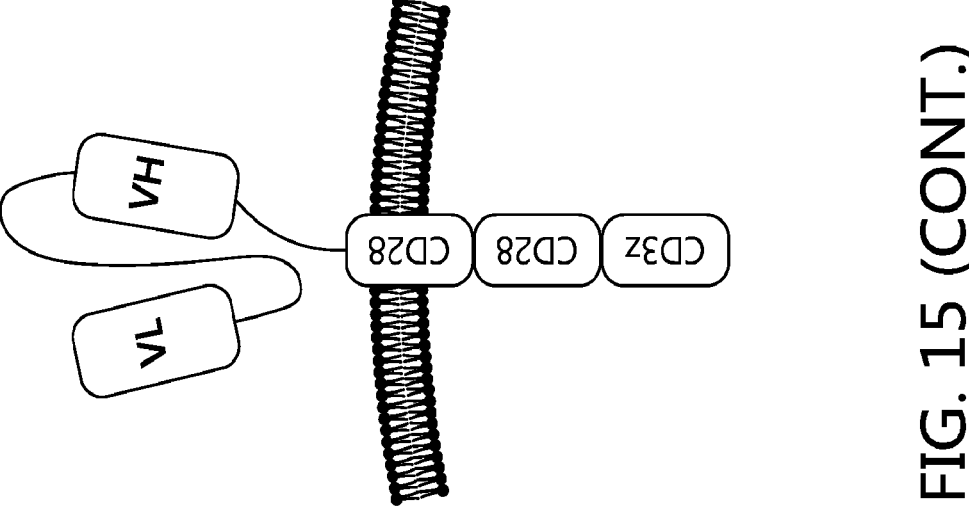
FIG. 15 is a schematic diagram of yet another exemplary GPC2-targeting CAR, GPC2.19VLVH.28H-28TM.28z (SEQ ID NO: 20). This GPC2 CAR design also demonstrated very good in vivo functional efficacy. The amino acid sequences corresponding to each of the components are also shown.

GPC2-Targeting CAR T-Cells Effectively Eradicate High Tumor in Patient-Derived Xenograft Models The experimental data described above demonstrate that rational design of GPC2-targeting CAR T-cells results in potent preclinical in vivo activity, laying the groundwork for clinical trials. Subsequently, additional experiments were performed to test GPC2.19 CAR T-cells in representative disease models with very high tumor burden and utilized patient-derived xenograft tumors (CHOP-N-421×) implanted into the flanks of immunodeficient mice. In these experiments, animals were allocated to two different study arms and infused with CAR T-cells when tumors were either established (range mean TU vol 0.22-0.24 cm$^3$) (FIG. 11A) or when animals exhibited very high tumor burden (range mean TU vol 0.65-0.78 cm$^3$) (FIG. 11E). Strikingly, GPC2.19 CAR T-cells were able to eradicate disease in both arms and led to a significant survival benefit (FIGS. 11C and 11G), again in the absence of clinical signs of toxicity or changes in body weight of treated animals (FIG. 11H). Our lead construct incorporating CD28 hinge-transmembrane domains and CD28 costimulatory domains outperformed those with 41BBz costimulatory domains (FIGS. 11B and 11F), despite comparable cell surface CAR expression (FIG. 11D). In conclusion, we have developed highly efficacious CAR T-cells targeting GPC2, with the potential to treat numerous adult and childhood GPC2+ malignancies in early phase clinical trials.

Example 7

General Methods and Techniques

Cells and Culture Conditions
The neuroblastoma cell lines SMS-SAN, NBSD and NGP-GPC2 were provided by Dr. John Maris (Children's Hospital of Philadelphia, CHOP). These cell lines were stably transduced with GFP and firefly luciferase. All tumor cell lines were cultured in RPMI-1640, supplemented with 10% heat-inactivated FBS (Gibco, Life Technologies), 10 mM HEPES, 100 U/mL penicillin, 100 µg/ml streptomycin and 2 mM L-glutamine (Gibco, Life technologies).

Generation of Binder Sequences Targeting GPC2
A naïve human Fab phage display library constructed from peripheral blood B cells of 50 healthy donors, was used for selection of Fabs against purified recombinant GPC2 ectodomain (R&D Systems) as previously described. The isolated Fabs were expressed, purified and tested for binding to the GPC2 ectodomain through ELISA.

Synthesis of Chimeric Antigen Receptors

Genes encoding for GPC2 scFv's were synthesized as either gene fragments (gBlock, IDT DNA) or gene-encoding plasmids synthesized by GeneArt (Life Technologies) and then cloned into MSGV1 retroviral expression vectors using restriction cloning (Roche) or Infusion cloning (Takara).
Retroviral Vector Production and T-Cell Transduction
Retroviral supernatant was produced via transient transfection of the 293GP packaging cell line as previously described. Briefly, 70% confluent cells were co-transfected via Lipofectamine 2000 (Life Technologies) in 150 mm Poly-D-Lysine culture dishes with the plasmids encoding the CARs and the RD114 envelope protein. Media was replaced at 24 and 48 hours post transfection. Viral supernatant was harvested 48 and 72 hours post-transfection and centrifuged to remove cell debris and stored at −80° C. until use.
Primary human T cells were isolated from healthy donors using the RosetteSep Human T cell Enrichment kit (Stem Cell Technologies) using buffy coats were derived from the Stanford Blood Center and processed according to the manufacturer's protocol using Lymphoprep density gradient medium and SepMate-50 tubes. Isolated T cells were cryopreserved in CryoStor CS10 cryopreservation medium (Stem Cell Technologies). Cryopreserved T cells were thawed and activated with Human T-Expander CD3/CD28 Dynabeads (Gibco) at a 3:1 beads: cell ratio in AIM-V media supplemented with 5% FBS, 10 mM HEPES, 2 mM l-glutamine, 100 U/mL penicillin, and 100 µg/mL streptomycin (Gibco) and with 100 IU/ml of recombinant IL-2 (Preprotech). T cells were transduced with retroviral vector on days 2 and 3 post activation and anti-CD3/CD28 beads were removed on day 5. CAR T-cells were maintained at 0.3-1× 10$^6$ cells per mL in T cell medium with IL2. CAR expression was assessed by Flow Cytometry after incubation with soluble, recombinant, human GPC2 (R&D systems) labelled with Dylight488 or Dylight650. CAR T cells were used for in vitro assays or transferred into mice on day 10 post activation.
Flow Cytometry
Data was collected with an LSR Fortessa X-20 (BD Bioscience) and analyzed using the FlowJo software. Cells were harvested, washed twice with FACS buffer (PBS supplemented with 2% FBS and 0.4% 0.5 M EDTA) and stained for 30 min in the dark on ice. Cells were washed 3 times with FACS buffer after each incubation step. Cells were gated on viable cells and singlet discrimination (FSC-A/FSC-H) was performed before assessment of antigen expression. Semiquantitative assessment of GPC2 antigen density in molecules per cell was estimated using the BD Quantibrite Kit per the manufacturer's protocol.
Enzyme-Linked Immunosorbent Assay (ELISA)
Cytokine release was assayed by co-incubating 0.1×10$^6$ CAR+ T cells and 0.1×10$^6$ tumor cells in complete RPMI-1640 in triplicates. At 24 hours, culture media supernatant was collected and cytokines were measured using IFNγ and IL-2 (BioLegend).
IncuCyte Killing Assays
For IncuCyte killing assays, 0.05×10$^6$ GPF-positive tumor cells were plated in triplicates in 96-well flat-bottom plates and co-incubated with CAR-positive T-cells or an equivalent number of CD19 CTRL CAR T cells at either 1:1, 1:5 or 1:8 effector to target ratios in 200 μL RPMI-1640. Plates were imaged every 2-3 hours using the IncuCyte ZOOM Live-Cell analysis system (Essen Bioscience) and 4 images per well at 10× zoom were collected at each time point. Total integrated GFP intensity per well was assessed as a quantitative measure of viable, GFP-positive tumor cells. Values were normalized to the starting measurement and plotted over time.

In Vivo Experiments

For orthotopic tumor engraftment, 6-8 weeks old NSG mice were xenografted with $1\times10^6$ NBSD-GFP-Luciferase cells into the left subrenal capsule as previously described (Patterson et al., 2011). Tumor cells were harvested, washed twice with PBS and resuspended as $1\times10^6$ cells per 100 μL and stored on ice until injection. Tumor engraftment and growth was followed via bioluminescence imaging on an IVIS spectrum instrument (Caliper Life Science, Hopkinton, MA, USA) and quantified with Living Image software (PerkinElmer, Waltham, MA, USA). Isofluorane-anesthe-tized mice were imaged 4 minutes after 3 mg D-luciferin (Perkin-Elmer) was injected intraperitoneally at an exposure time of 30 seconds. Four or five days after tumor implantation, mice received $10\times10^6$ CAR-positive GPC2 CAR T-cells or an equivalent number of FMC63.CTRL CAR T cells in 200 μL PBS intravenously via tail vein injections. CHOP-N-421× PDX tumors were implanted into the flanks of C.B-17 scid mice (C.B-Igh-1b/IcrTac-Prkdcscid; Taconic Biosciences) mice. Animals bearing engrafted tumors were then randomly assigned into 2 study arms, ensuring that each group/arm had a similar mean tumor volume at study enrollment. Tumor volumes were measured at least twice weekly using calipers and tumor volumes were calculated as follows: volume=((diameter½+ diameter2/2) 3*0.5236)/1000. All mice weights were also measured at least twice weekly and mice were monitored daily for signs of clinical toxicity. Mice were euthanized when tumor volumes reached/exceeded 3 cm³ or an animal displayed signs of clinical toxicity including excessive weight loss.

Antibody Generation of GPC2.IgG1 and Antigen Binding Assessment by ELISA

Fully human GPC2.19-IgG1 antibody was transiently expressed in 293 FreeStyle cells. Antibody was isolated from culture supernatant using protein A beads (Fisher).

Isolated antibody was washed using PBS and Amicon 10,000 kDa filter columns. Binding of GPC2.19-IgG1 to GPC2 antigen was measured via ELISA. Recombinant human and mouse GPC2 antigens were purchased from R&D Systems, dry milk was from BioRad. All other chemicals were biological grade. High absorbance 96-well ELISA plates were coated with antigen overnight using 50 ml stock solution per well at 2 μg/ml. Experiments were performed at 4° C. Antigen coated plates were blocked using 3% milk in PBS and 0.5% TWEEN®20 for 2 h. Blocked plates were incubated with one of the tested primary antibodies for 1 hour, washed 5 times (BioTek plate washer) and incubated with anti-human Fc-HRP (Sigma) as the secondary antibody for 1 hour. Secondary antibody was washed five times, the HRP substrate TMB (Sigma) was added and plate was incubated for 3 minutes. TMB oxidation was stopped with 2.5 M sulfuric acid. Plates' absorbance was measured on plate reader (BioRad) at 415 nm.

Toxicity Evaluation of GPC2 CAR T-Cells in NSG Xeno-graft Model

Orthotopic tumors ($1\times10^6$ NBSD-GFP-Luciferase cells) were engrafted into the left subrenal capsule of 8 weeks old NSG mice as described above and treated with $10\times10^6$ CAR+ GPC2 CAR T-cells (n=3) or an equivalent number of FMC63.CTRL CAR T cells (n=3) four days after tumor implantation. Tumor growth via bioluminescence imaging and body weight of animals was measured every 2-4 days. Mice were euthanized 14 days after CAR T-cell injection. Tissues were collected and processed by the Comparative Medicine Animal Histology Department at Stanford University and analyzed blindly by a board-certified veterinary pathologist. Tissues were collected in 10% neutral buffered formalin (NBF), and routinely processed for paraffin embedding, sectioned at 5.0 μm, and stained with hematoxylin and eosin (H&E). Tissues were visualized using an Olympus BX43 upright microscope, and images captured using an Olympus DP27 camera and cellSens software. Blood was collected at the endpoint and processed and analyzed by the Animal Diagnostic Laboratory at the Stanford Veterinary Service Center.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. An isolated antibody or a functional fragment thereof that have a binding affinity for a glypican-2 (GPC2) polypeptide, wherein the antibody or functional fragment thereof comprises a variable heavy chain (VH) region and a variable light chain (VL) region, and wherein:
   (a) (i) the VH region comprises the variable heavy chain CDR 1, 2 and 3 (HCDR1, HCDR2, HCDR3) comprising the amino acid sequences as shown in SEQ ID NOS: 1, 2, and 3, respectively; and
      (ii) the VL region comprises the variable light chain CDR 1, 2 and 3 (LCDR1, LCDR2, LCDR3) comprising the amino acid sequences as shown in SEQ ID NOS: 4, 5, and 6, respectively;
   or
   (b) (i) the VH region comprises the variable heavy chain CDR 1, 2 and 3 (HCDR1, HCDR2, HCDR3) comprising the amino acid sequences as shown in SEQ ID NOS: 9, 10, and 11, respectively; and
      (ii) the VL region comprises the variable light chain CDR 1, 2 and 3 (LCDR1, LCDR2, LCDR3) comprising the amino acid sequences as shown in SEQ ID NOS: 12, 13, and 14, respectively,
wherein said isolated antibody is a non-naturally occurring antibody.

2. The antibody or functional fragment thereof of claim 1, wherein the VH region and the VL region comprise:
   (a) the sequences of SEQ ID NO: 7 and SEQ ID NO: 8, respectively; or
   (b) the sequences of SEQ ID NO: 15 and SEQ ID NO: 16, respectively.

3. The antibody or functional fragment thereof of claim 1, wherein:
   (i) the VH region comprises the variable heavy chain CDRs 1, 2 and 3 (HCDR1, HCDR2, and HCDR3) amino acid sequences as shown in SEQ ID NOS: 1, 2, and 3, respectively, and
   (ii) the VL region comprises the variable light chain CDR 1, 2 and 3 (LCDR1, LCDR2, LCDR3) comprising the amino acid sequences as shown in SEQ ID NOS: 4, 5, and 6, respectively.

4. The antibody or functional fragment thereof of claim 3, wherein the VH region and the VL region comprise the amino acid sequences of SEQ ID NO: 7 and SEQ ID NO: 8, respectively.

5. The antibody or functional fragment thereof of claim 1, wherein:
   (i) the VH region comprises the HCDR1, HCDR2, and HCDR3 amino acid sequences as shown in SEQ ID NOS: 9, 10, and 11, respectively; and
   ii) the VL region comprises the LCDR1, LCDR2, LCDR3 amino acid sequences as shown in SEQ ID NOS: 12, 13, and 14, respectively.

6. The antibody or functional fragment thereof of claim 5, wherein the VH region and the VL region comprise the amino acid sequences of SEQ ID NO: 15 and SEQ ID NO: 16, respectively.

7. A chimeric antigen receptor (CAR) comprising an GPC2-binding moiety derived from an antibody or an antigen-binding fragment thereof according to claim 1.

8. The chimeric antigen receptor of claim 7, comprising (i) a GPC2-binding moiety comprising an anti-GPC2 scFv region, (ii) a TMD, and (iii) an ICD, wherein the anti-GPC2 scFv region comprises:
   (a) (I) three variable heavy chain CDR 1, 2 and 3 (HCDR1, HCDR2, HCDR3) comprising the amino acid sequences as shown in SEQ ID NOS: 1, 2, and 3, respectively; and
      (II) three variable light chain CDR 1, 2 and 3 (LCDR1, LCDR2, LCDR3) comprising the amino acid sequences as shown in SEQ ID NOS: 4, 5, and 6, respectively;
   or
   (b) (I) three variable heavy chain CDR 1, 2 and 3 (HCDR1, HCDR2, HCDR3) comprising the amino acid sequences as shown in SEQ ID NOS: 9, 10, and 11, respectively; and
      (II) three variable light chain CDR 1, 2 and 3 (LCDR1, LCDR2, LCDR3) comprising the amino acid sequences as shown in SEQ ID NOS: 12, 13, and 14, respectively.

9. The chimeric antigen receptor of claim 8, wherein the ICD comprises a co-stimulatory domain.

10. The chimeric antigen receptor of claim 8, wherein the ICD comprises a CD3ζ ICD.

11. The chimeric antigen receptor of claim 8, further comprising an extracellular hinge domain operably linked downstream to the anti-GPC2 scFv region and upstream to the TMD.

12. The chimeric antigen receptor of claim 8, comprising:
   a) an anti-GPC2 scFv region;
   b) a CD28 hinge domain
   c) a CD28 TMD; and
   d) an ICD comprising a co-stimulatory domain derived from a 4-1BBz co-stimulatory domain or a CD28 co-stimulatory domain.

13. A recombinant nucleic acid molecule comprising a nucleic acid sequence that encodes:
   (a) an antibody or functional fragment thereof according to claim 1; or
   (b) a chimeric antigen receptor comprising the antibody or functional fragment thereof of (a).

14. A recombinant cell comprising one or more of the following:
   (a) an antibody or functional fragment thereof according to claim 1;
   (b) a chimeric antigen receptor comprising the antibody or functional fragment thereof of (a); and (c) a nucleic acid molecule encoding the antibody or functional fragment thereof of (a) and/or the chimeric antigen receptor of (b).

15. A method for making a recombinant cell, comprising:

a) providing a host cell capable of protein expression; and b) transducing the provided host cell with a recombinant nucleic acid according to claim 13 to produce a recombinant cell.

16. A pharmaceutical composition comprising a pharmaceutically acceptable carrier and one or more of the following:

(a) an antibody or functional fragment thereof according to claim 1;

(b) a chimeric antigen receptor comprising the antibody or functional fragment thereof of (a);

(c) a nucleic acid molecule encoding the antibody or functional fragment thereof of (a) and/or the chimeric antigen receptor of (b); and (d) a recombinant cell comprising an antibody or functional fragment thereof of (a), a chimeric antigen receptor of (b), and/or a nucleic acid molecule of (c).

17. A method for diagnosing and/or treating a cancer in a subject in need thereof, comprising administering to the subject a composition comprising one or more of the following:

(a) an antibody or functional fragment thereof according to claim 1;

(b) a chimeric antigen receptor comprising the antibody or functional fragment thereof of (a);

(c) a nucleic acid molecule encoding the antibody or functional fragment thereof of (a) and/or the chimeric antigen receptor of (b); and (d) a recombinant cell comprising an antibody or functional fragment thereof of (a), a chimeric antigen receptor of (b), and/or a nucleic acid molecule of (c).

18. A kit for the diagnosis and/or treatment a cancer in a subject in need thereof, the kit comprising one or more of the following:

(a) an antibody or a functional fragment thereof according to claim 1;

(b) a chimeric antigen receptor comprising the antibody or functional fragment thereof of (a);

(c) a nucleic acid molecule encoding the antibody or functional fragment thereof of (a) and/or the chimeric antigen receptor of (b); and (d) a recombinant cell comprising an antibody or functional fragment thereof of (a), a chimeric antigen receptor of (b), and/or a nucleic acid molecule of (c).

19. The chimeric antigen receptor of claim 8, wherein the anti-GPC2 scFv region comprises:

(I) the HCDR1, HCDR2, HCDR3 amino acid sequences as shown in SEQ ID NOS: 1, 2, and 3, respectively; and (II) the LCDR1, LCDR2, LCDR3 amino acid sequences as shown in SEQ ID NOS: 4, 5, and 6, respectively.

20. The chimeric antigen receptor of claim 19, wherein the anti-GPC2 scFv region comprises a VH region and a VL region comprising the amino acid sequences of SEQ ID NO: 7 and SEQ ID NO: 8, respectively.

21. The chimeric antigen receptor of claim 8, wherein the anti-GPC2 scFv region comprises:

(I) the HCDR1, HCDR2, HCDR3 amino acid sequences as shown in SEQ ID NOS: 9, 10, and 11, respectively; and (II) the LCDR1, LCDR2, LCDR3 amino acid sequences as shown in SEQ ID NOS: 12, 13, and 14, respectively.

22. The chimeric antigen receptor of claim 21, wherein the anti-GPC2 scFv region comprises a VH region and a VL region comprising the amino acid sequences of SEQ ID NO: 15 and SEQ ID NO: 16, respectively.

* * * * *